(12) United States Patent
Hirao et al.

(10) Patent No.: US 9,285,319 B2
(45) Date of Patent: Mar. 15, 2016

(54) NUCLEIC ACID BASE ANALOGS WITH QUENCHING AND FLUORESCENT ACTIVITIES AND APPLICATIONS THEREOF

(75) Inventors: Ichiro Hirao, Komae (JP); Michiko Hirao, Yokohama (JP); Shigeyuki Yokoyama, Yokohama (JP); Tsuneo Mitsui, Yokohama (JP); Rie Yamashige, Ohta (JP)

(73) Assignees: RIKEN, Wako-shi, Saitama (JP); TagCyx Biotechnologies, Yokohama-shi, Kanagawa (JP)

( * ) Notice: Subject to any disclaimer, the term of this patent is extended or adjusted under 35 U.S.C. 154(b) by 217 days.

(21) Appl. No.: 13/642,111

(22) PCT Filed: Apr. 21, 2011

(86) PCT No.: PCT/JP2011/060343
§ 371 (c)(1),
(2), (4) Date: Jan. 30, 2013

(87) PCT Pub. No.: WO2011/132801
PCT Pub. Date: Oct. 27, 2011

(65) Prior Publication Data
US 2013/0122506 A1     May 16, 2013

(30) Foreign Application Priority Data
Apr. 21, 2010   (JP) .................................. 2010-098319

(51) Int. Cl.
*C12Q 1/68*      (2006.01)
*C07H 21/02*     (2006.01)
(Continued)

(52) U.S. Cl.
CPC .......... *G01N 21/6486* (2013.01); *C07H 19/044* (2013.01); *C12Q 1/6818* (2013.01)

(58) Field of Classification Search
CPC ........... C12Q 1/6816; C12Q 2525/117; C07H 19/044
USPC ............ 536/4.1, 24.3, 26.6; 435/6.1; 422/430
See application file for complete search history.

(56) References Cited

U.S. PATENT DOCUMENTS

2010/0285598 A1   11/2010   Hirao et al.
2011/0053782 A1   3/2011    Hirao et al.
(Continued)

FOREIGN PATENT DOCUMENTS

JP    2004-506431 A    3/2004
JP    2007-61087 A     3/2007
(Continued)

OTHER PUBLICATIONS

Kimoto et al. JACS 2010, 132, 1 541 8-1 5426.*
(Continued)

*Primary Examiner* — Jezia Riley
(74) *Attorney, Agent, or Firm* — Birch, Stewart, Kolasch & Birch, LLP

(57) ABSTRACT

It is an object of the present invention to provide quenching or fluorescent nucleic acid base analogs and applications thereof. The quencher of the present invention has a 2-nitropyrrole structure represented by Formula I:

[Formula 1]

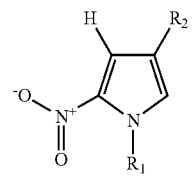

Formula I (in Formula I, $R_1$ and $R_2$ are groups independently selected from the group consisting of:
ribose and deoxyribose;
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocylic rings containing nitrogen or sulfur, and one or more aromatic rings;
sugars, sugar chains, amino acids, and peptides; and
fluorescent molecules linked via linkers).

2 Claims, 39 Drawing Sheets
(21 of 39 Drawing Sheet(s) Filed in Color)

Dss     Pn

Ds      Px

Artificial base pairs of a quenching basr (pn or Px) and a base complementary thereto (Ds or Dss).

(51) Int. Cl.
C07H 21/04 (2006.01)
G01N 21/64 (2006.01)
C07H 19/044 (2006.01)

(56) References Cited

U.S. PATENT DOCUMENTS

2012/0231462 A1  9/2012  Hirao et al.
2012/0245340 A1  9/2012  Hirao et al.

FOREIGN PATENT DOCUMENTS

WO    WO 02/14555 A2    2/2002
WO    WO 2009/123216 A1  10/2009

OTHER PUBLICATIONS

Stratagene Catalog 1988 p. 39.*
Börjesson et al., "Nucleic Acid Base Analog FRET-Pair Facilitating Detailed Structural Measurements in Nucleic Acid Containing Systems", J. Am. Chem. Soc., vol. 131, 2009, (Published on Web Mar. 9, 2009), pp. 4288-4293.
Extended European Search Report, dated Sep. 26, 2013, for European Application No. 11772132.4.
Hirao et al., "An Efficient Unnatural Base Pair for PCR Amplification", J. Am. Chem. Soc., vol. 129, No. 50, 2007, (Published on Web Nov. 21, 2007), pp. 15549-15555.
Hirao et al., "An unnatural hydrophobic base pair system: site-specific incorporation of nucleotide analogs into DNA and RNA", Nature Methods, vol. 3, No. 9, Sep. 2006, (Published online Aug. 23, 2006), pp. 729-735.
Hirao et al., "Development of an unnatural base pair for efficient PCR amplification", Nucleic Acids Symposium Series, No. 51, 2007, pp. 9-10, XP-002679105.
International Search Report and Written Opinion of the International Searching Authority (Forms PCT/ISA/220, PCT/ISA/210 and PCT/ISA/237), dated Aug. 2, 2011, for International Application No. PCT/JP2011/060343, including English translation of International Search Report.
Kimoto et al., "A New Unnatural Base Pair System between Fluorophore and Quencher Base Analogues for Nucleic Acid-Based Imaging Technology", J. AM. Chem. Soc., vol. 132, No. 43, 2010, (Published on Web Oct. 12, 2010), pp. 15418-15426.
Kimoto et al., "A Unique Fluorescent Base Analogue for the Expansion of the Genetic Alphabet", J. Am. Chem. Soc., vol. 132, No. 14, 2010, (Published on Web Mar. 24, 2010), pp. 4988-4989.
Kimoto et al., "An unnatural base pair system for efficient PCR amplification and functionalization of DNA molecules", Nucleic Acids Research, vol. 37, No. 2, 2009, (Published online Dec. 10, 2008), pp. 1-9, XP008155966.
Kimoto et al., "Efficient PCR amplification by an unnatural base pair system", Nucleic Acids Symposium Series, No. 52, 2008, (Symposium date: Sep. 8, 2008), pp. 469-470, XP008145065.
Kimoto et al., "Fluorescent probing for RNA molecules by an unnatural base-pair system", Nucleic Acids Research, vol. 35, No. 16, 2007, (Published online Aug. 9, 2007), pp. 5360-5369.
Kimoto et al., "Sequences around the unnatural base pair in DNA templates for efficient replication", Nucleic Acids Symposium Series, No. 52, 2008, (Symposium date: Sep. 8, 2008), pp. 457-458, XP008145066.
Kimoto et al., "Site-specific incorporation of functional components into RNA by transcription using unnatural base pair systems", Nucleic Acids Symposium Series, No. 53, 2009, (Symposium date: Sep. 27, 2009), pp. 73-74.
Liu et al., "Size-Expanded Analogues of dG and dC: Synthesis and Pairing Properties in DNA", J. Org. Chem., vol. 70, No. 2, 2005, (Published on Web Dec. 23, 2004), pp. 639-647.
Loakes et al., "3-Nitropyrrole and 5-nitroindole as universal bases in primers for DNA sequencing and PCR", Nucleic Acids Research, vol. 23, No. 13, 1995, pp. 2361-2366.
Mitsui et al., "Characterization of fluorescent, unnatural base pairs", Tetrahedron, vol. 63, 2007, (Available online Feb. 3, 2007), pp. 3528-3537.
Tyagi et al., "Molecular Beacons: Probes that Fluoresce upon Hybridization", Nature Biotechnology, vol. 14, Mar. 1996, pp. 303-308, XP-002427012.
Zhang et al., "Absorption and Fluorescence Emission Spectroscopic Characters of Size-Expanded yDNA Bases and Effect of Deoxyribose and Base Pairing", J. Phys. Chem. B, vol. 113, No. 4, 2009, (Published on Web Jan. 7, 2009), pp. 1173-1181.
Zhao et al., "Synthesis of HIV-1 ψ-site RNA sequences with site specific incorporation of the fluorescent base analog 2-aminopurine", Tetrahedron, vol. 63, 2007, (Available online Feb. 20, 2007), pp. 3575-3584.

* cited by examiner

Artificial base pairs of a quenching base (pn or Px) and a base complementary thereto (Ds or Dss).

Fig. 2 Structures of an artificial quenching base Pn and its 4'-derivatives used in Examples of the present invention Fig. 3  Structures of an artificial quenching base Px and its derivatives used in Examples of the present invention Artificial base Ds and artificial fluorescent bases Dss, Dsss, and Dsav which are complementary to Pn or Px Amidite reagents where an artificial fluorescent base Dss or s is linked to a natural base Primer extension reaction by a Klenow fragment of a DNA polymerase I derived from Escherichia coli using a template DNA comprising Pn and dDssTP PCR amplification of a DNA comprising Ds using a Dss-Px base pair Detection of products through real-time PCR using fluorescent molecule (Cy3)-liked Px base having a quenching activity by gel electrophoresis Visualization of PCR using a combination of a fluorescent molecule (Cy3)-linked Px base having a quenching activity and an artificial fluorescent base s

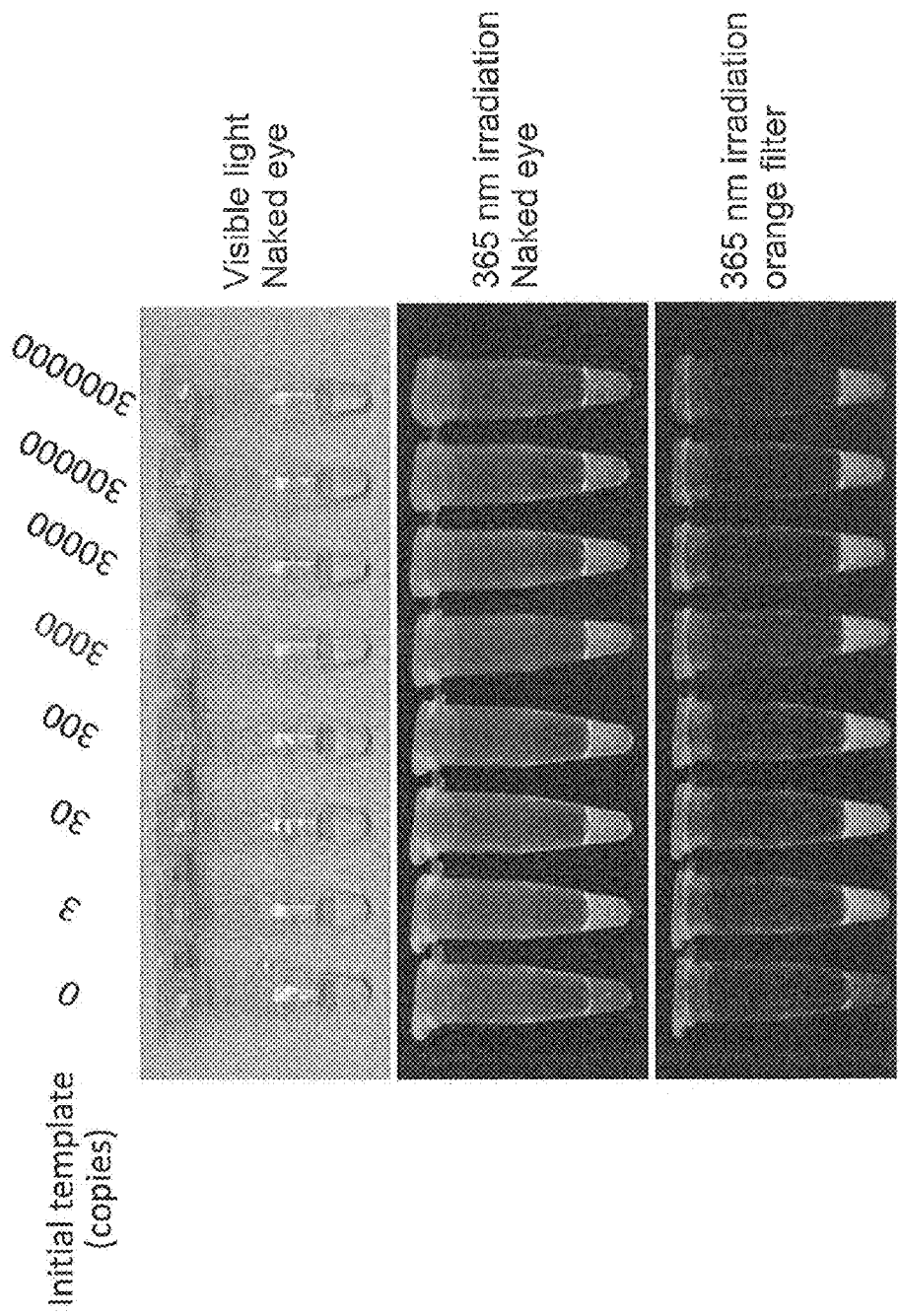

Visualization of PCR using a combination of a fluorescent molecule (Cy3)-linked Px base having a quenching activity and an artificial fluorescent base s

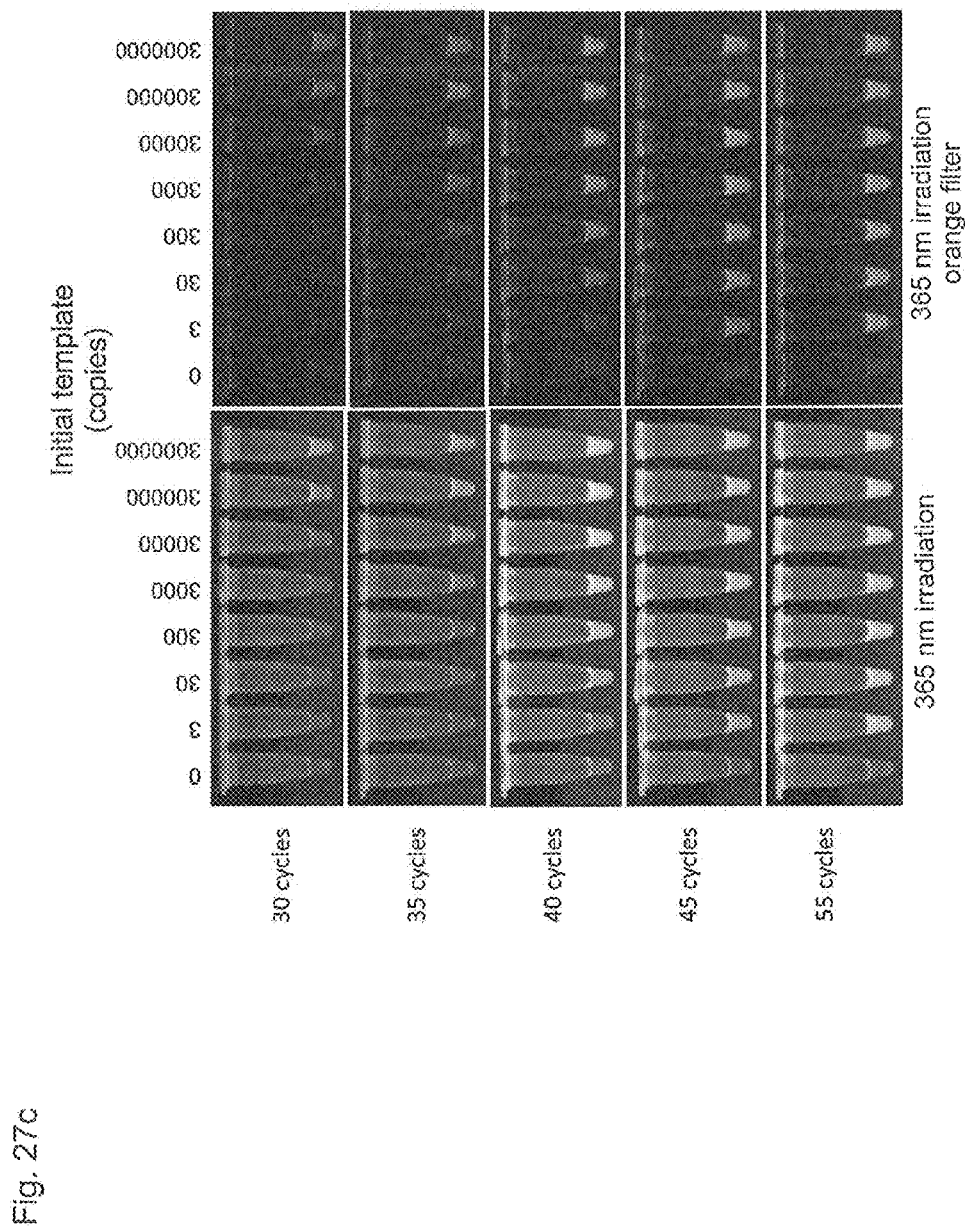

Fig. 27d
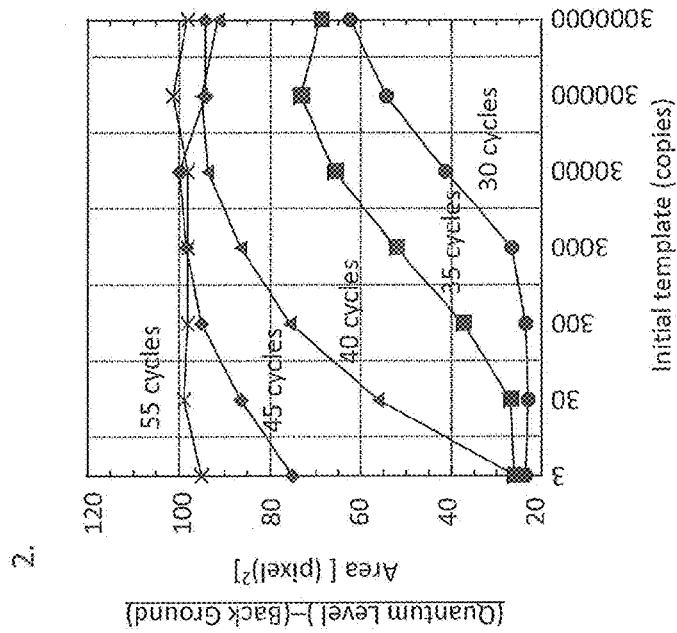
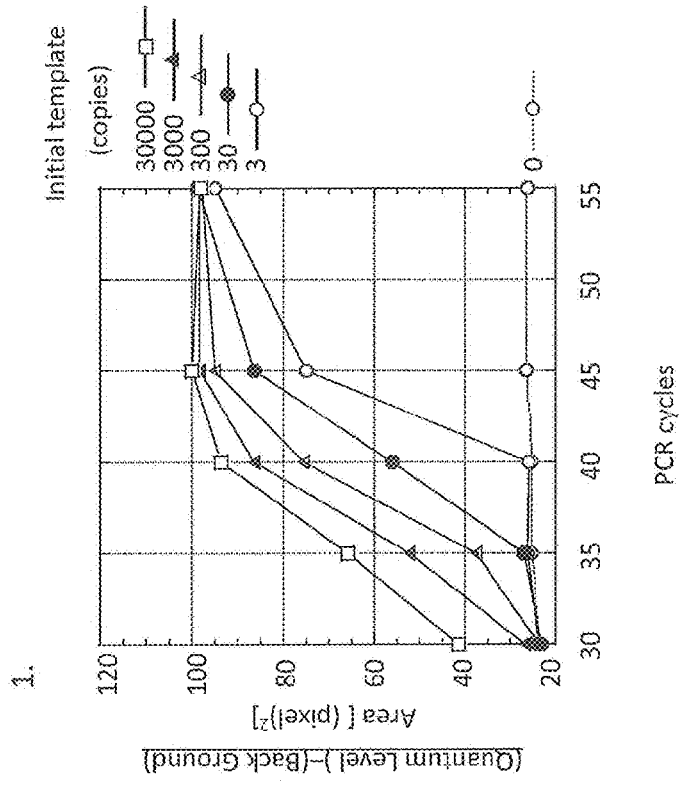
Quantification of the fluorescence intensity of each PCR tube shown in Fig. 27c Gel electrophoretic detection of products by PCR (55 cycles) using a primer of a combination of a fluorescent molecule (Cy3)-linked Px base having a quenching activity and an artificial fluorescent base s

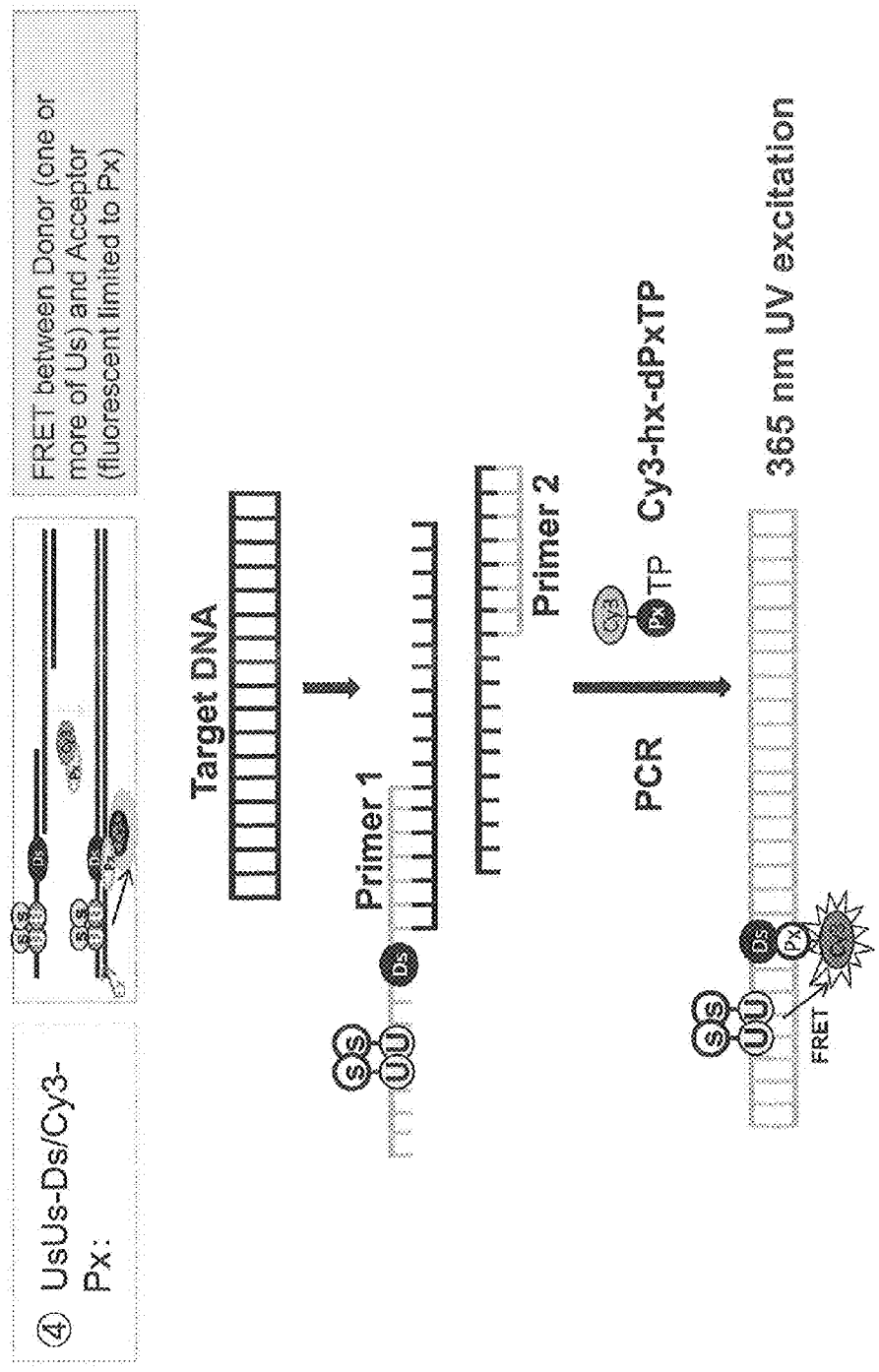

Sequences of each primer and template and conditions for PCR using s-hx-dU, (Us) and a Ds-Px base pair

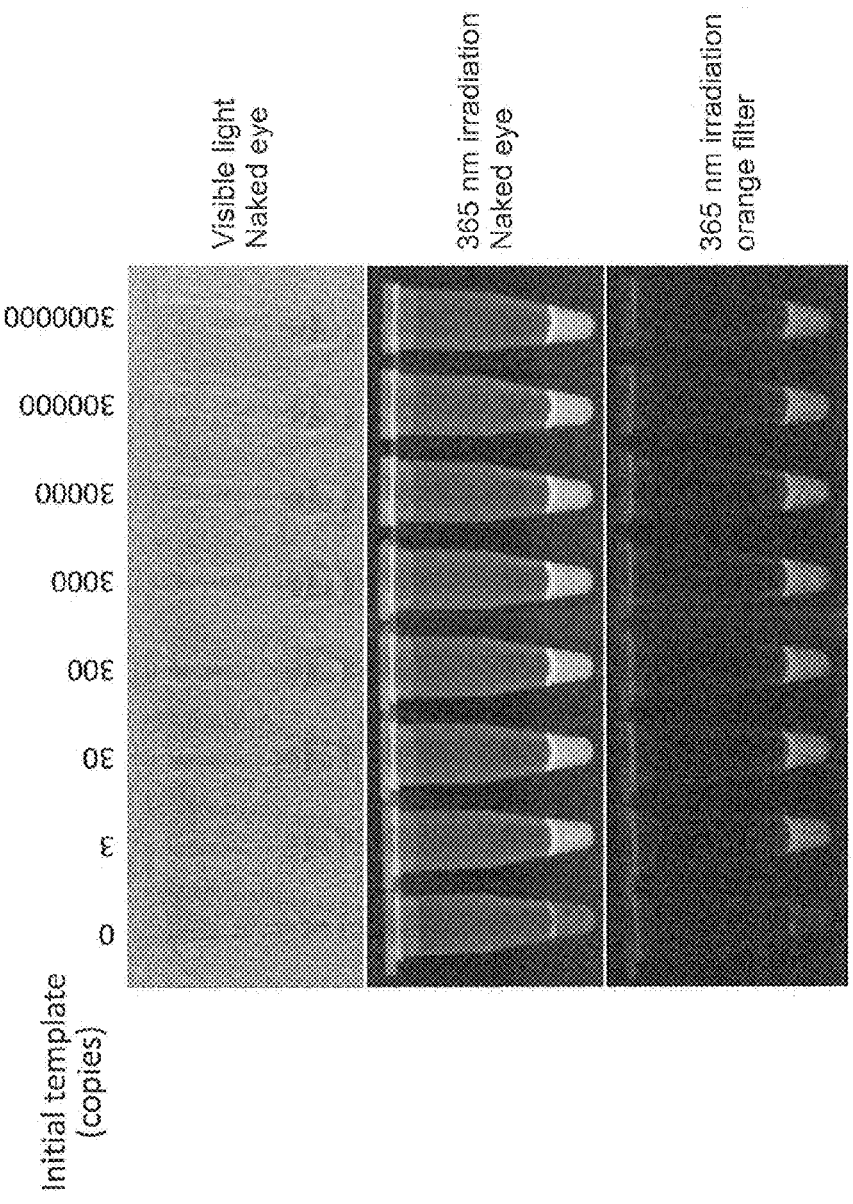
Fig. 29d  Visualization of DNA amplification products by the respective PCR cycles shown in Fig. 29c

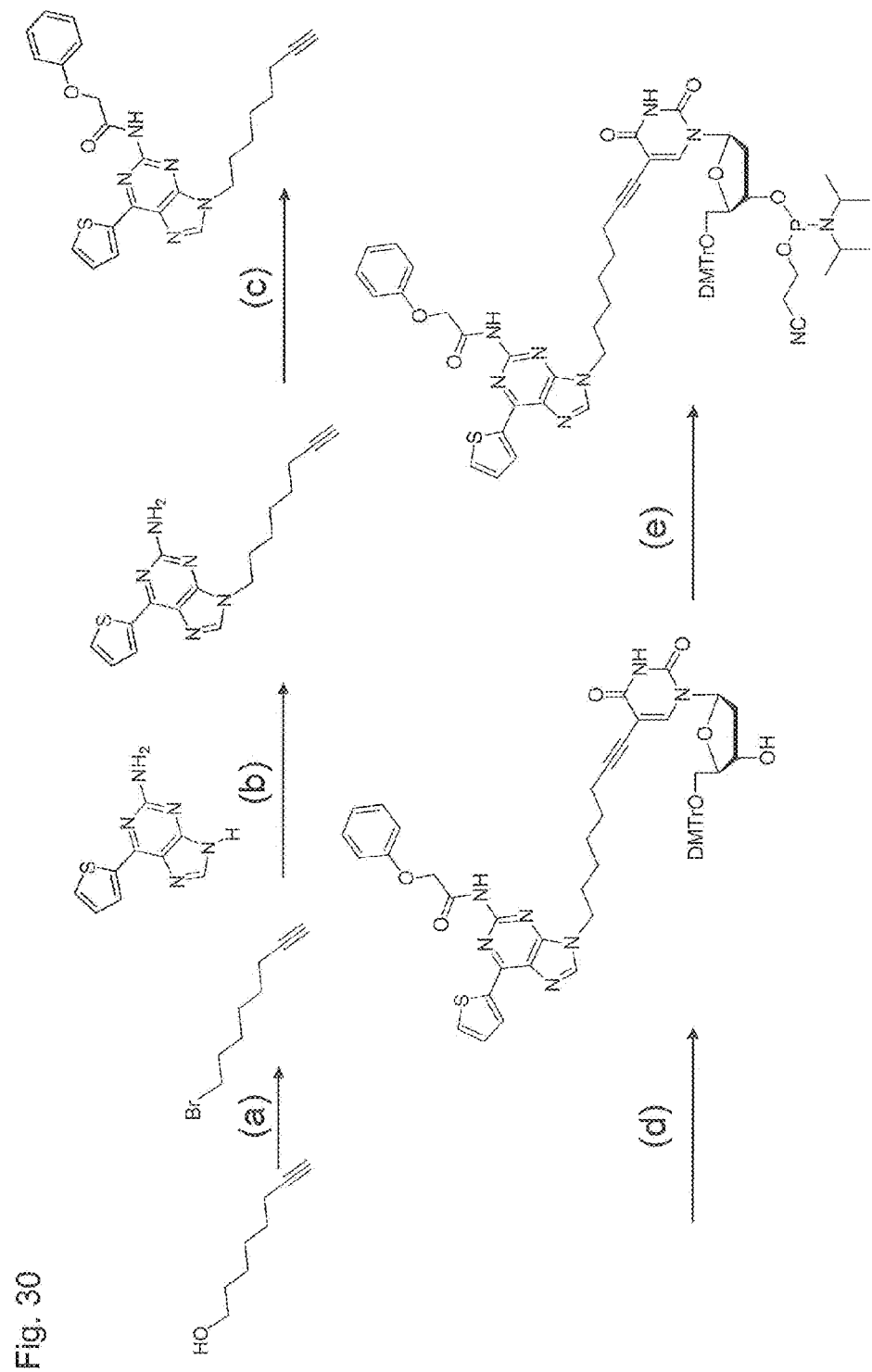
Fig. 30  Chemical synthesis of an s-hx-dU amidite reagent

Method of detecting products by PCR using a nucleoside derivative (Fig. 6, s2-hx-dC, (Css)) where two fluorescent base (s) molecules are linked to a natural base via a linker and a Ds-Px base pair

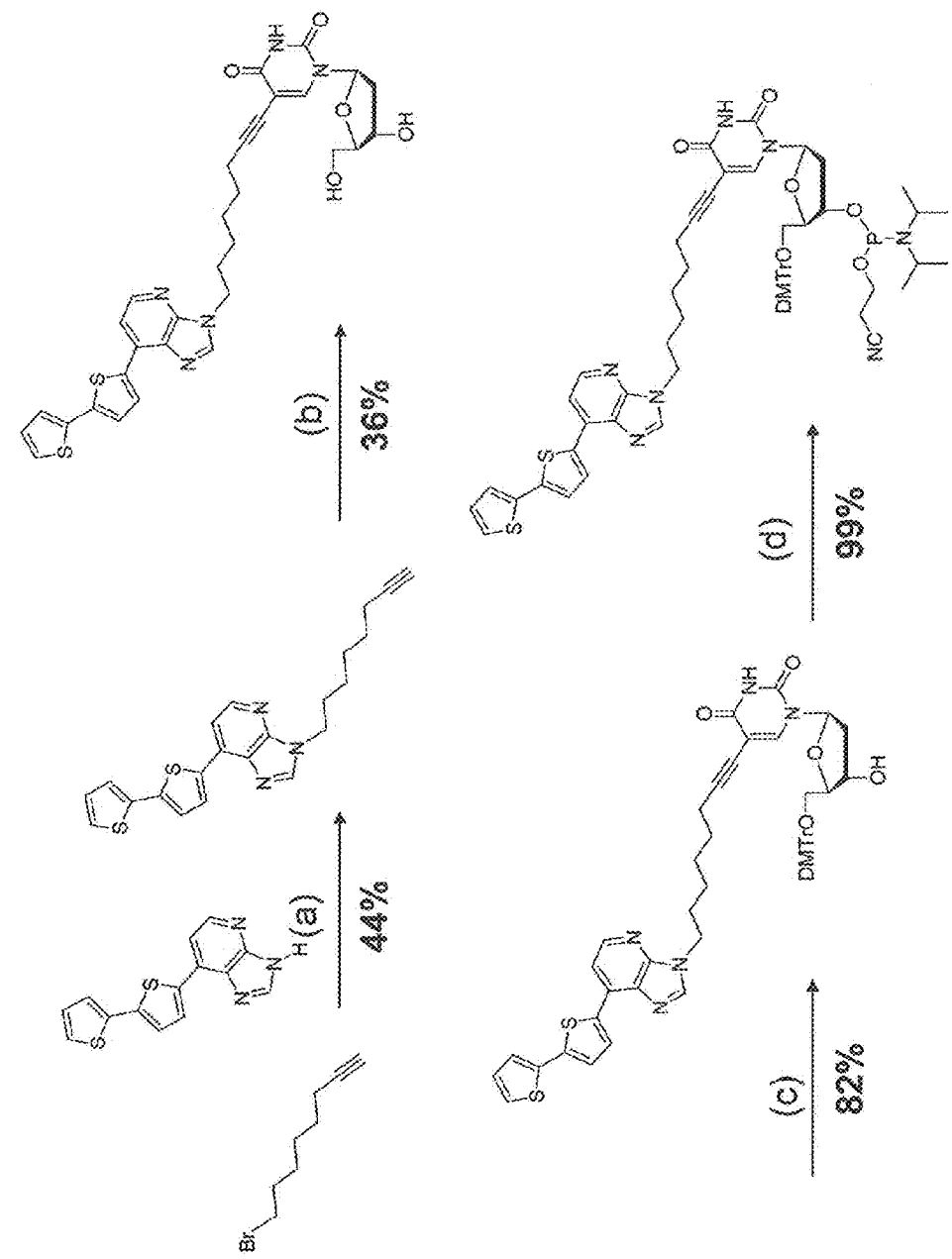
Fig. 33 Chemical synthesis of a Dss-hx-dU amidite reagent

SEQUENCE LISTING

```
<160> NUMBER OF SEQ ID NOS: 27

<210> SEQ ID NO 1
<211> LENGTH: 12
<212> TYPE: DNA
<213> ORGANISM: Artificial
<220> FEATURE:
<223> OTHER INFORMATION: DNA fragment for testing quenching
<220> FEATURE:
<221> NAME/KEY: misc_feature
<222> LOCATION: (7)..(7)
<223> OTHER INFORMATION: n stands for artificial base Dss

<400> SEQUENCE: 1
ggtaacnatg cg                                                          12

<210> SEQ ID NO 2
<211> LENGTH: 12
<212> TYPE: DNA
<213> ORGANISM: Artificial
<220> FEATURE:
<223> OTHER INFORMATION: DNA fragment for testing quenching
<220> FEATURE:
<221> NAME/KEY: misc_feature
<222> LOCATION: (6)..(6)
<223> OTHER INFORMATION: n stands for any artificial base, Pn, Dss, Ds
      or natural base, t

<400> SEQUENCE: 2
cgcatngtta cc                                                          12
```

```
<210> SEQ ID NO 3
<211> LENGTH: 12
<212> TYPE: DNA
<213> ORGANISM: Artificial
<220> FEATURE:
<223> OTHER INFORMATION: DNA fragment for testing quenching
<220> FEATURE:
<221> NAME/KEY: misc_feature
<222> LOCATION: (7)..(7)
<223> OTHER INFORMATION: n stands for artificial base Ds

<400> SEQUENCE: 3
ggtaacnatg cg                                                            12

<210> SEQ ID NO 4
<211> LENGTH: 20
<212> TYPE: DNA
<213> ORGANISM: Artificial
<220> FEATURE:
<223> OTHER INFORMATION: primer for PCR

<400> SEQUENCE: 4
actcactata gggaggaaga                                                    20

<210> SEQ ID NO 5
<211> LENGTH: 20
<212> TYPE: DNA
<213> ORGANISM: Artificial
<220> FEATURE:
<223> OTHER INFORMATION: primer for PCR

<400> SEQUENCE: 5
actcactata gggagcttct                                                    20

<210> SEQ ID NO 6
<211> LENGTH: 35
<212> TYPE: DNA
<213> ORGANISM: Artificial
<220> FEATURE:
<223> OTHER INFORMATION: template for PCR
<220> FEATURE:
<221> NAME/KEY: misc_feature
<222> LOCATION: (7)..(7)
<223> OTHER INFORMATION: n stands for artificial base Dss

<400> SEQUENCE: 6
agctctntct tcctccctat agtgagtcgt attat                                   35

<210> SEQ ID NO 7
<211> LENGTH: 35
<212> TYPE: DNA
<213> ORGANISM: Artificial
<220> FEATURE:
<223> OTHER INFORMATION: template for PCR
<220> FEATURE:
<221> NAME/KEY: misc_feature
<222> LOCATION: (7)..(7)
<223> OTHER INFORMATION: n stands for any natural base a, g, c, t or
      artificial base Pn

<400> SEQUENCE: 7
tcgaganaga agctccctat agtgagtcgt attat                                   35

<210> SEQ ID NO 8
<211> LENGTH: 23
<212> TYPE: DNA
<213> ORGANISM: Artificial
<220> FEATURE:
<223> OTHER INFORMATION: primer for PCR
```

```
<400> SEQUENCE: 8
ataatacgac tcactatagg gag                                           23

<210> SEQ ID NO 9
<211> LENGTH: 35
<212> TYPE: DNA
<213> ORGANISM: Artificial
<220> FEATURE:
<223> OTHER INFORMATION: template for PCR
<220> FEATURE:
<221> NAME/KEY: misc_feature
<222> LOCATION: (29)..(29)
<223> OTHER INFORMATION: n stands for artificial base Pn or Pa

<400> SEQUENCE: 9
tattatgctg agtgatatcc ctcgaagana gagct                              35

<210> SEQ ID NO 10
<211> LENGTH: 55
<212> TYPE: DNA
<213> ORGANISM: Artificial
<220> FEATURE:
<223> OTHER INFORMATION: template for PCR
<220> FEATURE:
<221> NAME/KEY: misc_feature
<222> LOCATION: (30)..(30)
<223> OTHER INFORMATION: n stands for artificial base Ds

<400> SEQUENCE: 10
tttcacacag gaaacagcta tgacggcccn ttgccctata gtgagtcgta ttatc         55

<210> SEQ ID NO 11
<211> LENGTH: 55
<212> TYPE: DNA
<213> ORGANISM: Artificial
<220> FEATURE:
<223> OTHER INFORMATION: template for PCR

<400> SEQUENCE: 11
tttcacacag gaaacagcta tgacggatcc attccctata gtgagtcgta ttatc         55

<210> SEQ ID NO 12
<211> LENGTH: 40
<212> TYPE: DNA
<213> ORGANISM: Artificial
<220> FEATURE:
<223> OTHER INFORMATION: primer for PCR

<400> SEQUENCE: 12
cgttgtaaaa cgacggccag gataatacga ctcactatag                         40

<210> SEQ ID NO 13
<211> LENGTH: 24
<212> TYPE: DNA
<213> ORGANISM: Artificial
<220> FEATURE:
<223> OTHER INFORMATION: Primer for PCR

<400> SEQUENCE: 13
tttcacacag gaaacagcta tgac                                          24

<210> SEQ ID NO 14
<211> LENGTH: 20
<212> TYPE: DNA
<213> ORGANISM: Artificial
<220> FEATURE:
<223> OTHER INFORMATION: primer for sequencing
```

```
<400> SEQUENCE: 14
cgttgtaaaa cgacggccag                                              20

<210> SEQ ID NO 15
<211> LENGTH: 25
<212> TYPE: DNA
<213> ORGANISM: Artificial
<220> FEATURE:
<223> OTHER INFORMATION: primer for PCR

<400> SEQUENCE: 15
catgtagatg ccatcaaaga agctc                                        25

<210> SEQ ID NO 16
<211> LENGTH: 29
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (9)..(9)
<223> OTHER INFORMATION: n stands for artificial base Dss

<400> SEQUENCE: 16
aataatgcnt cctcaaaggt ggtgacttc                                    29

<210> SEQ ID NO 17
<211> LENGTH: 98
<212> TYPE: DNA
<213> ORGANISM: Artificial
<220> FEATURE:
<223> OTHER INFORMATION: template for PCR

<400> SEQUENCE: 17
catgtagatg ccatcaaaga agctctgagc ctcctaaatg acatgcgtgc tctggagaac  60
gaaaagaacg aagacgtaga agtcaccacc tttgagga                          98

<210> SEQ ID NO 18
<211> LENGTH: 34
<212> TYPE: DNA
<213> ORGANISM: Artificial
<220> FEATURE:
<223> OTHER INFORMATION: Hairpin ssDNA (34mer)
<220> FEATURE:
<221> NAME/KEY: misc_feature
<222> LOCATION: (6)..(6)
<223> OTHER INFORMATION: n stands for artificial base Dss
<220> FEATURE:
<221> NAME/KEY: misc_feature
<222> LOCATION: (19)..(19)
<223> OTHER INFORMATION: n stands for artificial base Pn

<400> SEQUENCE: 18
catctncatg aaaacatgna gatgccatca aaga                              34

<210> SEQ ID NO 19
<211> LENGTH: 12
<212> TYPE: DNA
<213> ORGANISM: Artificial
<220> FEATURE:
<223> OTHER INFORMATION: ssDNA (12mer)
<220> FEATURE:
<221> NAME/KEY: misc_feature
<222> LOCATION: (6)..(6)
<223> OTHER INFORMATION: n stands for artificial base Dss
```

<400> SEQUENCE: 19
cgcatngtta cc                                                      12

<210> SEQ ID NO 20
<211> LENGTH: 26
<212> TYPE: DNA
<213> ORGANISM: Artificial
<220> FEATURE:
<223> OTHER INFORMATION: molecular beacon MB-C
<220> FEATURE:
<221> NAME/KEY: misc_feature
<222> LOCATION: (5)..(5)
<223> OTHER INFORMATION: n stands for artificial base Dss
<220> FEATURE:
<221> NAME/KEY: misc_feature
<222> LOCATION: (22)..(22)
<223> OTHER INFORMATION: n stands for artificial base Pn

<400> SEQUENCE: 20
acgcncgggg attcctctat gngcgt                                       26

<210> SEQ ID NO 21
<211> LENGTH: 71
<212> TYPE: DNA
<213> ORGANISM: Artificial
<220> FEATURE:
<223> OTHER INFORMATION: target DNA for molecular beacon

<400> SEQUENCE: 21
attgagccat acggaccatg gcttcataaa tagaggaatc cccgtgtggg tggtatttac   60
ccatgacatc c                                                       71

<210> SEQ ID NO 22
<211> LENGTH: 71
<212> TYPE: DNA
<213> ORGANISM: Artificial
<220> FEATURE:
<223> OTHER INFORMATION: target DNA for moleculat beacon

<400> SEQUENCE: 22
attgagccat acggaccatg gcttcataaa tagagaaatc cccgtgtggg tggtatttac   60
ccatgacatc c                                                       71

<210> SEQ ID NO 23
<211> LENGTH: 26
<212> TYPE: DNA
<213> ORGANISM: Artificial
<220> FEATURE:
<223> OTHER INFORMATION: molecular beacon MB-T
<220> FEATURE:
<221> NAME/KEY: misc_feature
<222> LOCATION: (5)..(5)
<223> OTHER INFORMATION: n stands for artificial base Dss
<220> FEATURE:
<221> NAME/KEY: misc_feature
<222> LOCATION: (22)..(22)
<223> OTHER INFORMATION: n stands for artificial base Pn

<400> SEQUENCE: 23
acgcncgggg atttctctat gngcgt                                       26

<210> SEQ ID NO 24
<211> LENGTH: 29
<212> TYPE: DNA
<213> ORGANISM: Artificial
<220> FEATURE:
<223> OTHER INFORMATION: primer for PCR

```
<220> FEATURE:
<221> NAME/KEY: misc_feature
<222> LOCATION: (9)..(9)
<223> OTHER INFORMATION: n stands for artificial base Ds

<400> SEQUENCE: 24
aataatgcnt cctcaaaggt ggtgacttc                                29

<210> SEQ ID NO 25
<211> LENGTH: 30
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (6)..(7)
<223> OTHER INFORMATION: n stands for artificial base s
<220> FEATURE:
<221> NAME/KEY: misc_feature
<222> LOCATION: (10)..(10)
<223> OTHER INFORMATION: n stands for artificial base Ds

<400> SEQUENCE: 25
aataanngcn tcctcaaagg tggtgacttc                               30

<210> SEQ ID NO 26
<211> LENGTH: 30
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (6)..(7)
<223> OTHER INFORMATION: n stands for artificial base s
<220> FEATURE:
<221> NAME/KEY: misc_feature
<222> LOCATION: (10)..(10)
<223> OTHER INFORMATION: n stands for artificial base Ds

<400> SEQUENCE: 26
aataanngcn tcctcaaagg tggtgacttc                               30

<210> SEQ ID NO 27
<211> LENGTH: 30
<212> TYPE: DNA
<213> ORGANISM: Artificial
<220> FEATURE:
<223> OTHER INFORMATION: primer for PCR
<220> FEATURE:
<221> NAME/KEY: misc_feature
<222> LOCATION: (6)..(7)
<223> OTHER INFORMATION: n stands for artificial base Us
<220> FEATURE:
<221> NAME/KEY: misc_feature
<222> LOCATION: (10)..(10)
<223> OTHER INFORMATION: n stands for artificial base Ds

<400> SEQUENCE: 27
aataanngcn tcctcaaagg tggtgacttc                               30
```

NUCLEIC ACID BASE ANALOGS WITH QUENCHING AND FLUORESCENT ACTIVITIES AND APPLICATIONS THEREOF

This application is the National Stage under 35 U.S.C. §371 of International Application PCT/JP2011/060343 filed on Apr. 21, 2011, which claims priority under 35 U.S.C. §119(a)-(d) of Application Number 2010-098319 filed in Japan on Apr. 21, 2010.

TECHNICAL FIELD

The present application claims priority to Japanese Patent Application No. 2010-098319 filed in the Japan Patent Office on Apr. 21, 2010, and the entire content of which are incorporated herein by reference.

The present invention relates to nucleic acid base analogs with quenching and fluorescent activities and relates to their application.

Specifically, the present invention relates to the discovery of functions as quenching molecules or nucleic acid base analogs of 2-nitropyrrole, 1- or 4-position modifications thereof, and nucleoside derivatives thereof and relates to use thereof. The invention can be used in a variety of detection and diagnosis, such as visualization of PCR products.

BACKGROUND ART

Technologies of expanding genetic information of DNA through production of novel artificial base pairs have two potential application fields with high versatility, and artificial base pairs have been actively developed. One of the application fields is use of an artificial base pair functioning in replication, transcription, or translation for producing DNA, RNA, or protein having a novel structural component. The other of the application fields is use of an artificial base pair incorporated in a double-stranded nucleic acid, DNA or RNA, to increase the number of types of probe sequences composed of nucleic acid fragments, which can be used in a multiplex real-time PCR or DNA computer and further can be used as a novel codon or anticodon for introducing an artificial amino acid into a protein through translation.

Though a large number of fluorescent nucleic acid base analogs have been reported, no nucleic acid base analog showing a high quenching effect by the analog itself has been reported. Conventionally, quenching molecules such as a dabsyl group have been linked to nucleic acid bases via linkers. In this case, bases forming a base pair are not in complete contact with a fluorescent molecule lying near the bases; therefore the quenching effect is weak. Accordingly, the detection thereof needs an apparatus. Thus, prior to the present invention, no method could simply and efficiently detect a base pair using a quenching effect of a base.

CITATION LIST

Patent Literature

Patent Literature 1: WO2009/123216
Patent Literature 2: Japanese Patent Application No. 2009-232776 (filed on Oct. 6, 2009)
Patent Literature 3: Japanese Patent Laid-Open No. 2007-061087
Patent Literature 4: Japanese Patent Application No. 2009-232851 (filed on Oct. 6, 2009)

Non-Patent Literature

Non-Patent Literature 1: An efficient unnatural base pair for PCR amplification, I. Hirao, T. Mitsui, M. Kimoto, and S. Yokoyama, J. Am. Chem. Soc., 129, 15549-15555 (2007).
Non-Patent Literature 2: An unnatural base pair system for efficient PCR amplification and functionalization of DNA molecules, M. Kimoto, R. Kawai, T. Mitsui, S. Yokoyama, and I. Hirao, Nucleic Acids Res., 37, e14 (2009).
Non-Patent Literature 3: Characterization of fluorescent, unnatural base pairs, T. Mitsui, M. Kimoto, R. Kawai, S. Yokoyama, and I. Hirao, Tetrahedron, 63, 3528-3537 (2007).
Non-Patent Literature 4: Fluorescent probing for RNA molecules by an unnatural base-pair system, M. Kimoto, T. Mitsui, Y. Harada, A. Sato, S. Yokoyama, and I. Hirao, Nucleic Acids Res., 35, 5360-5369 (2007).
Non-Patent Literature 5: 3-Nitropyrrole and 5-nitroindole as universal bases in primers for DNA sequencing and PCR, D. Loakes, D. W. Brown, S. Linde, and F. Hill, Nucleic Acids Res., 23, 2361-2366 (1995).
Non-Patent Literature 6: An unnatural hydrophobic base pair system: site-specific incorporation of nucleotide analogs into DNA and RNA, I. Hirao, M. Kimoto, T. Mitsui, T. Fujiwara, R. Kawai, Sato, Y. Harada, and S. Yokoyama, Nature Methods, 3, 729-735 (2006).

SUMMARY OF INVENTION

Technical Problem

The present inventors have found a base having a quenching activity and have predicted that selective formation of a base pair of a fluorescent base and a quenching base can intensely quench the fluorescence of the artificial fluorescent base in the formed double-stranded DNA to accomplish detection technology allowing visual observation of, for example, DNA amplification in PCR or a molecular beacon. Thus, the inventors have achieved the present invention.

2-Nitropyrrole derivatives are bases represented by Pn or Px in artificial base pairs developed by the present inventors. Pn and Px form third nucleic base pairs (artificial base pairs: Ds-Pn and Ds-Px base pairs) with their complementary artificial base (Ds: 7-(2-thienyl)imidazo[4,5-b]pyridin-3-yl group) and can be introduced into specific sites in nucleic acid through replication and transcription. 2-Nitropyrrole also forms a base pair with a modified Ds, which is an artificial fluorescent base Dss (7-(2,2'-bithien-5-yl)imidazo[4,5-b]pyridine).

The present inventors have first revealed in the present invention that 2-nitropyrrole has a quenching activity. For example, it was revealed that formation of a base pair of Pn or Px and Dss in double-stranded DNA quenches the fluorescence of Dss by the quenching effect by 2-nitropyrrole. Though 3-nitropyrrole, which is similar to 2-nitropyrrole, is known as a universal base, the quenching activity thereof is low, unlike 2-nitropyrrole of the present invention.

In a double-stranded nucleic acid including a base pair of Dss and Pn (or Px), since fluorescent Dss is in contact with Pn (or Px) having a quenching activity, the fluorescence of Dss is efficiently quenched. In contrast, when the double-stranded structure is converted to single-stranded DNA, the DNA strand including Dss emits light. Such an artificial base pair has become available for the first time, and detection or diagnostic technology, such as a novel molecular beacon, using this property has become possible.

It was revealed that in a nucleoside or nucleotide derivative (Px derivative) of 2-nitropyrrole, linking of a fluorescent dye to the 4-position of 2-nitropyrrole via a linker decreases the fluorescence intensity by an interaction between the 2-nitropyrrole and the dye. It was also found that in a nucleotide derivative introduced into DNA or RNA, the dye moiety interacting with 2-nitropyrrole protrudes to the outside of the DNA or RNA fragment to show the original fluorescence intensity. In addition, the substrate (nucleoside triphosphate) of this Px derivative is complementary to an artificial base Ds in a template and can be introduced into DNA through replication. This technology can be used in detective or diagnostic technology such as real-time PCR utilizing these characteristics in a fluorescence change of the Px derivative and site-specific incorporation into DNA through replication.

The present inventors have developed a novel method of visualizing DNA amplified through PCR by combining the Ds-Px base pair with an artificial fluorescent base (s) developed also by the inventors. The visualized PCR allows the amplified DNA to be identified with the naked eye, which can be applied to rapid and simple PCR diagnosis at clinical sites, which cannot be achieved by conventional real-time PCR, and paved the way for a companion diagnostic agent aimed for a personalized medicine. Detection of a specific DNA sequence by this technology is not limited to medical treatment and can be applied to, for example, the quality control of fermented food such as beer (through detection of genetic mutation in yeast) and the distribution management of import foodstuffs (through determination of authenticity of food genes).

As described above, the present invention includes, but not limited to, the following embodiments.

Embodiment 1

A quencher having a 2-nitropyrrole structure represented by Formula I:

[Formula 1]

Formula I (in Formula I, $R_1$ and $R_2$ are groups independently selected from the group consisting of:
ribose and deoxyribose;
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocylic rings containing nitrogen or sulfur, and one or more aromatic rings;
sugars, sugar chains, amino acids, and peptides; and
fluorescent molecules linked via linkers).

Embodiment 2

The quencher according to Embodiment 1, wherein $R_1$ in Formula I is ribose or deoxyribose.

Embodiment 3

A method of detecting formation of an artificial base pair, characterized in that the method uses either or both of:
1) a nucleoside or nucleotide having an artificial quenching base, represented by Formula II:

[Formula 2]

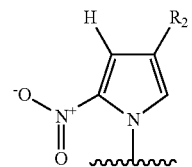

Formula II (in Formula II, $R_2$ is a group selected from the group consisting of:
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocylic rings containing nitrogen or sulfur, and one or more aromatic rings;
sugars, sugar chains, amino acids, and peptides; and
fluorescent molecules linked via linkers); or/and
2) a nucleoside or nucleotide having a modified natural base, artificial base, or base analog having a self-quenching activity that can function as a donor in, for example, fluorescence resonance energy transfer (FRET) or static quenching.

Embodiment 4

A method of detecting formation of a base pair of artificial bases, the method comprising:
observing a decrease in fluorescence of an artificial fluorescent base caused by formation of a base pair with an artificial quenching base represented by Formula II:

[Formula 3]

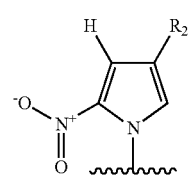

Formula II (in Formula II, $R_2$ is a group selected from the group consisting of:
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocylic rings containing nitrogen or sulfur, and one or more aromatic rings;
sugars, sugar chains, amino acids, and peptides; and
fluorescent molecules linked via linkers).

Embodiment 5

A method of detecting formation of a base pair of artificial bases, the method comprising:

observing a decrease in fluorescence of an artificial fluorescent base, wherein the decrease in fluorescence of an artificial fluorescent base is caused by formation of a base pair of an artificial fluorescent base and a quenching base, wherein the artificial fluorescent base is selected from the group consisting of:

(i) a 7-(2,2'-bithien-5-yl)imidazo[4,5-b]pyridin-3-yl group (Dss);
(ii) a 7-(2,2',5',2''-terthien-5-yl)imidazo[4,5-b]pyridin-3-yl group (Dsss);
(iii) a 2-amino-6-(2,2'-bithien-5-yl)purin-9-yl group (ss);
(iv) a 2-amino-6-(2,2',5',2''-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 4-[5-(2-thienyl)thiazol-2-yl]pyrrolo[2,3-b]pyridin-1-yl group (Dvas); and the quenching base is represented by Formula III or IV:

[Formula 4]

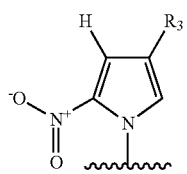

Formula III (in Formula III, $R_3$ is selected from —H, iodine, —$CH_3$, and:

[Formula 5]

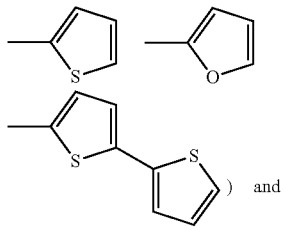) and

[Formula 6]

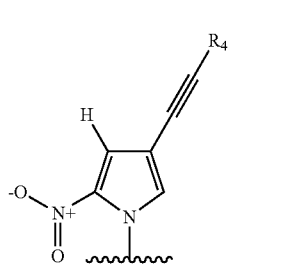

Formula IV (in Formula IV, $R_4$ is selected from —$CH_3$, —$CH_2$—$NH_2$, and:

[Formula 7]

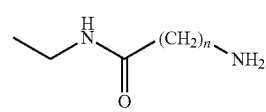

(wherein, n is an integer of 0 to 12)).

Embodiment 6

A kit used in a method of detecting formation of a base pair of artificial bases by observing a decrease in fluorescence of an artificial fluorescent base, the kit comprising:

a nucleic acid primer comprising a polynucleotide having a 7-(2,2'-bithien-5-yl)imidazo[4,5-b]pyridin-3-yl group (Dss) as a base; and a polynucleotide having a quenching base represented by Formula III or IV

[Formula 8]

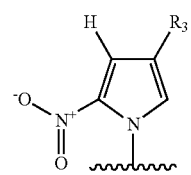

Formula III (in Formula III, $R_3$ is selected from —H, iodine, —$CH_3$, and:

[Formula 9]

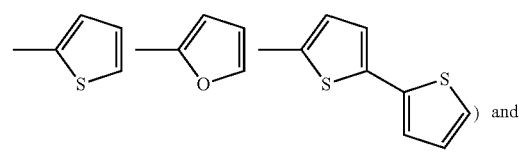 and

[Formula 10]

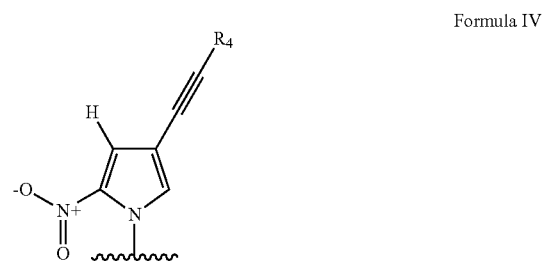

Formula IV (in Formula IV, $R_4$ is selected from —$CH_3$, —$CH_2$—$NH_2$, and:

[Formula 11]

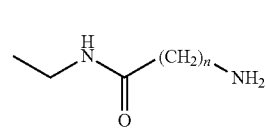

(wherein, n is an integer of 0 to 12)).

Embodiment 7

A method of detecting an artificial base pair, the method comprising:
observing a change in fluorescence intensity of a fluorescent molecule in an artificial quenching base represented by Formula V:

[Formula 12]

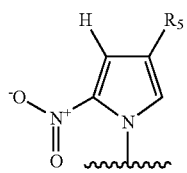

Formula V (in Formula V, $R_5$ is a fluorescent molecule linked via a linker) caused by formation of an artificial base pair of the artificial base represented by Formula V.

Embodiment 8

A method of detecting formation of a base pair of artificial bases, the method comprising:
observing a change in fluorescence intensity, wherein
the change is an increase in fluorescence intensity of a fluorescent molecule of a base represented by Formula VI:

[Formula 13]

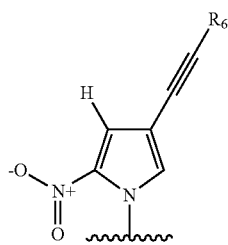

Formula VI (in Formula VI, $R_6$ is a fluorescent molecule linked directly or via a linker) caused by formation of an artificial base pair of the base represented by Formula VI and a 7-(2-thienyl)imidazo[4,5-b]pyridin-3-yl group (Ds).

Embodiment 9

The method according to Embodiment 7 or 8, wherein the fluorescent molecule is selected from the group consisting of: indocarbocyanine (Cy3), indodicarbocyanine (Cy5), 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX).

Embodiment 10

A kit used in a method of detecting formation of a base pair of artificial bases by observing a change in fluorescence intensity, the kit comprising:
a nucleic acid primer comprising a polynucleoside having a 7-(2-thienyl)imidazo[4,5-b]pyridin-3-yl group (Ds) as a base; and
a polynucleotide having a base represented by Formula VI:

[Formula 14]

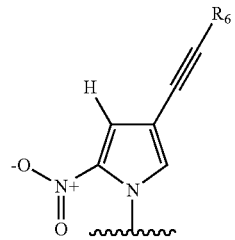

Formula VI (in Formula VI, $R_6$ is a fluorescent molecule linked directly or via a linker).

Embodiment 11

A method of detecting formation of an artificial base pair, the method using a nucleic acid comprising a polynucleoside having a modified natural base, artificial base, or base analog having a self-quenching activity that can function as a donor in, for example, fluorescence resonance energy transfer (FRET) or static quenching, wherein
formation of an artificial base pair of an artificial base (a first artificial base) and an artificial base having a fluorescent molecule (a second artificial base) in the nucleic acid causes a change in fluorescence spectrum caused by fluorescence resonance energy transfer from the polynucleotide having the modified natural base, artificial base, or base analog to the fluorescent molecule of the second artificial base or static quenching to allow detection of the formation of the artificial base pair.

Embodiment 12

A method of detecting formation of a base pair of artificial bases by observing a change in fluorescence spectrum caused by, for example, fluorescence resonance energy transfer or static quenching, wherein
formation of a base pair of a 7-(2,2'-bithien-5-yl)imidazo[4,5-b]pyridin-3-yl group (Dss) and a base represented by Formula VI:

[Formula 15]

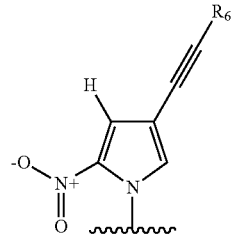

Formula VI (in Formula VI, $R_6$ is a fluorescent molecule linked directly or via a linker) causes fluorescence resonance energy transfer from the Dss to the fluorescent molecule in the base represented by Formula VI or static quenching by excitation with ultraviolet light having a wavelength of 240 to 410 nm and thereby a change in fluorescence spectrum to allow detection of the formation of the artificial base pair.

Embodiment 13

A method of detecting formation of a base pair of artificial bases, the method comprising:
observing a change in fluorescence spectrum caused by, for example, fluorescence resonance energy transfer or static quenching, wherein
the change in fluorescence spectrum is caused by formation of a base pair of a 7-(2-thienyl)imidazo[4,5-b]pyridin-3-yl group (Ds) and a base represented by Formula VI:

[Formula 16]

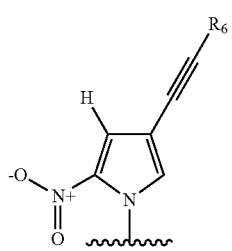

Formula VI (in Formula VI, $R_6$ is a fluorescent molecule linked directly or via a linker) to cause fluorescence resonance energy transfer from at least one 2-amino-6-(2-thienyl)purin-9-yl group (s) to the fluorescent molecule in the base represented by Formula VI or static quenching by excitation with ultraviolet light having a wavelength of 240 to 390 nm, and thereby the change allows the detection of the formation of the artificial base pair, wherein
at least one polynucleotide having a 2-amino-6-(2-thienyl)purin-9-yl group (s) as a base is present in the same nucleic acid strand that comprises a polynucleoside having Ds as a base.

Embodiment 14

A method of detecting formation of a base pair of artificial bases, the method comprising:
observing a change in fluorescence spectrum caused by, for example, fluorescence resonance energy transfer or static quenching, wherein
the change in fluorescence spectrum is caused by formation of a base pair of a 7-(2-thienyl)imidazo[4,5-b]pyridin-3-yl group (Ds) and a base represented by Formula VI:

[Formula 17]

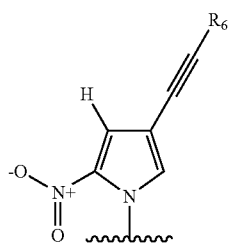

Formula VI (in Formula VI, $R_6$ is a fluorescent molecule linked directly or via a linker) to cause fluorescence resonance energy transfer from at least one 2-amino-6-(2-thienyl)purin-9-yl group (s) to the fluorescent molecule in the base represented by Formula VI or static quenching by excitation with ultraviolet light having a wavelength of 350 to 390 nm, and thereby the change allows the detection of the formation of the artificial base pair, wherein
at least one polynucleotide having a natural base to which at least one 2-amino-6-(2-thienyl)purin-9-yl group (s) linked is present in the same nucleic acid strand that comprises a polynucleoside having Ds as a base

Embodiment 15

A method of detecting formation of a base pair of artificial bases, the method comprising:
observing a change in fluorescence spectrum caused by, for example, fluorescence resonance energy transfer or static quenching, wherein
the change in fluorescence spectrum is caused by formation of a base pair of a 7-(2-thienyl)imidazo[4,5-b]pyridin-3-yl group (Ds) and a base represented by Formula VI:

[Formula 18]

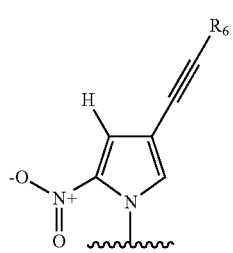

Formula VI (in Formula VI, $R_6$ is a fluorescent molecule linked directly or via a linker) to cause fluorescence resonance energy transfer from a 7-(2,2'-bithien-5-yl)imidazo[4,5-b]pyridin-3-yl group (Dss) to the fluorescent molecule in the base represented by Formula VI or static quenching by excitation with ultraviolet light having a wavelength of 240 to 410 nm, and thereby the change allows the detection of the formation of the artificial base pair, wherein
at least one polynucleotide having a natural base to which at least one 7-(2,2'-bithien-5-yl)imidazo[4,5-b]pyridin-3-yl group (Dss) linked is present in the same nucleic acid strand that comprise a polynucleoside having Ds as a base.

Embodiment 16

The method according to any one of Embodiments 11 to 15, wherein the fluorescent molecule is selected from the group consisting of:
indocarbocyanine (Cy3), indodicarbocyanine (Cy5), 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX).

Embodiment 17

The method according to any one of Embodiments 12 to 15, wherein the substituent $R_6$ in the base represented by Formula VI has the following structure:

11

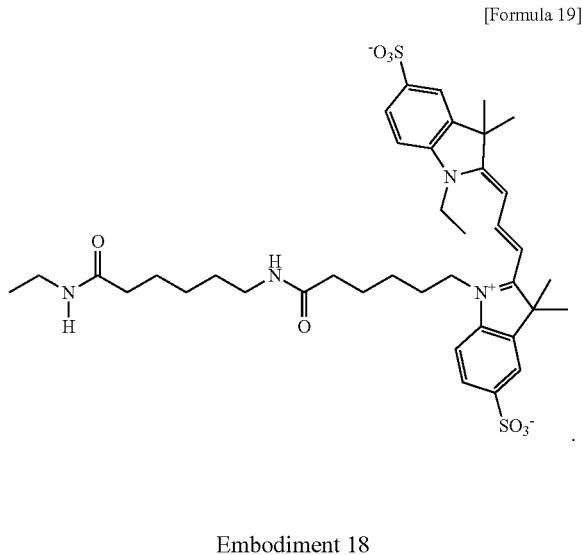

[Formula 19]

Embodiment 18

The method according to any one of Embodiments 11 to 17, wherein the change in fluorescent spectrum is observed with the naked eye.

Embodiment 19

The method according to any one of Embodiments 11 to 18, wherein the base pair of the nucleic acid is formed in the process of transcription, reverse transcription, replication, or translation.

Embodiment 20

A kit used in a method of detecting formation of a base pair of artificial bases on the basis of a change in fluorescence spectrum caused by, for example, fluorescence resonance energy transfer or static quenching, the kit comprising:

one nucleic acid primer selected from the group consisting of the following i) to iv):

i) a nucleic acid primer comprising a polynucleotide having a 7-(2,2'-bithien-5-yl)imidazo[4,5-b]pyridin-3-yl group (Dss) as a base;

ii) a nucleic acid primer comprising a polynucleoside having a 7-(2-thienyl)imidazo[4,5-b]pyridin-3-yl group (Ds) as a base and at least one polynucleotide having a 2-amino-6-(2-thienyl)-9H-purin-9-yl group (s) as a base;

iii) a nucleic acid primer comprising a polynucleoside having a 7-(2-thienyl)imidazo[4,5-b]pyridin-3-yl group (Ds) as base and at least one polynucleotide having a natural base to which a 2-amino-6-(2-thienyl)-9H-purin-9-yl group (s) is linked; and iv) a nucleic acid primer comprising a polynucleoside having a 7-(2-thienyl)imidazo[4,5-b]pyridin-3-yl group (Ds) as a base and a polynucleotide having a natural base to which a 7-(2,2'-bithien-5-yl)imidazo[4,5-b]pyridin-3-yl group (Dss) is linked, and

12 the kit comprising:
a polynucleotide having a base represented by Formula VI:

Formula VI

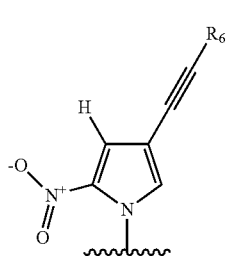

[Formula 20]

(in Formula VI, $R_6$ is a fluorescent molecule linked directly or via a linker) as a base.

Solution to Problem

I. Quencher
1. Structure of Quencher

The present invention provides a novel quencher. The quencher of the present invention has a 2-nitropyrrole structure represented by Formula I:

Formula I

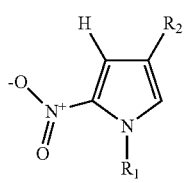

[Formula 21]

(in Formula I, $R_1$ and $R_2$ are groups independently selected from the group consisting of:
ribose and deoxyribose;
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocyclic rings containing nitrogen or sulfur, and one or more aromatic rings;
sugars, sugar chains, amino acids, and peptides; and
fluorescent molecules linked via linkers).

The present invention is based on the finding that the 2-nitropyrrole structure has a quenching effect. Accordingly, $R_1$ and $R_2$ are not particularly limited, and can be each any group appropriately selected. $R_1$ and $R_2$ are each independently selected.

i) Ribose and Deoxyribose $R_1$ and/or $R_2$ is preferably ribose or deoxyribose. Preferably, $R_1$ is ribose or deoxyribose.

"Ribose" is one of the pentoses and is "(3R,4S,5R)-5-(hydroxymethyl)tetrahydrofuran-2,3,4-triol" in the IUPAC nomenclature.

"Deoxyribose" is one of the pentoses having an aldehyde group and is "(2R,4S,5R)-5-(hydroxymethyl)tetrahydrofuran-2,4-diol" in the IUPAC nomenclature.

The quencher of the present invention preferably exhibits a quenching effect, that is, when the quencher forms an artificial base pair as a quenching base in a polynucleoside or polynucleotide, quenches the fluorescence of a fluorescent base that forms an artificial base pair with the quenching base or the fluorescence of a fluorescent base present near the quenching base. Alternatively, the quencher exhibits a quenching effect, that is, when the quencher forms an artificial base pair as a quenching base, quenches the fluorescence of a fluorescent material linking to the base that forms the artificial base pair with the quenching base or linking to a base present near the quenching base.

ii) Hydrogen, Hydroxyl and SH Groups, and Halogens

Types of halogen are not particularly limited. Preferably, a halogen selected from the group consisting of fluorine, bromine, and iodine is used.

iii) Substituted or Unsubstituted Alkyl, Alkenyl, and Alkynyl Groups Each Having 2 to 10 Carbon Atoms The alkyl, alkenyl, or alkynyl group having 2 to 10 carbon atoms may be linear or branched and is not particularly limited. Preferable examples include methyl, ethyl, propynyl, ethylene, and ethynyl groups. These groups may be substituted or not substituted. Any substituent can be introduced without limitation, and is preferably selected from the group consisting of amino, hydroxyl, SH, carboxyl, and nitro groups and halogens.

iv) One or More Five-Membered Heterocyclic Rings, One or More Six-Membered Heterocyclic Rings, and One or More Fused Heterocyclic Rings, these Heterocylic Rings Containing Nitrogen or Sulfur, and One or More Aromatic Rings $R_1$ and/or $R_2$ may each be one or more fused heterocyclic rings. The heterocyclic ring is a five-membered heterocyclic ring selected from, for example, thienyl, thiazolyl, imidazolyl, and furanyl groups and derivatives thereof. Preferably, the one or more five-membered heterocyclic ring is a group selected from the group consisting of 2-thienyl, 2-thiazolyl, 2-imidazolyl, 2,2'-bithien-5-yl, 2-(2-thiazolyl)thien-5-yl, 5-(2-thienyl)thiazol-2-yl, and 2,2',5',2''-terthien-5-yl groups.

Examples of the six-membered heterocyclic ring include pyranyl, pyridyl, and pyrimidyl groups. Examples of the fused heterocyclic ring include purine, 1-deazapurine, and quinoline.

Examples of the aromatic ring include phenyl and naphthyl groups.

The numbers of the heterocyclic rings, fused heterocyclic rings, and aromatic rings are not particularly limited, but are each preferably one to three, more preferably one or two.

v) Sugars, Sugar Chains, Amino Acids, and Peptides

Any sugar can be introduced without limitation. Examples of the sugar include glucose, arabinose, and furanose. Ribose and deoxyribose are also sugars.

Any sugar chain can be introduced without limitation. Examples of the sugar chain include sucrose and lactose.

Any amino acid can be introduced without limitation. Examples of the amino acid include glycine, alanine, and phenylalanine.

Any peptide can be introduced without limitation. Preferably, the peptide is a polypeptide composed of about two to ten amino acid residues. Preferred examples of the peptide include phenylalanine-glycine. Further, examples of the peptide include non-natural peptides such as peptide nucleic acids.

vi) Fluorescent Molecule Linked Via a Linker

Any linker can be used and can be appropriately selected by a person skilled in the art. The linker is preferably selected from, but not limited to, the group consisting of linkers represented by Formula VII or VIII:

VII

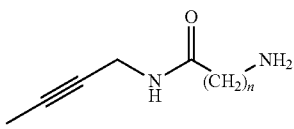

[Formula 22]

(in Formula VII, n is an integer of 1 to 12), and

VIII

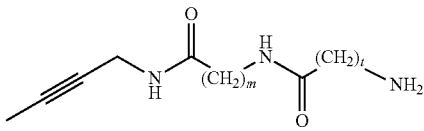

[Formula 23]

(in Formula VIII, m and l are each independently an integer of 1 to 12).

In Formulae VII and VIII, n, m, and l are each preferably an integer of 1 to 7 and more preferably 5.

Any fluorescent molecule can be used. Preferably, the fluorescent molecule is selected from the group consisting of indocarbocyanine (Cy3), indodicarbocyanine (Cy5), 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), and 6-carboxy-X-rhodamine (6-ROX). More preferably, the fluorescent molecule is indocarbocyanine (Cy3).

2. Quenchable Fluorescent Material

The fluorescent material quenchable by the quenching effect of the quencher having a 2-nitropyrrole structure represented by Formula I of the present invention is not particularly limited.

Examples of the fluorescent material include artificial fluorescent bases and fluorescent molecules such as fluorescent dyes.

The 2-nitropyrrole structure represented by Formula I preferably forms a pair with the following bases (Japanese Patent Application No. 2009-232851):

7-(2-thienyl)imidazo[4,5-b]pyridin-3-yl group (Ds);
7-(2,2'-bithien-5-yl)imidazo[4,5-b]pyridin-3-yl group (Dss);
7-(2,2',5',2''-terthien-5-yl)imidazo[4,5-b]pyridin-3-yl group (Dsss);
2-amino-6-(2-thienyl)purin-9-yl group (s);
2-amino-6-(2,2'-bithien-5-yl)purin-9-yl group (ss);
2-amino-6-(2,2',5',2''-terthien-5-yl)purin-9-yl group (sss);
4-(2-thienyl)-pyrrolo[2,3-b]pyridin-1-yl group (dDsa);
4-(2,2'-bithien-5-yl)-pyrrolo[2,3-b]pyridin-1-yl group (Dsas);
4-[2-(2-thiazolyl)thien-5-yl]pyrrolo[2,3-b]pyridin-1-yl group (Dsav);
4-(2-thiazolyl)-pyrrolo[2,3-b]pyridin-1-yl group (dDva);
4-[5-(2-thienyl)thiazol-2-yl]pyrrolo[2,3-b]pyridin-1-yl group (Dvas); and
4-(2-imidazolyl)-pyrrolo[2,3-b]pyridin-1-yl group (dDia).

Among the bases above, Dss, Dsss, ss, sss, Dsas, Dsav, and Dvas are fluorescent bases. The fluorescence intensity of these bases is decreased or quenched by formation of a base pair with the quencher represented by Formula I of the present invention.

Even if a fluorescent material does not directly form a base pair with the quencher represented by Formula I, the material is affected by the quencher of the present invention when the material is present near an artificial base that forms a base pair with the quencher of Formula I. For example, when an artificial fluorescent base is present near an artificial base (e.g., s), for example, so as to be adjacent to each other in a single-stranded, double-stranded, or triple-stranded nucleic acid or when a fluorescent molecule is linked to the artificial base, formation of a base pair of the quencher of Formula I and the artificial base brings the fluorescent material near the quencher of the present invention. As a result, the fluorescence is affected by quenching.

In addition to the above-mentioned artificial bases that form base pairs with the quencher represented by Formula I, for example, 2-amino purine and ethenoadenosine are known as fluorescent nucleic acid bases.

II. Method of Detecting Formation of Artificial Base Pair

The present invention also provides a method of detecting an artificial base pair. The method of the present invention characterized in that it uses either or both of:
1) a nucleoside or nucleotide having an artificial quenching base represented by Formula II:

Formula II

[Formula 24]

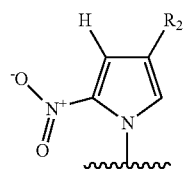

(in Formula II, $R_2$ is a group selected from the group consisting of:
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocyclic rings containing nitrogen or sulfur, and one or more aromatic rings;
sugars, sugar chains, amino acids, and peptides; and
fluorescent molecules linked via linkers) or/and
2) a nucleoside or nucleotide including a modified natural base, artificial base, or base analog having a self-quenching activity that can function as a donor in, for example, fluorescence resonance energy transfer (FRET) or static quenching.

Use of Artificial Base of Formula II

The nitrogen atom of a pyrrole ring of the artificial quenching base represented by Formula II of the present invention binds to ribose or deoxyribose to form a nucleoside or nucleotide. The artificial base represented by Formula II of the present invention forms an artificial base pair with an artificial base such as Ds, Dss, Dsss, s, ss, sss, dDsa, Dsas, Dsav, dDva, Dvas, or dDia (Japanese Patent Application No. 2009-232851). Formation of a base pair of the artificial quenching base of Formula II and the artificial base modifies the fluorescence intensity of the artificial fluorescent base forming the base pair or of the fluorescent base or fluorescent molecule present near the base pair or quenches such fluorescence. The method of the present invention detects the formation of the artificial base pair using such a change in fluorescence.

In particular, among the artificial bases, Dss, Dsss, ss, sss, Dsas, Dsav, and Dvas are fluorescent bases, and the fluorescence intensity of these bases is decreased or quenched by formation of a base pair with the compound represented by Formula II.

Alternatively, linking of a fluorescent molecule to the artificial quenching base of the present invention decreases the fluorescence intensity of the fluorescent molecule by the quenching effect of the artificial quenching base of the present invention. This is believed that stacking of the fluorescent molecule and the artificial quenching base in a solution causes efficient quenching. The artificial quenching base linked to the fluorescent molecule forms an artificial base pair with an artificial base and is incorporated into a nucleic acid to release the stacking between the fluorescent molecule and the artificial quenching base. As a result, the fluorescence intensity of the fluorescent dye increases. It is possible to detect formation of an artificial base pair using this property.

Use of Fluorescence Resonance Energy Transfer (FRET) and Static Quenching

The present invention encompasses a method of detecting an artificial base pair using a nucleoside or nucleotide having a modified natural base, artificial base, or base analog having a self-quenching activity that can function as a donor in, for example, fluorescence resonance energy transfer (FRET) or static quenching.

The term "fluorescence resonance energy transfer (FRET)" means a phenomenon that excitation energy transfers from a fluorescent molecule to another molecule by resonance. The molecule that gives energy is called donor, and the molecule that receives the energy is called acceptor. When FRET occurs, the donor that has lost energy returns to the ground state, while the acceptor that has received the energy becomes the excited state. Accordingly, the fluorescence intensity of the donor decreases, and fluorescence is observed when the acceptor is a fluorescent molecule. If the acceptor is a quenching molecule, FRET makes the fluorescence that has been observed when the donor is present alone not to be observed. General methods of detecting protein or nucleic acid using FRET are known.

In order to cause FRET, the following three conditions must be satisfied: i) The fluorescence spectrum of the donor overlaps with the spectrum of the acceptor. A larger overlapping region is preferred, but it is not necessarily required to completely overlap with each other. ii) The physical distance between the donor and the acceptor is short. The distance that causes FRET at a probability of 50% is believed to be 3 to 6 nm. The efficiency of FRET sensitively varies depending on a change in this distance. iii) Relative directions of the donor and the acceptor are appropriate.

The method of the present invention utilizes a modified natural base, artificial base, or base analog having a self-quenching activity that can function as a donor in, for example, fluorescence resonance energy transfer (FRET). The process of quenching encompasses static quenching caused by formation of an excited dimer such as an excimer, in addition to FRET. When formation of an artificial base pair brings a modified natural base, artificial base, or base analog having a self-quenching activity near an acceptor, energy is donated from such a donor to the acceptor by exciting the donor with energy having a specific wavelength. As a result, the acceptor emits fluorescence with energy having a wavelength at which the acceptor does not inherently emit fluorescence.

The "artificial base having a self-quenching activity" is a base adjacent to, for example, one or more "s"'s. Examples thereof include, but not limited to, two or more s, ss, Dss, and Dsss adjacent to each other in a nucleic acid.

Preferably, the artificial base having a self-quenching activity is two or more "s"'s adjacent to each other in a nucleic acid. Non-limiting examples of the "modified natural base having a self-quenching activity" include natural bases to which one or more artificial bases (e.g., s) having the self-quenching activity linked (e.g., s-linked uracil, two "s"'s-linked cytosine, and Dss-linked uracil). Examples of the "base analog having a self-quenching activity" include size-expanded base analog dimers and 2-amino purine dimers.

The artificial base pair that is detected here is preferably a base pair of an artificial quenching base represented by Formula II and an artificial base complementary thereto, but is not necessarily limited thereto. As long as the method utilizes a nucleoside or nucleotide having a modified natural base, artificial base, or base analog having a self-quenching activity that can function as a donor in fluorescence resonance energy transfer (FRET) or static quenching, other known artificial base pairs are also included in the scope of the present invention. For example, artificial base pairs such as an s-y base pair (s: 2-amino-6-thienylpurine, y: pyridin-2-on), v-y base pair (v: 2-amino-6-thiazolylpurine), s-Pa base pair (Pa: pyrrole-2-carbaldehyde), Ds-Pa base pair (Ds: 7-(2-thienyl)imidazo[4,5-b]pyridine), Pa-Q base pair (Q: 9-methyl imidazo[(4,5)-b]pyridine), isoG-isoC, 5SICS-MMO2, and 5NaM can be detected by the method utilizing FRET of the present invention.

BRIEF DESCRIPTION OF DRAWINGS

The patent or application file contains at least one drawing executed in color. Copies of this patent or patent application publication with color drawing(s) will be provided by the office upon request and payment of the necessary fee.

As shown in FIG. 8, the fluorescence intensity of Dss was quenched by Pn to about one-fifth.

FIG. 9A shows a change in fluorescence intensity of deoxyribonucleoside triphosphate (dDssTP, 5 μM) as an artificial fluorescent base Dss depending on the concentration of deoxyribonucleoside triphosphate (dPnTP) as Pn, and FIG. 9B shows the results of comparison of quenching effects of dPnTP and triphosphate of a natural base against Dss, shown as steady-state stern-volmer plots of quenching of fluorescent base dDssTP (5 μM) by deoxyribonucleoside triphosphates of Pn and the natural base. The fluorescence intensity after excitation with light of 370 nm at 20° C. was measured in a solution of 100 mM NaCl, 10 mM sodium phosphate (pH 7.0), and 0.1 mM EDTA, and stern-volmer constant ($K_{sv}$) was calculated by the following equation:

$$F_0/F_1 = 1 + K_{SV}[Q]$$  Stern-Volmer equation:

($F_0$ and $F_1$ respectively represent fluorescence intensities in the presence ($F_1$) and absence ($F_0$) of a quencher; and [Q] represents the concentration of the quencher). It is shown that the quenching activity of Pn is a higher than that of a guanine base, which is known to have a quenching activity (FIG. 9B).

Figure 10:
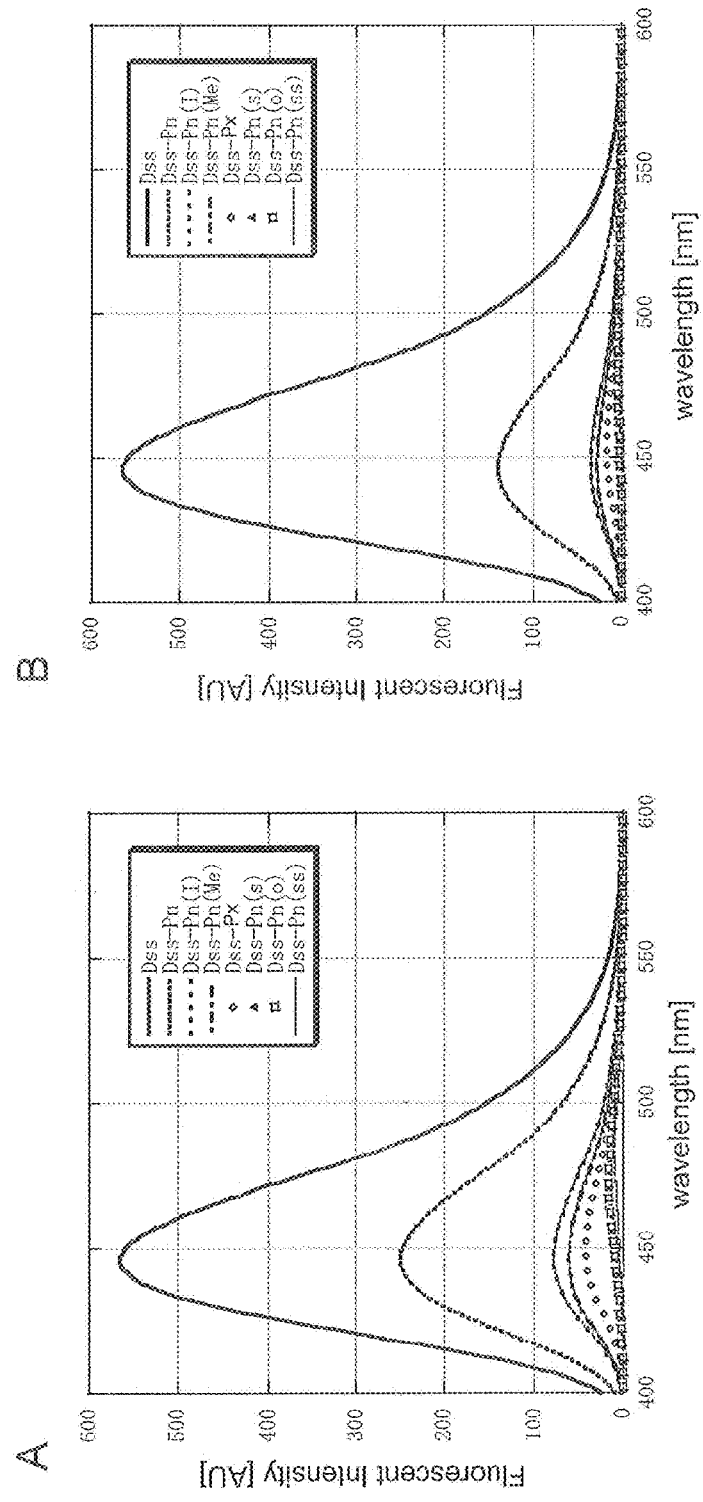

FIG. 10 shows Dss-fluorescence-quenching characteristics of Pn, various derivatives thereof (FIGS. 2 and 3), and Px. Specifically, the fluorescence intensity by excitation with light of 385 nm at 25° C. was measured in ethanol, and changes in fluorescence intensity of dDss (5 μM) were investigated in the presence of deoxyribonucleoside of any derivative of Pn or Px (A: 2.5 mM, B: 5 mM). Each derivative exhibited higher quenching characteristics than that of Pn.

Figure 11:
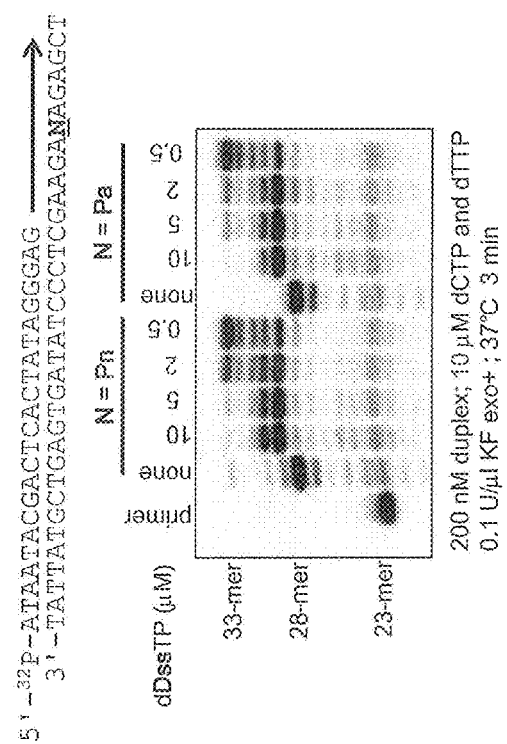

FIG. 11 shows the results of investigation on the primer extension reaction by a Klenow fragment of a DNA polymerase I derived from *Escherichia coli* using a template DNA comprising Pn and dDssTP. dDssTP in each concentration was added to 200 nM DNA as a template, 10 μM of dCTP and dTTP, and 0.1 U/μL of a Klenow fragment. The mixture was subjected to a reaction at 37° C. for 3 minutes, followed by modified gel electrophoretic analysis. Since the reaction solution did not contain dATP and dGTP, the extension reaction stopped before C in the template to give a 33-mer product. FIG. 11 shows that dDssTP complemented Pn in the template and was incorporated into the complementary strand DNA. It is known that dDssTP is incorporated by Pa in a template (J. Am. Chem. Soc., 132: 4988-4989, 2010). The Dss-incorporating efficiency of Pn is higher than that of Pa. Though the extension reaction after incorporation of Dss by Pn or Pa is inhibited by increasing the concentration of dDssTP, the primer extension reaction efficiently proceeded by reducing the concentration of dDssTP.

Figure 12:
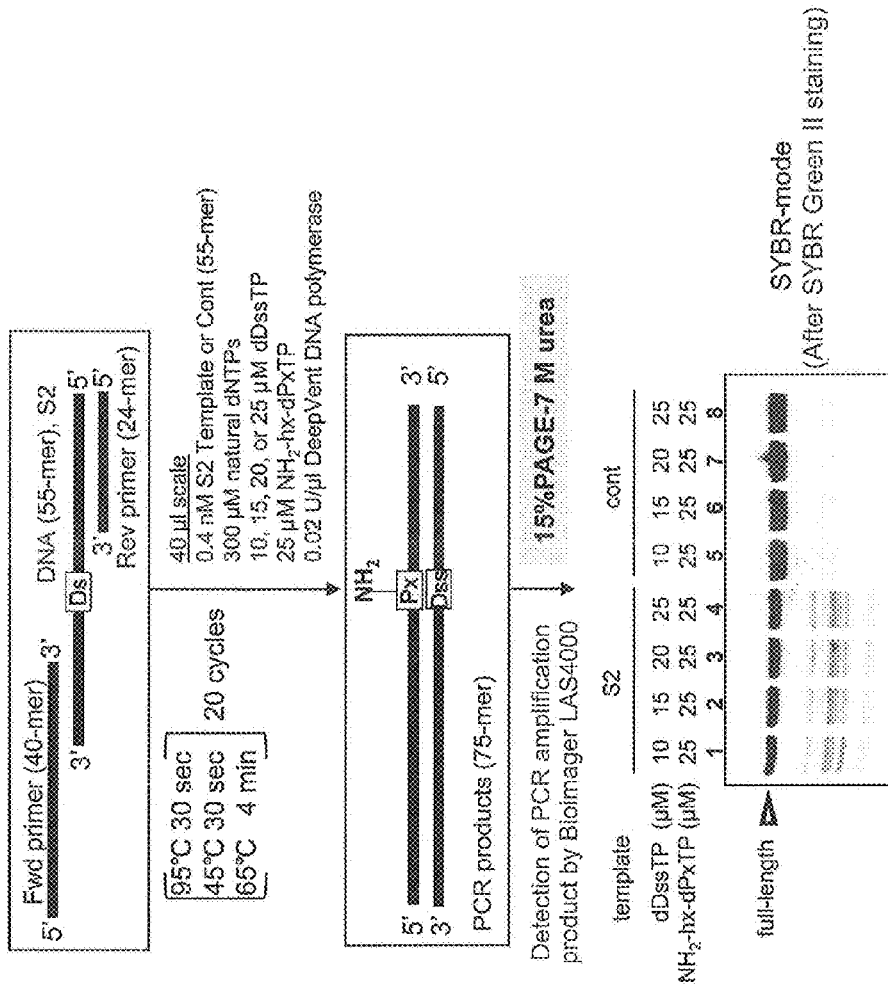

FIG. 12 shows the results of investigation on PCR amplification of a DNA comprising Ds using a Dss-Px base pair. A DNA (55-mer) comprising Ds was subjected to 20 cycles of PCR amplification using dDssTP, $NH_2$-hx-dPxTP, and natural base substrates. After modified gel electrophoresis, products were analyzed by SYBR Green II staining. The results indicate those of PCR using a template DNA (55-mer, S2) comprising Ds and adding dDssTP and $NH_2$-hx-dPxTP to the natural base substrates (dNTPs). It was revealed that the template DNA-S2 comprising an artificial base was also amplified as in a template DNA composed of natural bases only. The Dss-Pn and Dss-Px base pairs also efficiently function in PCR.

Figure 13:
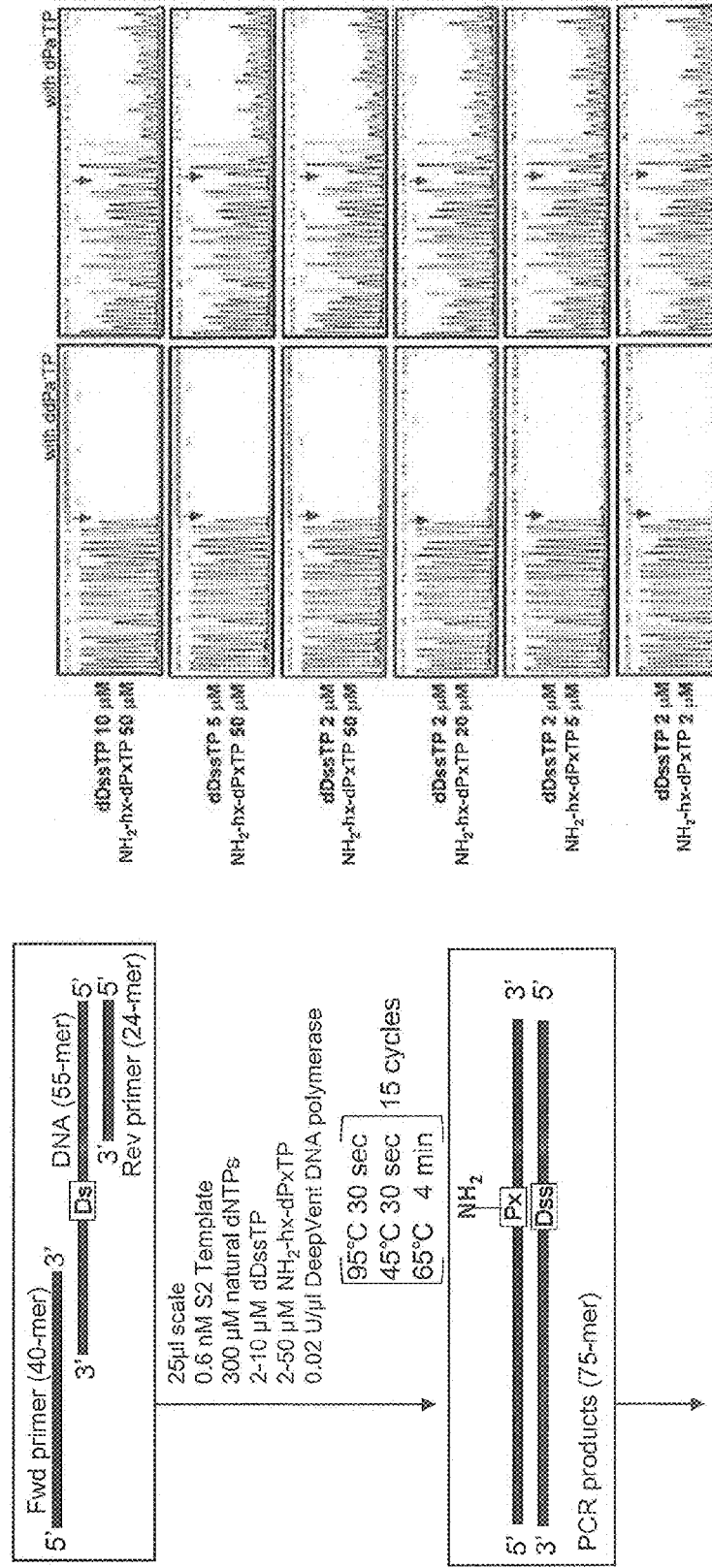

FIG. 13 shows the results of sequence determination of DNA after PCR amplification using the Dss-Px base pair. A DNA (55-mer) comprising Ds was subjected to 15 cycles of PCR amplification using dDssTP, $NH_2$-hx-dPxTP, and natural base substrates, and the sequence of the amplified product was determined by a known method. It was revealed that 99% or more of Dss and $NH_2$-hx-Px were maintained in the amplified DNA. This sequence determination was performed by the method developed by the present inventors (An unnatural hydrophobic base pair system: site-specific incorporation of nucleotide analogs into DNA and RNA. I. Hirao, M. Kimoto, T. Mitsui, T. Fujiwara, R. Kawai, A. Sato, Y. Harada, and S. Yokoyama, Nature Methods, 3, 729-735 (2006); An unnatural base pair system for efficient PCR amplification and functionalization of DNA molecules. M. Kimoto, R. Kawai, T. Mitsui, S. Yokoyama, and I. Hirao, Nucleic Acids Res., 37, e14 (2009)).

Figure 14:
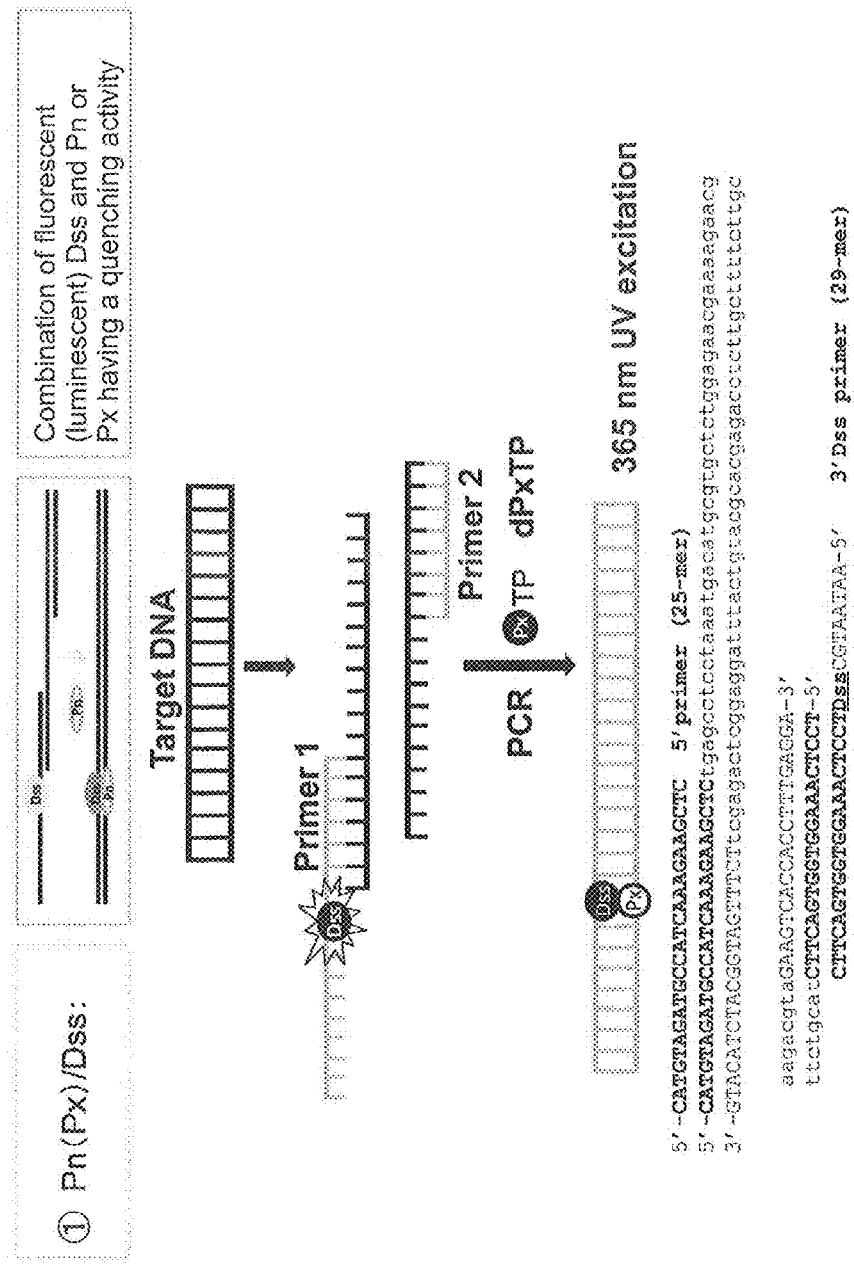

FIG. 14 schematically illustrates the principle of a real-time PCR using a Dss-Px base pair. Dss was introduced in a primer, and PCR was performed using the primer and dPnTP or dPxTP. Pn or Px complements Dss to be incorporated into a complementary strand to quench the fluorescence of the Dss. This indicates possible application to real-time PCR.

Figure 15:
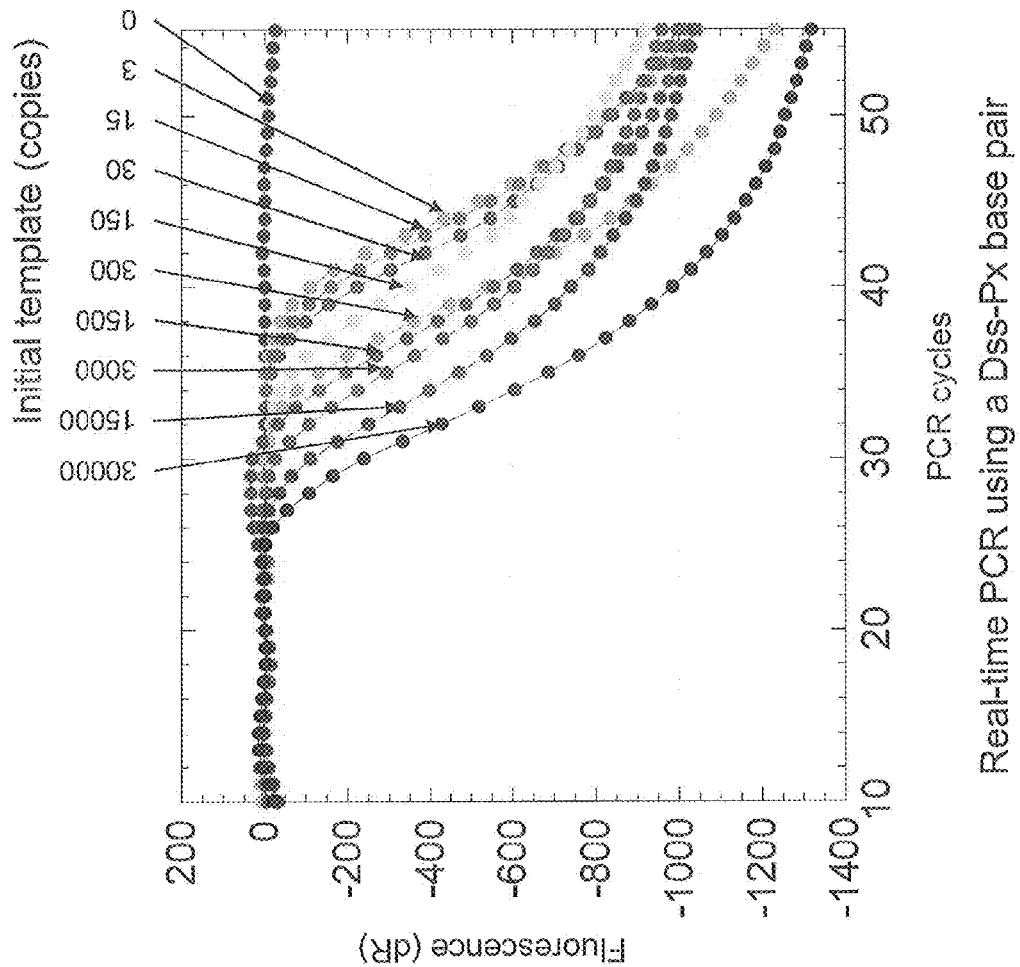

FIG. 15 shows the results of real-time PCR using a Dss-Px base pair. dPxTP was incorporated into a complementary strand of the primer comprising Dss shown in FIG. 14 to quench the fluorescence of the Dss. This is caused by formation of a Dss-Px base pair during PCR to quench the fluorescence of Dss and can be applied to real-time PCR.

Reaction Mixture Solution (25 µL Scale)
1× Titanium Taq PCR buffer,
1 µM 080731-5' primer 3 (SEQ ID NO: 15),
1 µM 090914a-Plexor-Dss1 (SEQ ID NO: 16),
2 µM dPxTP,
2 mM dNTPs,
1× Titanium Taq DNA polymerase,
2 aM (3 copies) to 2 fM (30000 copies) of template DNA, and
sterilized water to adjust the total volume to 25 µL.
PCR Conditions:
94° C. for 2 min and then (94° C. for 5 sec and then 68° C. for 40 sec)×55 cycles.

Figure 16:
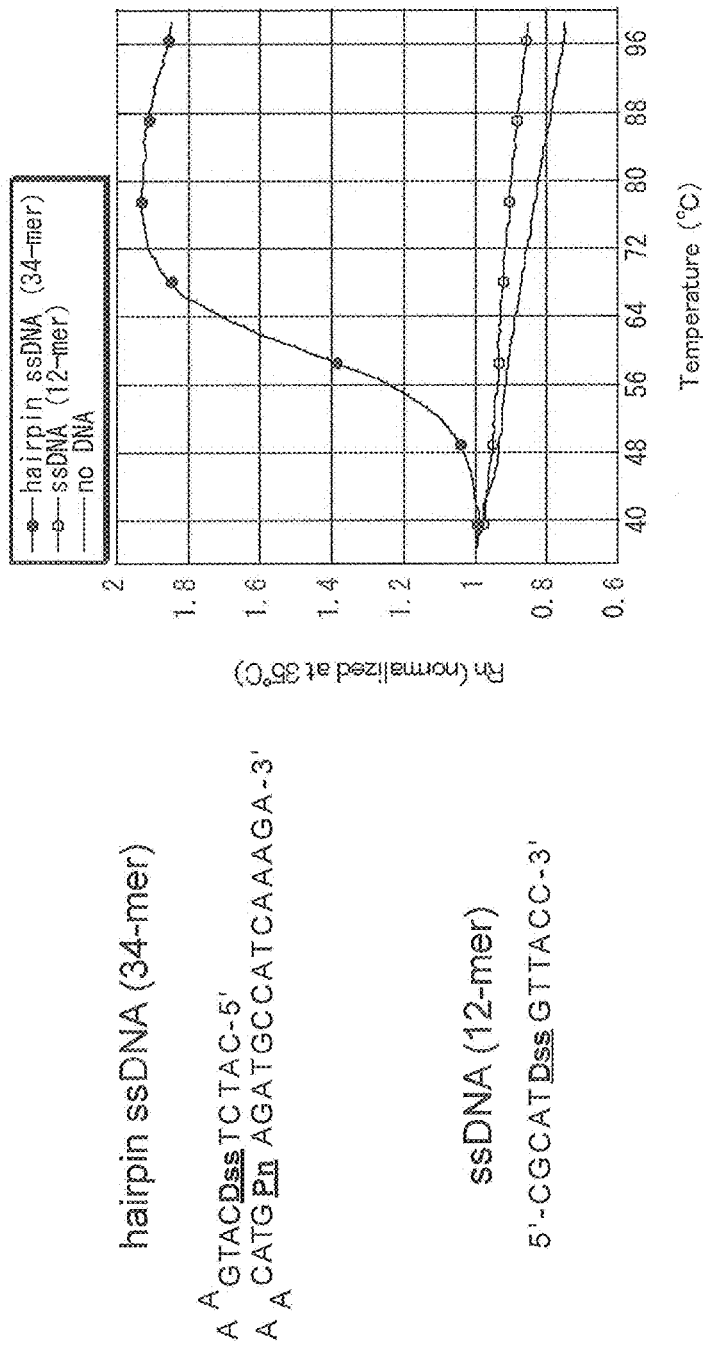

FIG. 16 shows the results of investigation on fluorescent characteristics of a DNA hairpin comprising a Dss-Pn base pair. The temperature dependency of the fluorescence intensity of Dss contained in each of a DNA hairpin (34-mer) comprising a Dss-Pn base pair and a single-stranded DNA (12-mer) comprising Dss was measured. The fluorescence intensity was measured with 1 µM of each DNA in a buffer solution containing 2 mM magnesium chloride. The fluorescence of Dss was quenched by Pn through formation of a hairpin structure by introducing Dss and Pn as a base pair into the stem region of a hairpin nucleic acid. The fluorescence intensity of the Dss increased in a process of thermal denaturation of the hairpin DNA. The properties of the Dss-Pn (or Dss-Px) base pair can be used as a molecular beacon.

Figure 17:
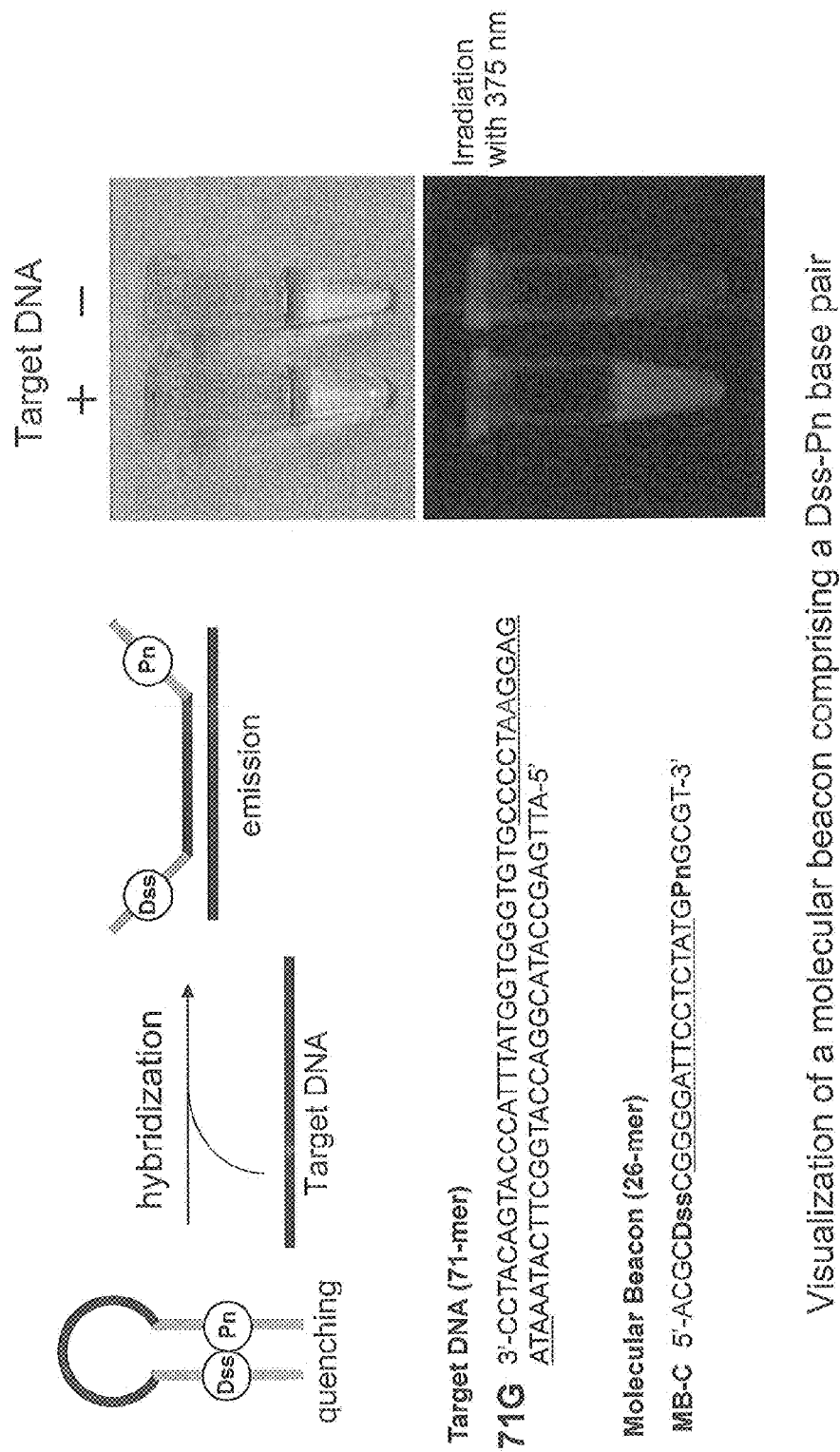

FIG. 17 shows that a molecular beacon comprising a Dss-Pn base pair can be visualized. The fluorescence of a hairpin beacon (26-mer) comprising a Dss-Pn base pair was observed in the presence or absence of a single-stranded DNA (71-mer) as a target. The fluorescence intensity was measured with 1 µM of each DNA in a 10 mM sodium phosphate buffer (pH 7.0) solution containing 100 mM NaCl and 0.1 mM EDTA. As a result, the loop region comprising the Dss-Pn base pair of the molecular beacon recognized a DNA complementary thereto and formed a double strand with the DNA to release the Dss-fluorescence-quenching by Pn, which enabled observation of the fluorescence of Dss with the naked eye by irradiation with ultraviolet light.

Figure 18:
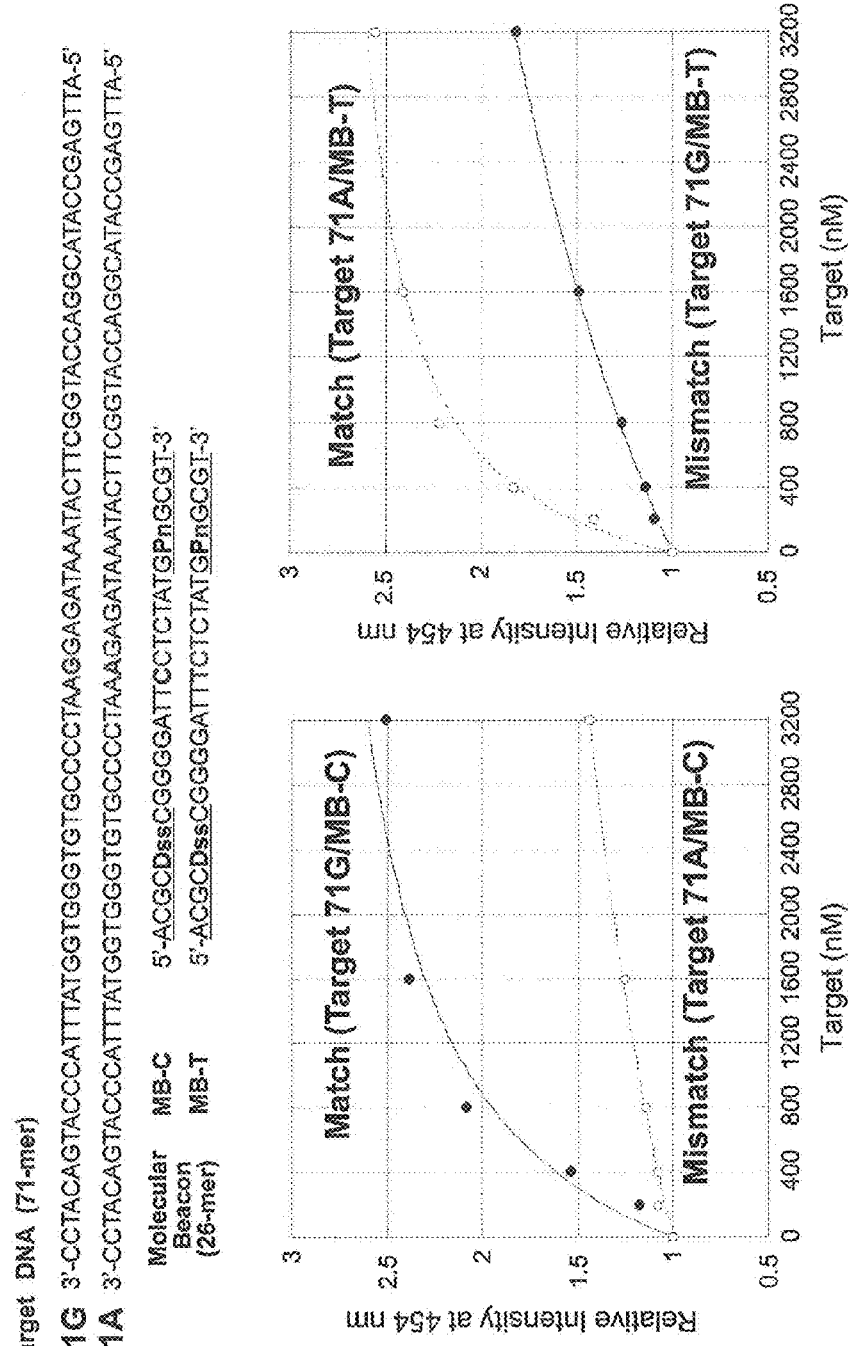

FIG. 18 shows the results of detection of single-nucleotide mutation with a molecular beacon comprising a Dss-Pn base pair. The fluorescence of two hairpin beacons (each 26-mer) each comprising a Dss-Pn base pair was observed by adding a single-stranded DNA (71-mer) having single-nucleotide mutation of each target sequence to the target having the hairpin beacon. The fluorescence intensity was measured with 1 µM of each DNA in a 10 mM sodium phosphate buffer (pH 7.0) solution containing 100 mM NaCl and 0.1 mM EDTA. A difference of one base was distinguished as a difference in light emission intensity of Dss caused by hybridization through production of a molecular beacon, the loop region of which included a sequence complementary to the target DNA sequence.

Figure 19:
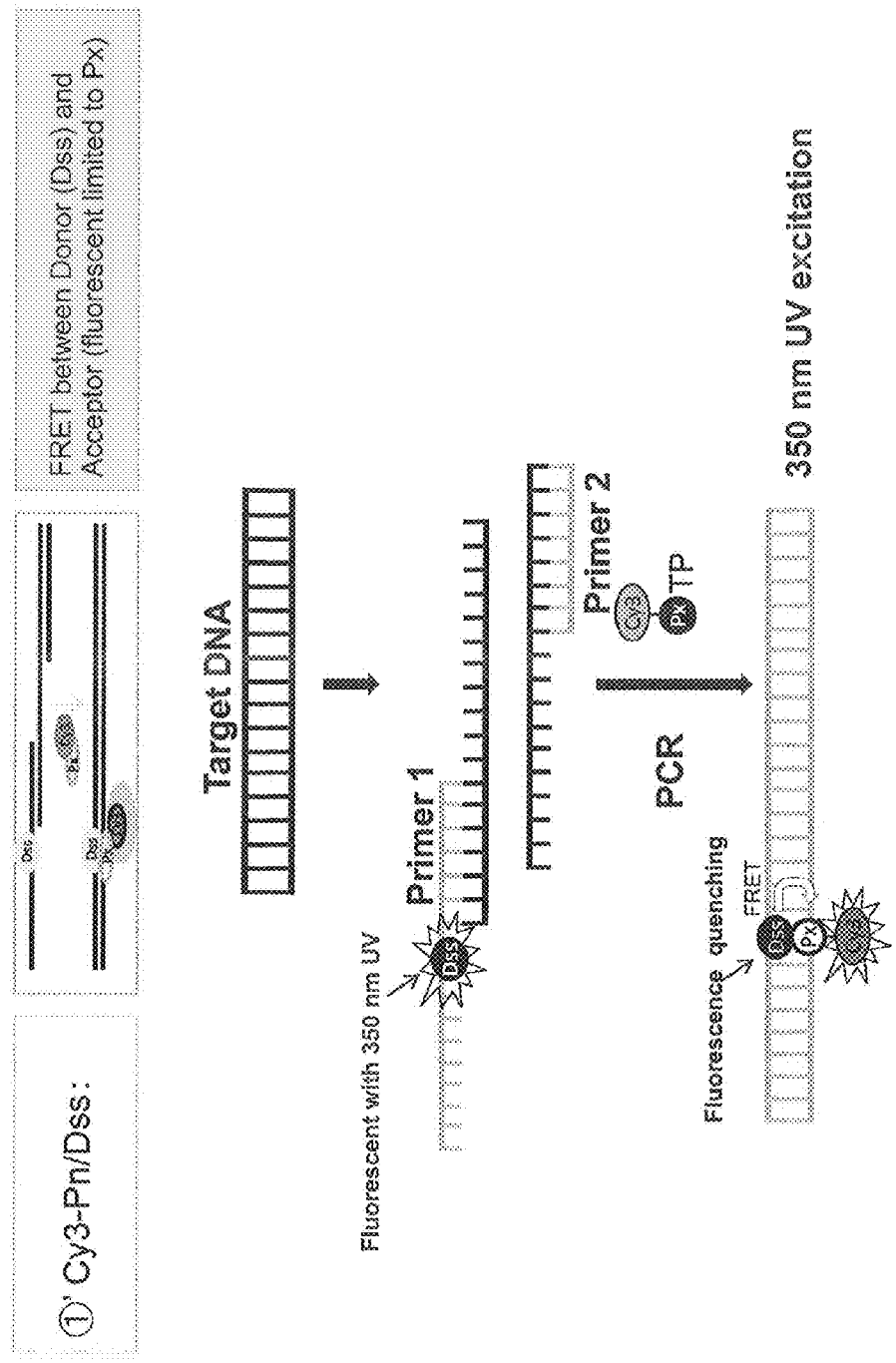

FIG. 19 shows the principle of visualization of PCR using a Cy3-Px/Dss base pair where a fluorescent dye Cy3 is used as a substrate linked to Px.

Figure 20:
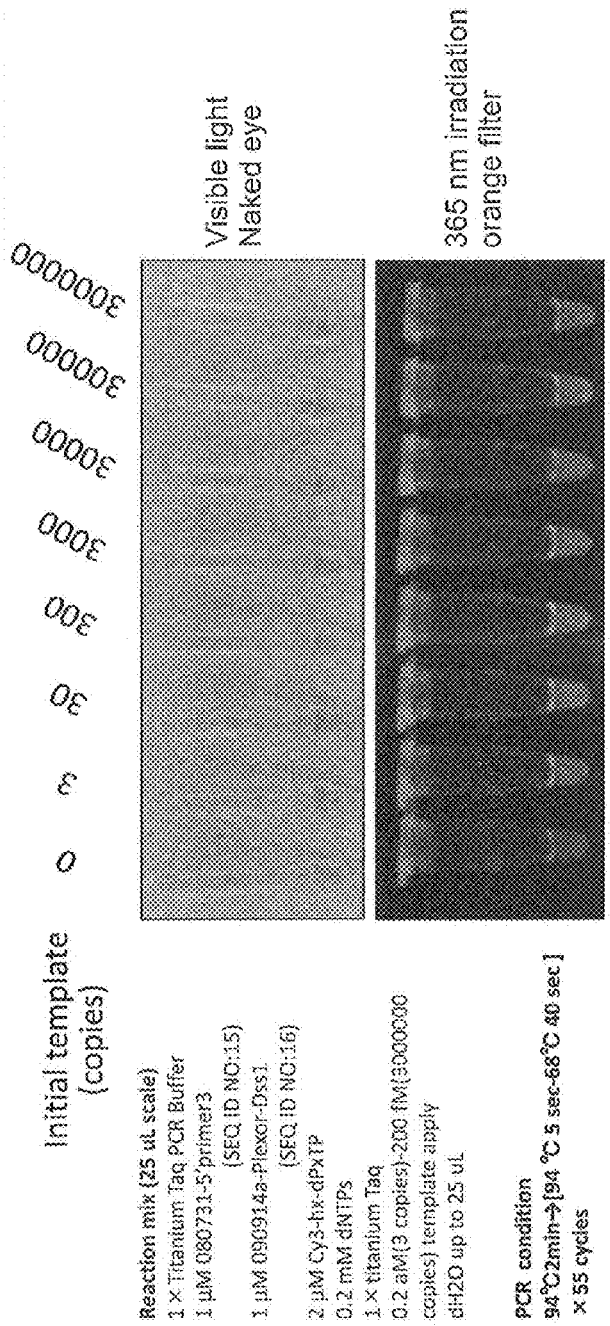

FIG. 20 shows an example of visualization of real-time PCR using a Cy3-Px/Dss base pair on the basis of the principle described in FIG. 19.

Reaction Mixture Solution (25 µL Scale):
1× Titanium Taq PCR buffer,
1 µM 080731-5' primer 3 (SEQ ID NO: 15),
1 µM 090914a-Plexor-Dss1 (SEQ ID NO: 16),
2 µM Cy3-hx-dPxTP,
2 mM dNTPs,
1× Titanium Taq DNA polymerase,
2 aM (3 copies) to 200 fM (3000000 copies) of template DNA, and
sterilized water to adjust the total volume to 25 µL.
PCR Conditions:
94° C. for 2 min and then (94° C. for 5 sec and then 68° C. for 40 sec)×55 cycles.

Since Cy3 does not emit light by excitation with light of about 350 nm, the Cy3-linked Px substrate (Cy3-hx-dPxTP) does not emit light by irradiation with UV light of 350 nm. Incorporation of Cy3-hx-dPxTP into a complementary strand of Dss by formation of a Dss-Px base pair causes fluorescence resonance energy transfer (FRET) from Dss to Cy3 by irradiation with UV light having a wavelength of 350 to 390 nm to cause light emission. Accordingly, the light emission by Cy3 can be observed through an orange filter to allow detection of DNA amplified by PCR with the naked eye.

Figure 21:
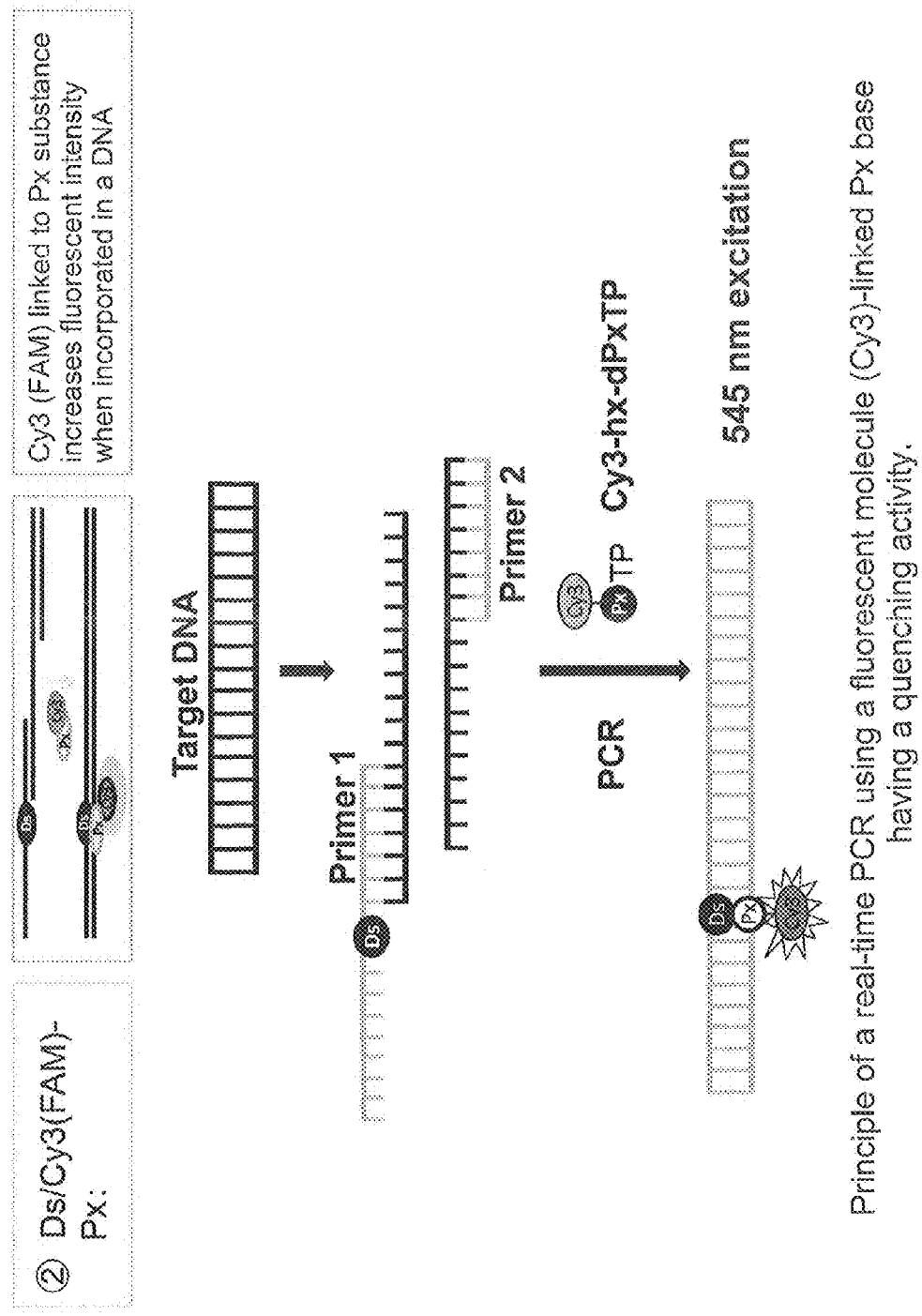

FIG. 21 schematically illustrates the principle of a real-time PCR using a fluorescent molecule (Cy3)-linked Px base having a quenching activity. The fluorescence intensity of a fluorescent molecule (e.g., Cy3) is quenched by about 30% when the fluorescent molecule is linked to a Px base having a quenching activity. When a substrate (Cy3-hx-dPxTP) is used in PCR using a primer including a Ds base, Cy3-hx-dPx is incorporated in a DNA to increase the fluorescence intensity of the Cy3. This method can be used in real-time PCR (FIG. 22).

Figure 22:
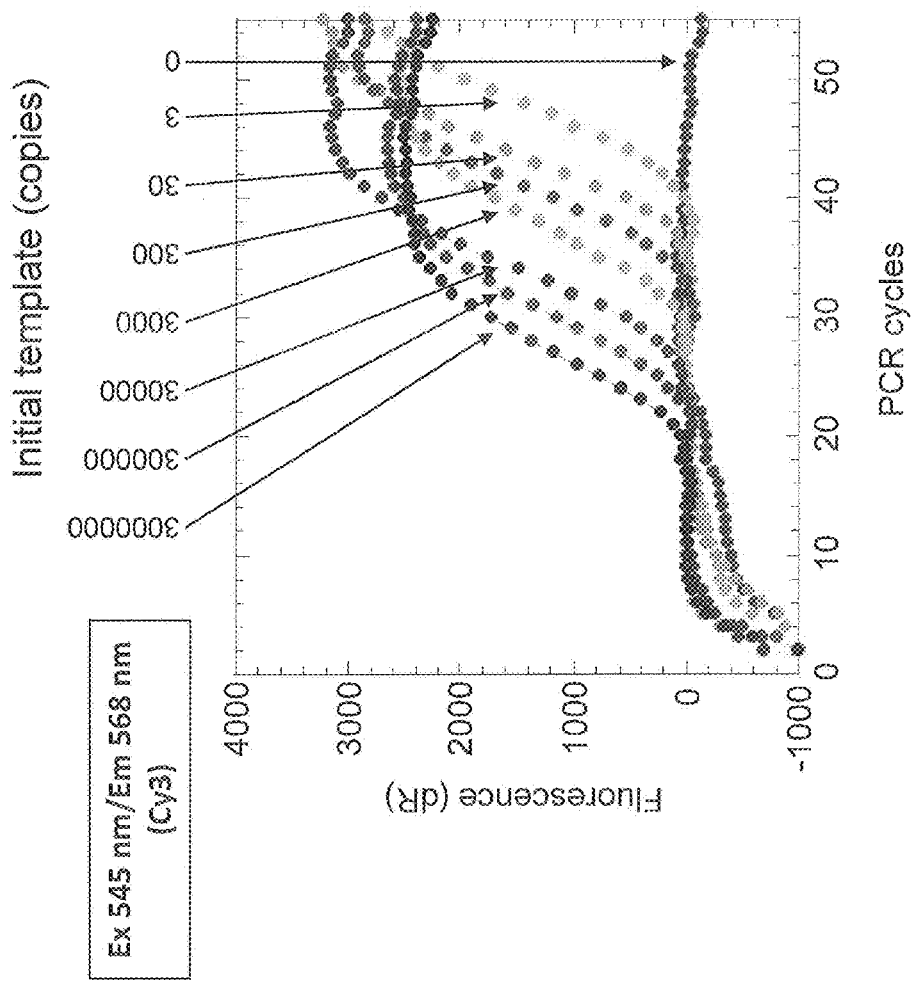

FIG. 22 shows the results of real-time PCR using a fluorescent molecule (Cy3)-linked Px having a quenching activity. The real-time PCR detection was performed using Cy3-hx-dPxTP as a substrate with a real-time PCR machine (Stratagene Mx3005P). The PCR was performed using 1 µM of each primer, 0.2 mM of each natural base substrate dNTP, and 2 µM of an artificial base substrate Cy3-hx-dPxTP, and a change in fluorescence at 568 nm with an excitation wavelength of 545 nm was detected. Unlike the application examples shown in FIGS. 19 and 20, Cy3 is directly excited by irradiation with light of 545 nm; hence, the free substrate Cy3-hx-dPxTP also emits light. Accordingly, unlike the case shown in FIG. 20, the light emission cannot be distinguished in this method, and therefore an increase in fluorescence intensity by incorporation of Cy3-hx-dPxTP into DNA was measured with the real-time PCR machine.

Figure 23:
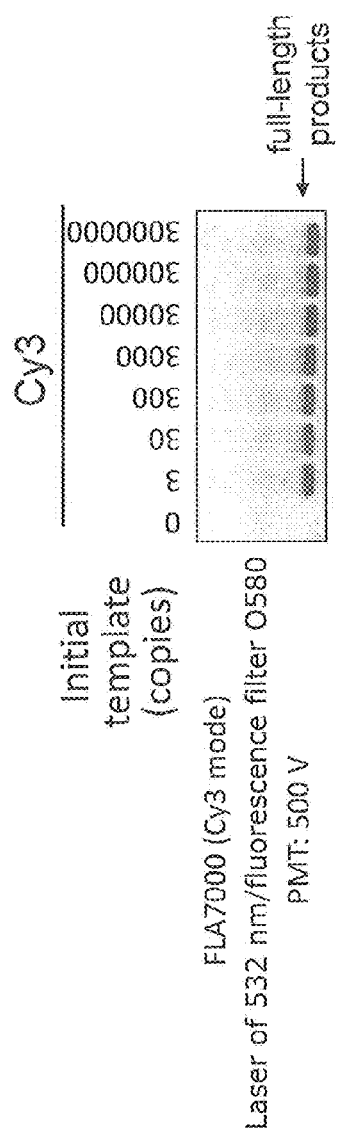

FIG. 23 shows the results of detection of products through real-time PCR using fluorescent molecule (Cy3)-liked Px base having a quenching activity by gel electrophoresis. Since the PCR products shown in FIG. 22 include Cy3, the agarose gel electrophoresis of the PCR products enables the PCR products to be detected on the gel through the fluorescence of Cy3 without a dye for DNA staining such as EtBr or SYBR Green used in conventional methods.

Figure 24:
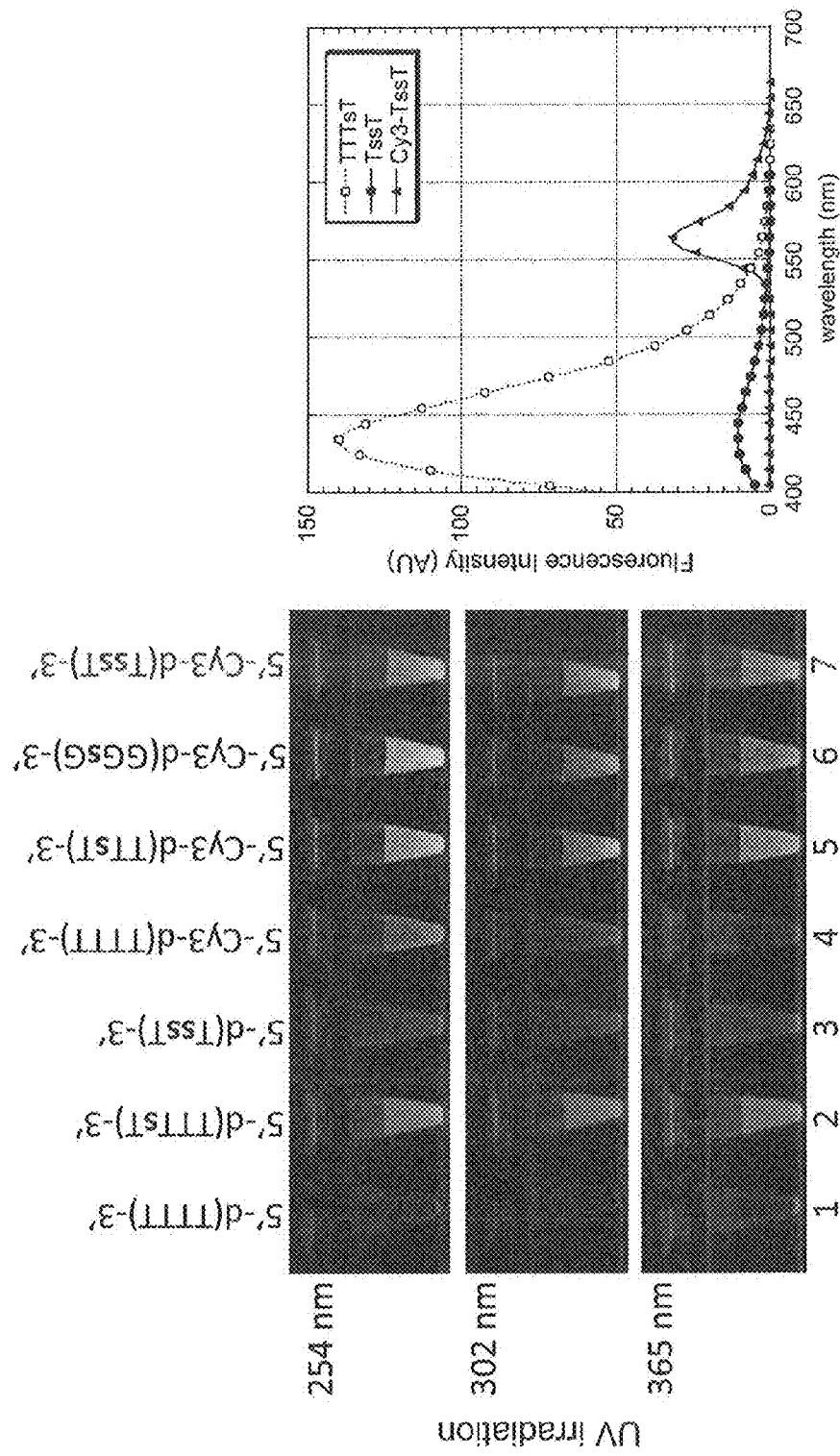

Detection Conditions:
Bioimaging analyzer FLA7000 (Cy3 mode)
Laser of 532 nm/fluorescence filter O580
PMT: 500 V FIG. 24 shows the results of investigation on fluorescent characteristics of DNA comprising a fluorescent molecule (Cy3) and an artificial fluorescent base s. Light emission of 5 µM of each DNA fragment in a 10 mM sodium phosphate (pH 7.0) containing 100 mM NaCl and 0.1 mM EDTA was observed under irradiation with light having a wavelength of 254 to 365 nm. Lane 2 shows the case of a DNA fragment comprising one artificial fluorescent base s, where light emission of s was caused by irradiation with light of 254 to 365 nm. The fluorescence was, however, quenched by introducing two "s'"s adjacent to each other in DNA (Lane 3). When Cy3 was linked to a DNA fragment composed of natural bases only, irradiation with light of 365 nm did not cause light emission (Lane 4). The fluorescence of Cy3 was, however, observed by introducing one or two "s'"s near Cy3 in DNA to cause FRET between s and Cy3 (Lanes 5 to 7). Specifically, Cy3 emitted orange fluorescent light by exciting s with light of 365 nm (Lanes 5 and 6). In a DNA fragment to which two "s'"s were introduced so as to adjacent to each other, "s'"s quench each other so that light emission by s was barely observed even if excitation with light having a wavelength of 254 to 365 nm was performed (Lane 3). Linking of Cy3 to this DNA fragment caused FRET to allow observation of light emission of Cy3 (Lane 7). This phenomenon can be applied to detection of amplification of DNA by replication or transcription with the naked eye.

Figure 25:
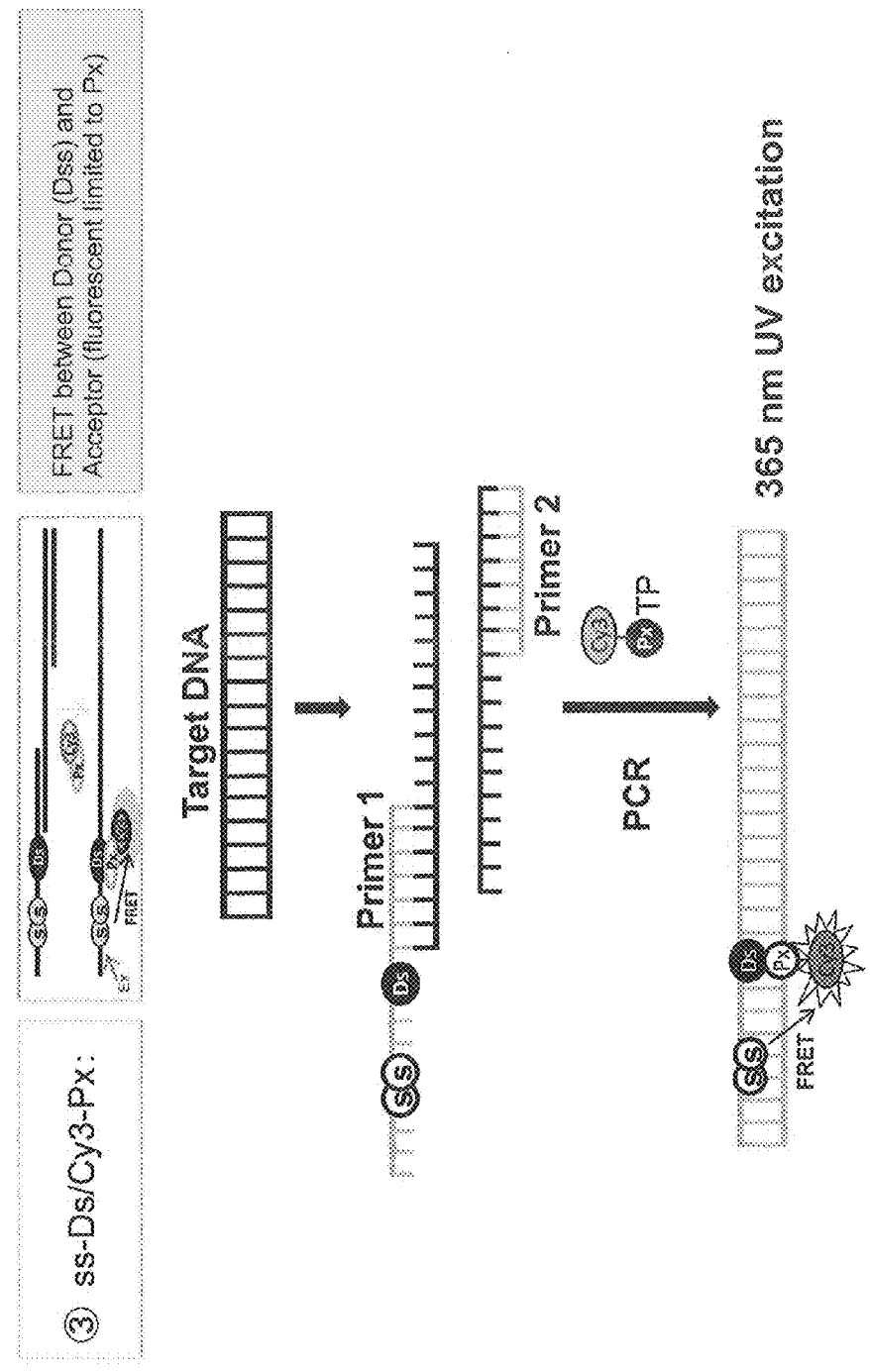
Figure 26:
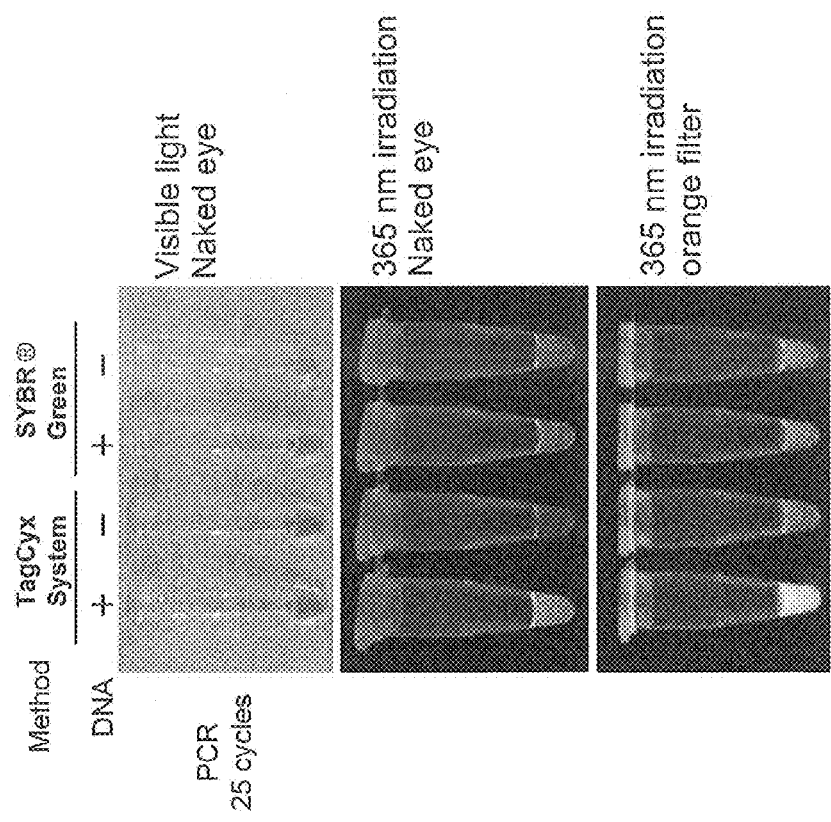

FIG. 25 shows the principle of visualization of PCR using a combination of a fluorescent molecule (Cy3)-linked Px base having a quenching activity and an artificial fluorescent base s. The fluorescence of two artificial fluorescent bases "s'"s introduced so as to be adjacent to each other is completely quenched, and these "s'"s do not emit light by irradiation with light of 350 nm. Ds present near them also does not emit light by irradiation with light of 350 nm. In PCR using a primer comprising two adjacent "s'"s and Ds near the "s'"s and Cy3-hx-dPxTP, Cy3-hx-Px is incorporated into a complementary strand of the primer. Since the two "s'"s and Ds are arranged at positions near to each other, irradiation with light of 365 nm, which is the excitation wavelength for s, causes FRET and thereby fluorescent light emission by the fluorescent dye such as Cy3 near the "s'"s (FIG. 26). This can be applied to detection of DNA amplified by PCR with the naked eye (FIGS. 26 and 27).

FIG. 26 shows the results of visualization of PCR using a combination of a fluorescent molecule (Cy3)-linked Px base having a quenching activity and an artificial fluorescent base s. FIG. 26 shows the results of investigation on light emission by Cy3 with the naked eye or through an orange filter in PCR tubes irradiated with light of 350 nm after PCR. In a conventional method, DNA amplification by PCR cannot be readily observed with the naked eye. That is, in a conventional method, for example, using SYBR Green, which is most widely used in real-time PCR, detection with the naked eye is difficult as shown on the right in FIG. 26. In contrast, the method of the present invention detected not only real-time PCR but also PCR with the naked eye (on the left in FIG. 26).

FIG. 27a shows the results of visualization of PCR using a combination of a fluorescent molecule (Cy3)-linked Px base having a quenching activity and an artificial fluorescent base s. FIG. 28 shows the results of electrophoretic analysis of PCR products by 55 cycles of PCR using 3 to 3000000 copies of target DNA. It was revealed that the detection system can detect amplification products by 55 cycles of PCR from only three copies of DNA with the naked eye, without performing electrophoresis, by merely observing the reaction tube for fluorescence of Cy3 caused by excitation with UV light of 365 nm.

Figure 27B:
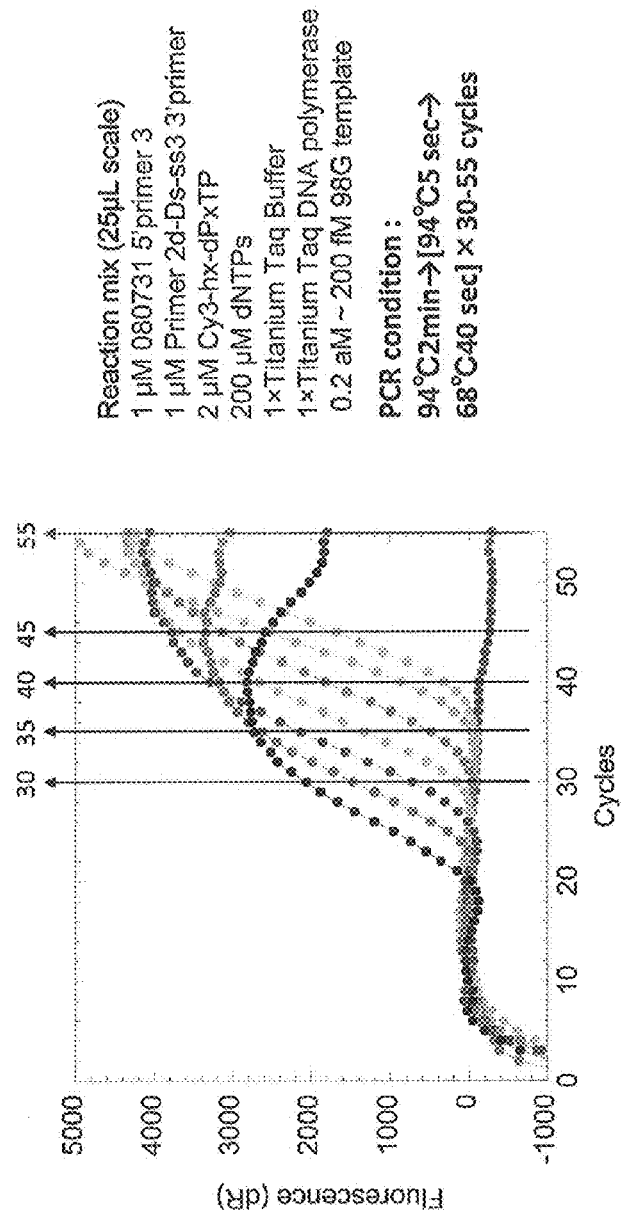
Figure 28:
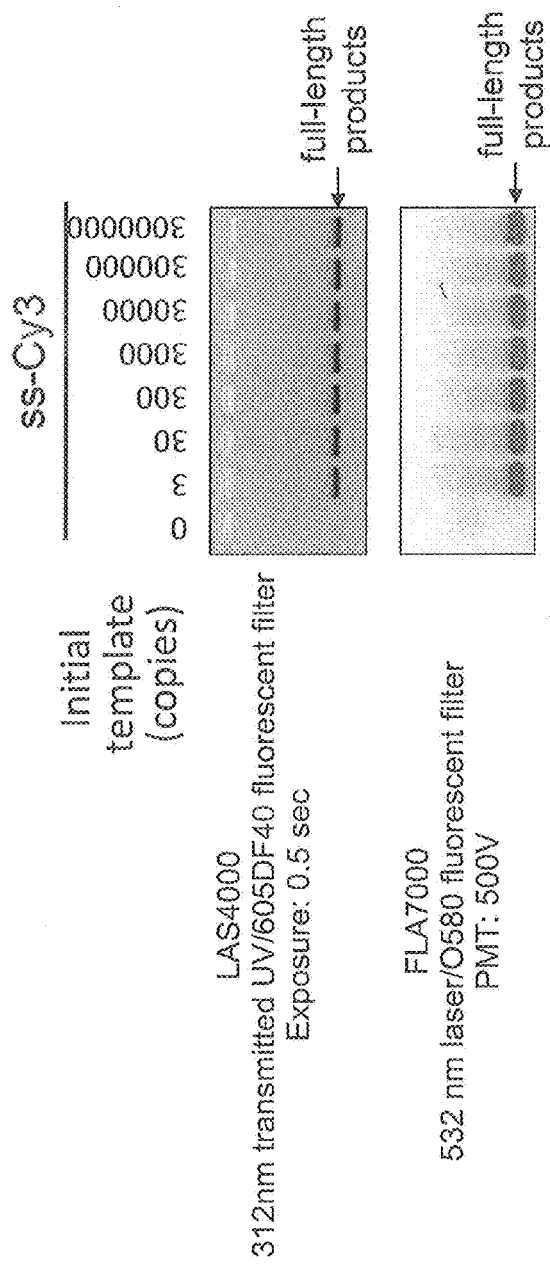

FIG. 27b shows the results of detection of visualization of PCR using a combination of a fluorescent molecule (Cy3)-linked Px base having a quenching activity and an artificial fluorescent base s with a real-time quantitative PCR machine.

Reaction Mixture (25 µL Scale):
1 µM 080731-5' primer 3,
1 µM Primer 2d-Ds-ss3 3' primer,
2 µM Cy3-hx-dPxTP,
200 µM dNTPs,
1× Titanium Taq PCR buffer,
1× Titanium Taq DNA polymerase, and
2 aM (3 copies) to 200 fM (3000000 copies) of 98 G template.

PCR Conditions:
94° C. for 2 min and then (94° C. for 5 sec and then 68° C. for 40 sec)×30 to 55 cycles.

This method also can be applied to real-time PCR because of an increase in fluorescence intensity of Cy3 of Cy3-hx-Px incorporated in DNA.

FIG. 27c shows the results of visualization of DNA products amplified by the respective PCR cycles shown in FIG. 27b.

Figure 1:
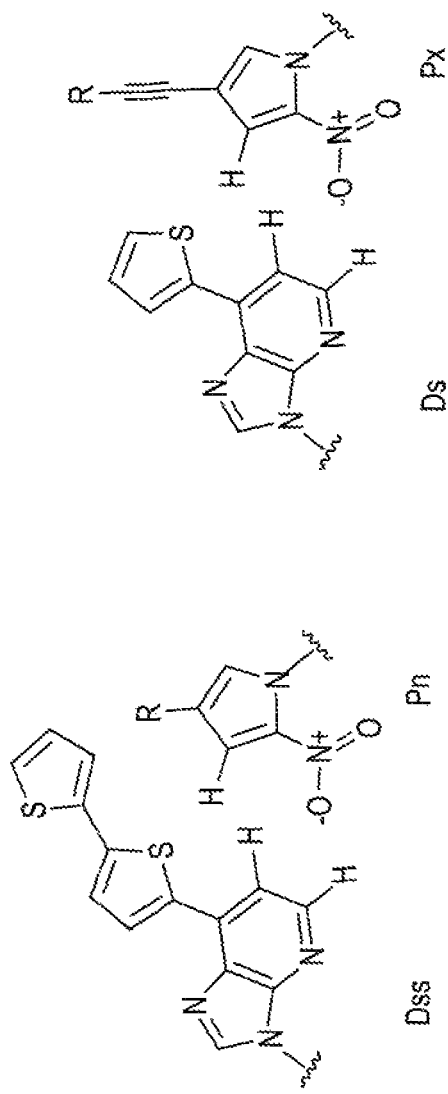
FIG. 1 shows examples of the artificial base pairs of a quenching base (Pn or Px) and a base complementary thereto (Ds or Dss). The examples include an artificial base pair of Pn and an artificial fluorescent base (Dss) and an artificial base pair of Px and Ds.
Figure 2:
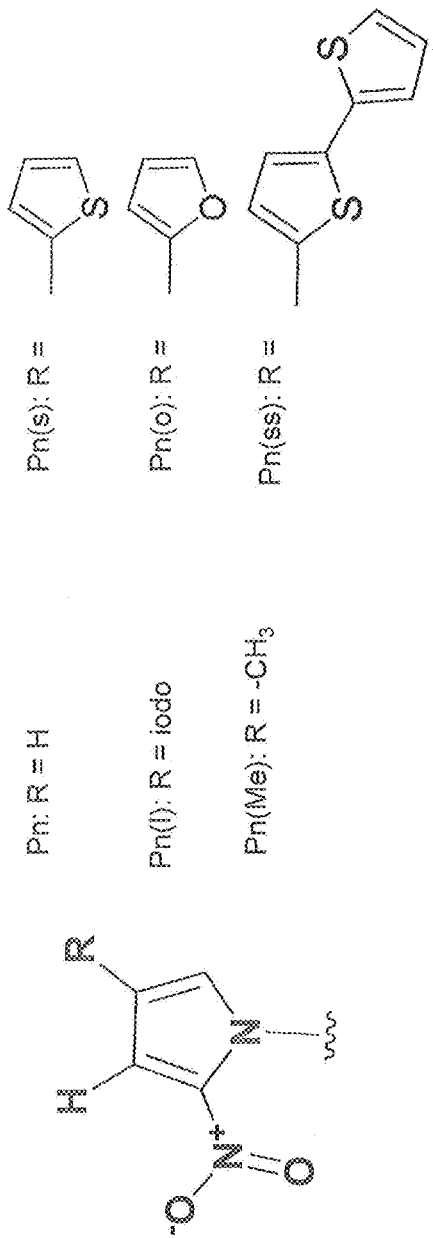
FIG. 2 shows structures of an artificial quenching base Pn and its 4'-derivatives used in Examples of the present invention.

FIG. 27d shows the results of quantification of the fluorescence intensity of each PCR tube shown in FIG. 27c. FIG. 27d1 is a graph plotting the fluorescence intensities at the respective PCR cycles when 0 and 3 to 30000 copies of DNA were amplified by PCR. FIG. 27d2 is a graph plotting the fluorescence intensities when 3 to 3000000 copies of DNA were amplified at respective PCR cycles.

FIG. 28 shows the results of gel electrophoretic detection of products by PCR (55 cycles) using a primer of a combination of a fluorescent molecule (Cy3)-linked Px base having a quenching activity and an artificial fluorescent base s. The PCR products visualized by the method of the present invention shown in FIG. 27a can be detected by irradiation with light of 312 nm or 532 nm on agarose gel electrophoresis. In irradiation with light of 312 nm, FRET from s to Cy3 was detected. In irradiation with light of 532 nm, the results of direct excitation of Cy3 incorporated in DNA are shown. Since the PCR products are labeled with Cy3, it is possible to observe the PCR products on the gel through FRET by excitation of s with light of 312 nm or direct excitation of Cy3 with light of 532 nm.

Figure 6:
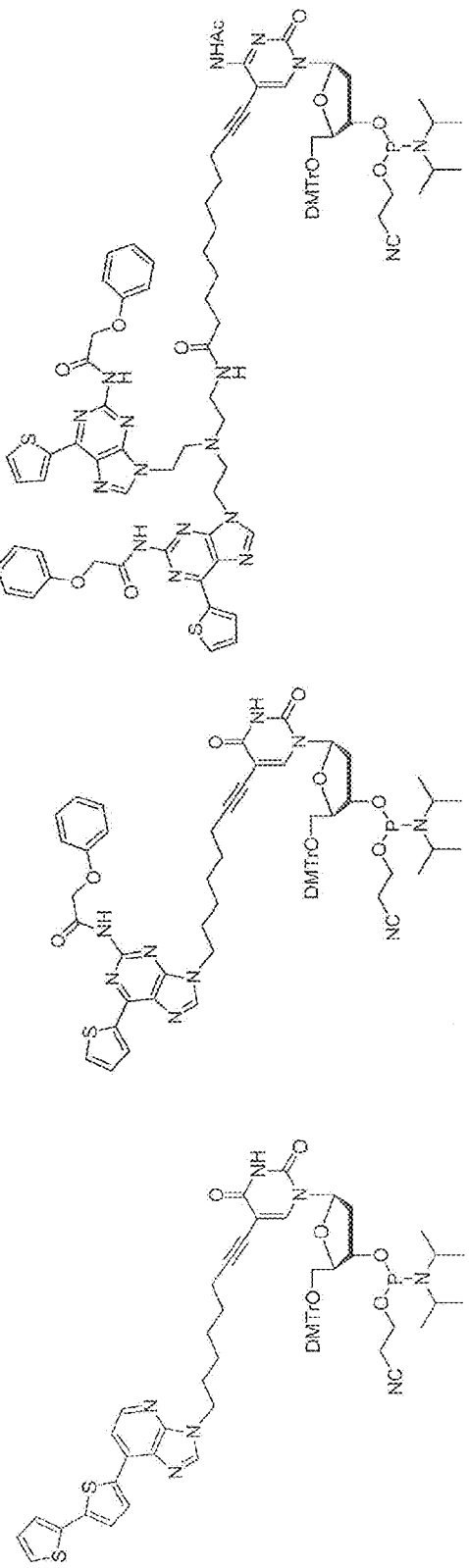
FIG. 6 shows structures of amidite reagents where an artificial fluorescent base Dss or s is linked to a natural base. The compounds shown in FIG. 6 are Dss-hx-dU amidite, s-hx-dU amidite, and s2-hx-dC amidite from the left.

FIG. 29a schematically illustrates a method of detecting products by PCR using a nucleoside derivative (FIG. 6, s-hx-dU, (Us)) where a fluorescent molecule (s base) is linked to a natural base via a linker and a Ds-Px base pair. In the visualization of PCR shown in FIG. 25, adjacent two artificial fluorescent bases "s"'s are used. In the embodiment shown in FIG. 29a, the fluorescent base s is linked to a natural base via a linker, and two s-linked natural bases are introduced into a primer for PCR so as to be adjacent to each other.

Figure 29B:
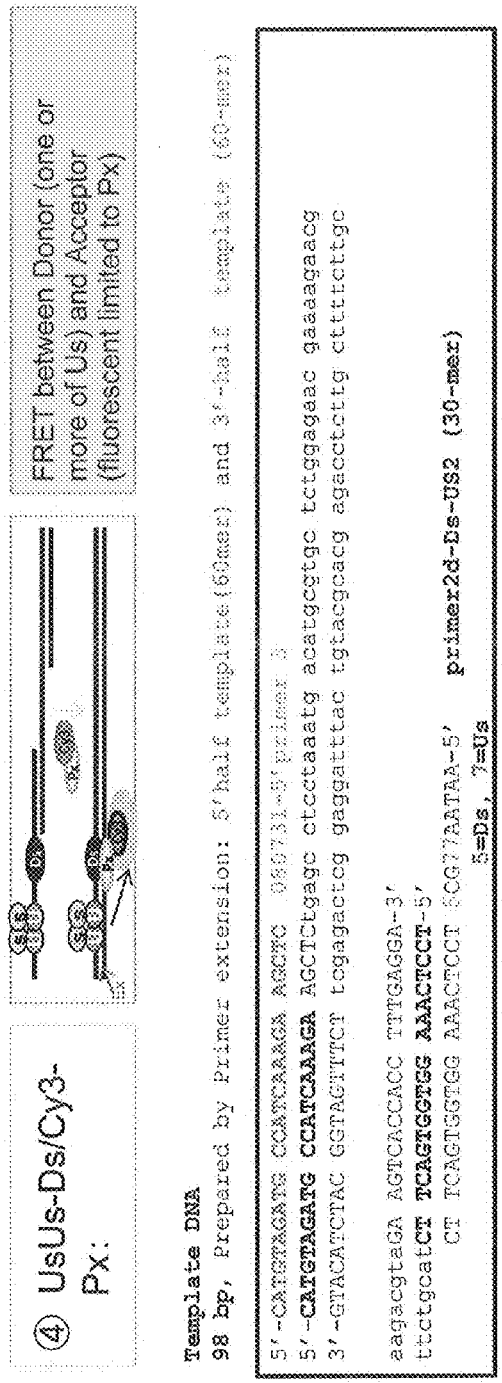

FIG. 29b shows the sequences of each primer and template and conditions for PCR using a nucleoside derivative (FIG. 6, s-hx-dU, (Us)) where a fluorescent molecule (s base) is linked to a natural base via a linker and a Ds-Px base pair.

Figure 29C:
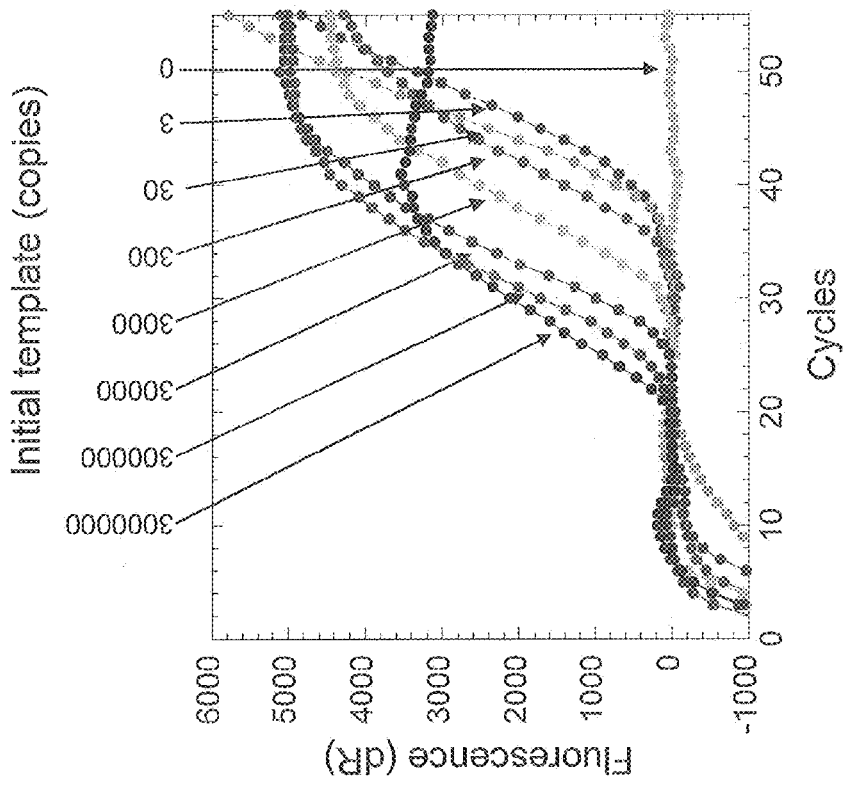

FIG. 29c shows the results of visualization of PCR using a combination of a fluorescent molecule (Cy3)-linked Px base having a quenching activity and an artificial fluorescent base s-hx-dU. This method also can be applied to real-time PCR because of an increase in fluorescence intensity of Cy3 of Cy3-hx-Px incorporated in DNA.

FIG. 29d shows the results of visualization of DNA amplification products by the respective PCR cycles shown in FIG. 29c.

FIG. 30 shows chemical synthesis of an s-hx-dU amidite reagent under conditions:
(a) $CBr_4$, $PPh_3$, $CH_2Cl_2$;
(b) $K_2CO_3$, DMF;
(c) Pac-Cl, HOBT, pyridine, $CH_3CN$;
(d) DMTr-deoxy-5-iodouridine, $Pd(PPh_3)_4$, CuI, TEA, DMF; and
(e) $NC(CH_2)_2O$—$P(Cl)N(iPr)_2$, DIEA, THF.

Figure 31:
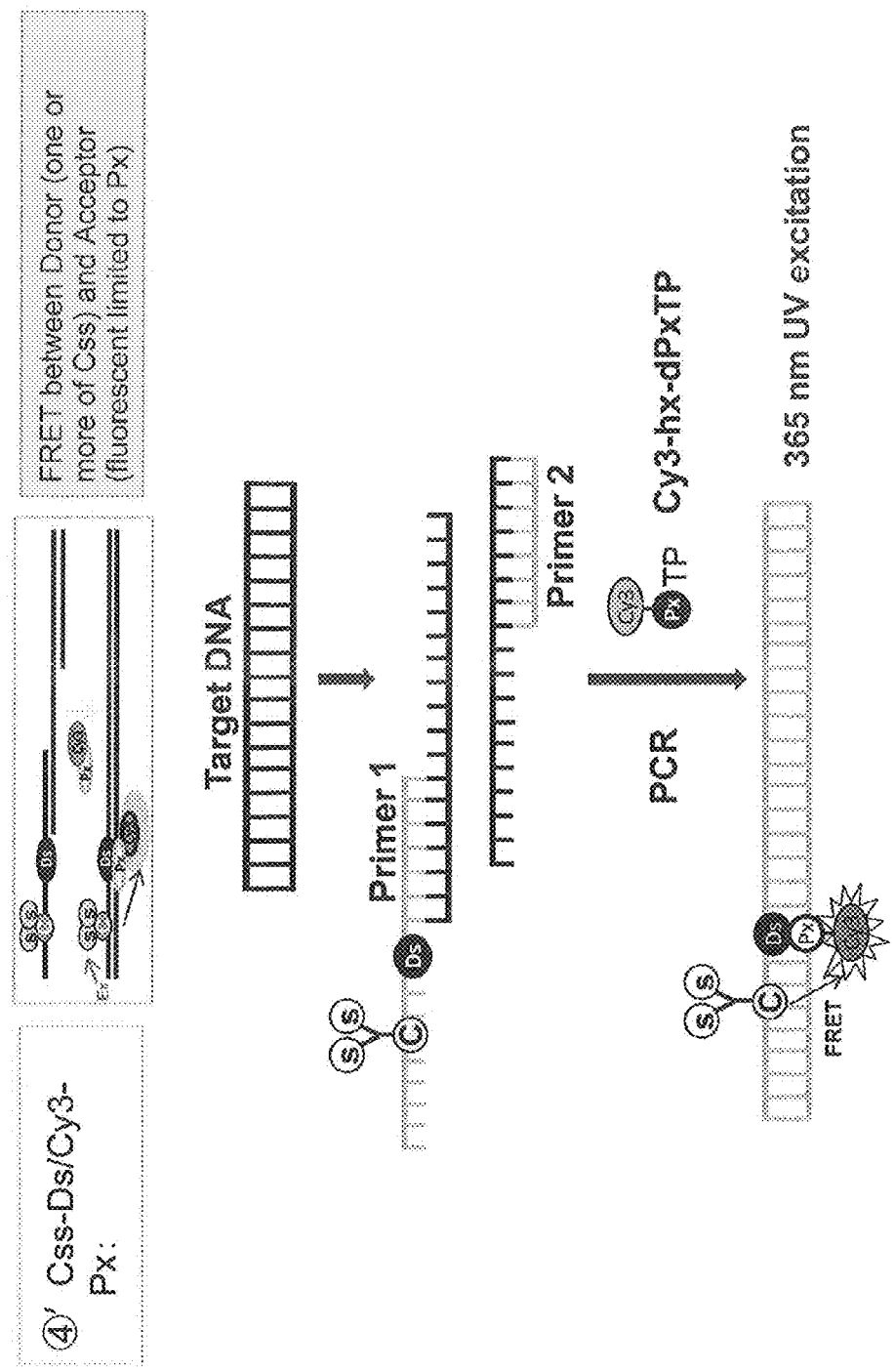

FIG. 31 schematically illustrates a method of detecting products by PCR using a nucleoside derivative (FIG. 6, s2-hx-dC, (Css)) where two fluorescent base (s) molecules are linked to a natural base via a linker and a Ds-Px base pair.

Figure 32:
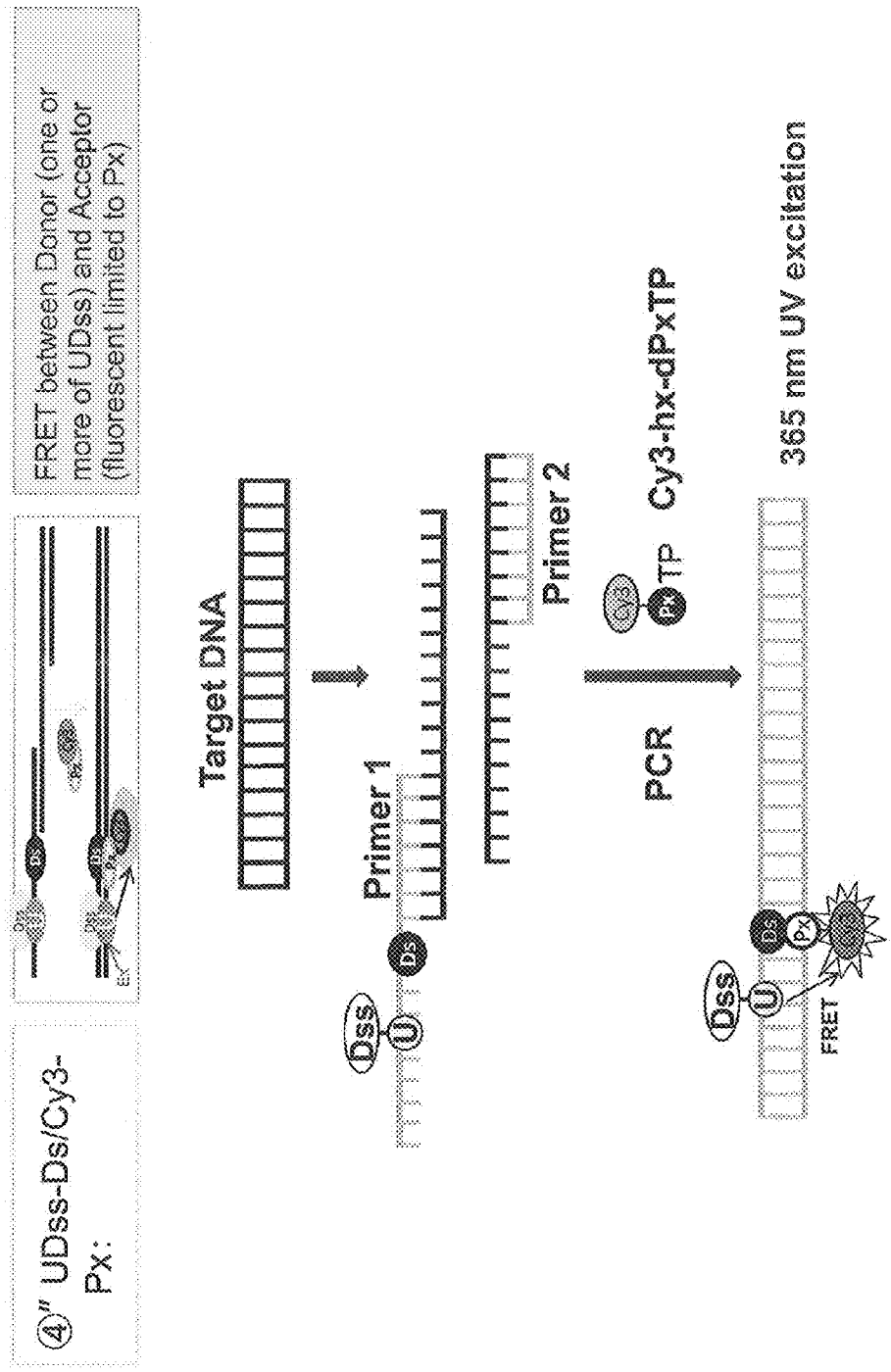

FIG. 32 schematically illustrates a method of detecting products by PCR using a nucleotide derivative (FIG. 6, Dss-hx-dU (UDss)) where a fluorescent molecule (Dss base) is linked to a natural base via a linker and a Ds-Px base pair.

FIG. 33 shows chemical synthesis of a Dss-hx-dU amidite reagent under conditions:
(a) $K_2CO_3$, DMF;
(b) $Pd(PPh_3)_4$, CuI, TEA, DMF;
(c) DMTrCl, pyridine; and
(d) $NC(CH_2)_2O$—$P(Cl)N(iPr)_2$, DIEA, THF.

DESCRIPTION OF EMBODIMENTS

The present invention includes the following preferred embodiments.

A. Method Utilizing a Decrease in Fluorescence Caused by Formation of a Base Pair of an Artificial Fluorescent Base and an Artificial Quenching Base of the Invention The method according to an embodiment of the present invention detects the formation of an artificial base pair by observing a decrease in fluorescence of an artificial fluorescent base caused by the formation of the base pair of an artificial fluorescent base and an artificial quenching base represented by Formula II:

Formula II

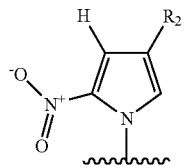

[Formula 25]

(in Formula II, $R_2$ is a group selected from the group consisting of:
hydrogen, hydroxyl and SH groups, and halogens;
substituted or unsubstituted alkyl, alkenyl, and alkynyl groups each having 2 to 10 carbon atoms;
one or more five-membered heterocyclic rings, one or more six-membered heterocyclic rings, and one or more fused heterocyclic rings, these heterocylic rings containing nitrogen or sulfur, and one or more aromatic rings;
sugars, sugar chains, amino acids, and peptides; and
fluorescent molecules linked via linkers).

The artificial fluorescent base is preferably selected from the group consisting of:
(i) a 7-(2,2'-bithien-5-yl)imidazo[4,5-b]pyridin-3-yl group (Dss);
(ii) a 7-(2,2',5',2''-terthien-5-yl)imidazo[4,5-b]pyridin-3-yl group (Dsss);
(iii) a 2-amino-6-(2,2'-bithien-5-yl)purin-9-yl group (ss);
(iv) a 2-amino-6-(2,2',5',2''-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 4-[5-(2-thienyl)thiazol-2-yl]pyrrolo[2,3-b]pyridin-1-yl group (Dvas). These compounds are known to form a base pair with the base represented by Formula II.

In addition to the above-mentioned artificial fluorescent bases, for example, 2-amino purine and ethenoadenosine can also be used.

Preferably, the artificial quenching base of the present invention is represented by the following Formula III or IV:

Formula III

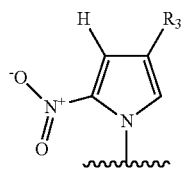

[Formula 26]

(in Formula III, $R_3$ is selected from —H, iodine, —$CH_3$, and:

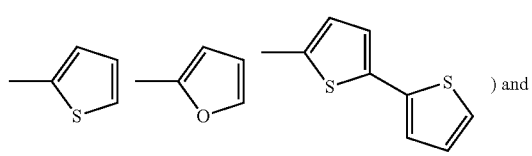

[Formula 27]

) and

Formula IV

[Formula 28]

(in Formula IV, $R_4$ is selected from $-CH_3$, $-CH_2-NH_2$, and:

[Formula 29]

(wherein, n is an integer of 0 to 12)).

In Formula IV, n is preferably an integer of 3 to 7, more preferably 5.

The present invention also provides a kit used in a method of detecting the formation of a base pair of artificial bases on the basis of a decrease in fluorescence of an artificial fluorescent base. The kit includes:

a nucleic acid primer comprising a polynucleotide having a 7-(2,2'-bithien-5-yl)imidazo[4,5-b]pyridin-3-yl group (Dss) as a base; and a polynucleotide having a quenching base represented by Formula III or IV as a base.

B. Method Utilizing a Change in Fluorescence Intensity of a Fluorescent Molecule Linked to an Artificial Quenching Base of the Invention Caused by Formation of an Artificial Base Pair The method according to another embodiment of the present invention detects the formation of an artificial base pair of an artificial quenching base represented by:

Formula V

[Formula 30]

(in Formula V, $R_5$ is a fluorescent molecule linked with a linker) on the basis of a change in fluorescence intensity of the fluorescent molecule in the artificial quenching base caused by formation of the base pair of the artificial base represented by Formula V.

The complementary base to form a base pair with the artificial base of Formula V may be any base such as the above-mentioned Ds, Dss, Dsss, s, ss, sss, dDsa, Dsas, Dsav, dDva, Dvas, or dDia. The complementary base is preferably Ds, s, ss, sss, dDsa, dDva, or dDia, more preferably a 7-(2-thienyl)imidazo[4,5-b]pyridin-3-yl group (Ds).

The artificial quenching base is preferably a base represented by Formula VI:

Formula VI

[Formula 31]

(in Formula VI, $R_6$ is a fluorescent molecule linked directly or via a linker).

As the linker, those described in the quencher represented by Formula I can be used.

As the fluorescent molecule, those described in the quencher represented by Formula I can be used.

The present invention also provides a kit used in a method of detecting the formation of a base pair of an artificial base on the basis of a change in fluorescence intensity. The kit includes:

a nucleic acid primer comprising a polynucleoside having a 7-(2-thienyl)imidazo[4,5-b]pyridin-3-yl group (Ds) as a base; and a polynucleotide having a base represented by Formula VI.

C. Method of Detecting a Nucleic Acid Utilizing a Nucleic Acid Including a Polynucleoside Having a Modified Natural Base, Artificial Base, or Base Analog Having a Self-Quenching Activity that can Function as a Donor in, for Example, Fluorescence Resonance Energy Transfer (FRET) or Static Quenching An embodiment of the present invention provides a method of detecting the formation of an artificial base pair. The method utilizes a nucleic acid comprising a polynucleoside having a modified natural base, artificial base, or base analog having a self-quenching activity that can function as a donor in, for example, fluorescence resonance energy transfer (FRET) or static quenching. Formation of an artificial base pair of an artificial base (a first artificial base) and an artificial base having a fluorescent molecule (a second artificial base) in the nucleic acid causes a change in fluorescence spectrum caused by fluorescence resonance energy transfer from the polynucleotide including the modified natural base, artificial base, or base analog to the fluorescent molecule of the second artificial base or static quenching to allow detection of the formation of the artificial base pair.

The nucleic acid having the artificial base pair of an artificial base (a first artificial base) and an artificial base having a fluorescent molecule (a second artificial base) preferably has an artificial quenching base represented by Formula II of the present invention as the second artificial base, but the nucleic acid is not necessarily limited thereto. A nucleic acid including a polynucleoside having a modified natural base, artificial base, or base analog having a self-quenching activity that can function as a donor in, for example, fluorescence resonance energy transfer (FRET) and/or static quenching in a known artificial base pair can be used.

C-1

The present invention provides the following embodiment as a variation of method C.

In the method of the present invention of detecting the formation of a base pair of artificial bases on the basis of a change in fluorescence spectrum caused by, for example, fluorescence resonance energy transfer or static quenching, the formation of a base pair of a 7-(2,2'-bithien-5-yl)imidazo[4,5-b]pyridin-3-yl group (Dss) and a base represented by the following Formula VI:

Formula VI

[Formula 32]

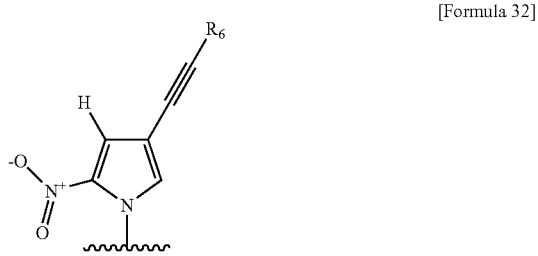

(in Formula VI, $R_6$ is a fluorescent molecule linked directly or via a linker) causes fluorescence resonance energy transfer from Dss to the fluorescent molecule in the base of Formula VI or static quenching by excitation with ultraviolet light having a wavelength of 240 to 410 nm. This causes a change in fluorescence spectrum, and the method detects the formation of the artificial base pair on the base of the change.

FIG. 19 schematically illustrates this embodiment.

Dss is excited with ultraviolet light having a wavelength of 240 to 410 nm. It is desirable that the fluorescent molecule in the base of Formula VI does not produce fluorescence at this wavelength, but do produce fluorescence only when FRET has occurred.

In embodiments of C-2 to C-4, the formation of an artificial base pair of a 7-(2-thienyl)imidazo[4,5-b]pyridin-3-yl group (Ds) and a base Formula VI is detected.

C-2

The present invention provides the following embodiment as a variation of method C.

In the method of the present invention of detecting the formation of a base pair of artificial bases on the basis of a change in fluorescence spectrum caused by, for example, fluorescence resonance energy transfer or static quenching, the formation of a base pair of a 7-(2-thienyl)imidazo[4,5-b]pyridin-3-yl group (Ds) and a base represented by Formula VI causes, for example, fluorescence resonance energy transfer from at least one 2-amino-6-(2-thienyl)purin-9-yl group (s) to the fluorescent molecule in the base of Formula VI or static quenching by excitation with ultraviolet light having a wavelength of 240 to 390 nm. This causes a change in fluorescence spectrum, and the method detects the formation of the artificial base pair on the basis of the change, wherein at least one polynucleotide having a 2-amino-6-(2-thienyl)purin-9-yl group (s) as a base is present in the same nucleic acid strand comprising a polynucleoside having Ds as a base.

FIG. 25 schematically illustrates this embodiment.

The number of "s"'s present in the same nucleic acid strand comprising the nucleoside having Ds as a base is not limited, but is preferably one to three, more preferably one or two, and most preferably two. As shown in Lane 3 of FIG. 24, when the number of "s"'s is two, the fluorescence intensity of s's is decreased or quenched by the self-quenching activity of "s"'s (self quenching), and a change in fluorescence spectrum caused by FRET is clearly observed (Lane 7 of FIG. 24). When the number of s is one, the fluorescence of s is observed (Lane 2 of FIG. 24). In this case, FRET allows the observation of fluorescence of the fluorescent molecule instead of the fluorescence of s (Lanes 5 and 6 of FIG. 24).

In addition to the embodiment where two or more artificial bases are present in an identical nucleic acid such as the case of having two "s"'s adjacent to each other, cases of a natural base to which a base having self-quenching activity is linked and of one artificial base having two or more quenching base (s) moieties, such as Dss, can also be used in the method of the present invention utilizing FRET and/or static quenching.

C-3

The present invention provides the following embodiment as a variation of method C.

In the method of the present invention of detecting the formation of a base pair of artificial bases on the basis of a change in fluorescence spectrum caused by, for example, fluorescence resonance energy transfer or static quenching, the formation of a base pair of Ds and a base represented by Formula VI causes, for example, fluorescence resonance energy transfer from at least one 2-amino-6-(2-thienyl)purin-9-yl group (s) to the fluorescent molecule in the base of Formula VI or static quenching by excitation with ultraviolet light having a wavelength of 350 to 390 nm. This causes a change in fluorescence spectrum, and the method detects the formation of the artificial base pair on the basis of the change, wherein at least one polynucleotide having at least one natural base to which at least one 2-amino-6-(2-thienyl)purin-9-yl group (s) linked is present in the same nucleic acid strand comprising a polynucleoside having Ds as a base.

FIGS. 29a and 31 schematically illustrate this embodiment.

The type of the natural base to which s is linked is not limited and can be any of A, T, G, C, and U. When two or more s-linked natural bases are present to be adjacent to each other, the natural bases may be the same or different, preferably the same. The number of the s-linked natural bases adjacent to each in a nucleic acid is not particularly limited as in the embodiment of C-2 where s is present in an identical nucleic acid, and is preferably one to three, more preferably one or two, and most preferably two.

The embodiment of C-3 encompasses an embodiment where two or more "s"'s are linked to one natural base (FIG. 31). The number of "s"'s is not particularly limited, but is preferably two or three, more preferably two.

C-4

The present invention provides the following embodiment as a variation of method C.

In the method of the present invention of detecting the formation of a base pair of artificial bases on the basis of a change in fluorescence spectrum caused by, for example, fluorescence resonance energy transfer or static quenching, the formation of a base pair of Ds and a base represented by Formula VI causes, for example, fluorescence resonance energy transfer from a 7-(2,2'-bithien-5-yl)imidazo[4,5-b]pyridin-3-yl group (Dss) to the fluorescent molecule in the base of Formula VI or static quenching by excitation with ultraviolet light having a wavelength of 240 to 410 nm. This causes a change in fluorescence spectrum, and the method detects the formation of the artificial base pair on the basis of the change, wherein a polynucleotide having a natural base to which at least one 7-(2,2'-bithien-5-yl)imidazo[4,5-b]pyridin-3-yl group (Dss) linked is present in the same nucleic acid strand comprising a polynucleoside having Ds as a base.

FIG. 32 schematically illustrate this embodiment.

In the embodiments of method C including C-1 to C-4 of the present invention, any fluorescent molecule can be used without limitation. Preferred are those described in the quencher represented by Formula I, more preferably indocarbocyanine (Cy3).

The substituent $R_6$ in the base represented by Formula VI preferably has the following structure:

[Formula 33]

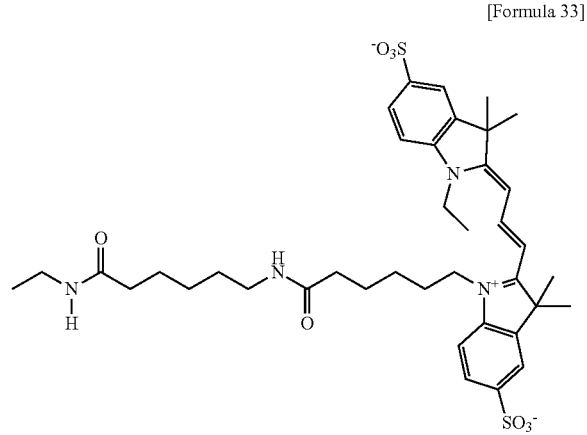

The present invention further provides a kit used in a method of detecting the formation of a base pair of artificial bases on the basis of a change in fluorescence spectrum caused by, for example, fluorescence resonance energy transfer or static quenching. The kit includes one nucleic acid primer selected from the group consisting of the following i) to iv:

i) a nucleic acid primer comprising a polynucleotide having Dss as a base;

ii) a nucleic acid primer comprising a polynucleoside having Ds as a base and a polynucleotide having at least one s as a base;

iii) a nucleic acid primer comprising a polynucleoside having Ds as a base and a polynucleotide having at least one natural base to which at least one s is linked; and iv) a nucleic acid primer comprising a polynucleoside having Ds as a base and a polynucleotide having a natural base to which Dss is linked, and the kit includes a polynucleotide having a base represented by Formula VI.

The Dss-Pn and Dss-Px base pairs efficiently function also in PCR. In the present invention, the base pairs of nucleic acid may be formed in any process of transcription, reverse transcription, replication, and translation.

The method of detection of the present invention utilizing FRET and/or static quenching (embodiment C) is characterized in that a change in detection spectrum can be observed with the naked eye. Prior to the present invention, no method could simply detect the formation of an artificial base pair or target nucleic acid in a visible form. The method of detection of the present invention can be applied to visualization of real-time PCR. Accordingly, no complicated and expensive PCR machine is necessary.

Furthermore, in amplification of nucleic acid by the method of the present invention of detecting an artificial base pair, the amplified nucleic acid can be simply detected by directly performing electrophoresis (e.g., FIG. 23). In addition, it enables quantification of the nucleic acid on the basis of the density of the band in the electrophoresis.

EXAMPLES

The present invention will be more specifically described by the following examples, which are not intended to limit the technical scope of the present invention. Those skilled in the art can easily add modifications or changes to the present invention on the basis of the description of this specification, and such modifications and changes are included in the technical scope of the present invention.

Example 1

Figure 5:
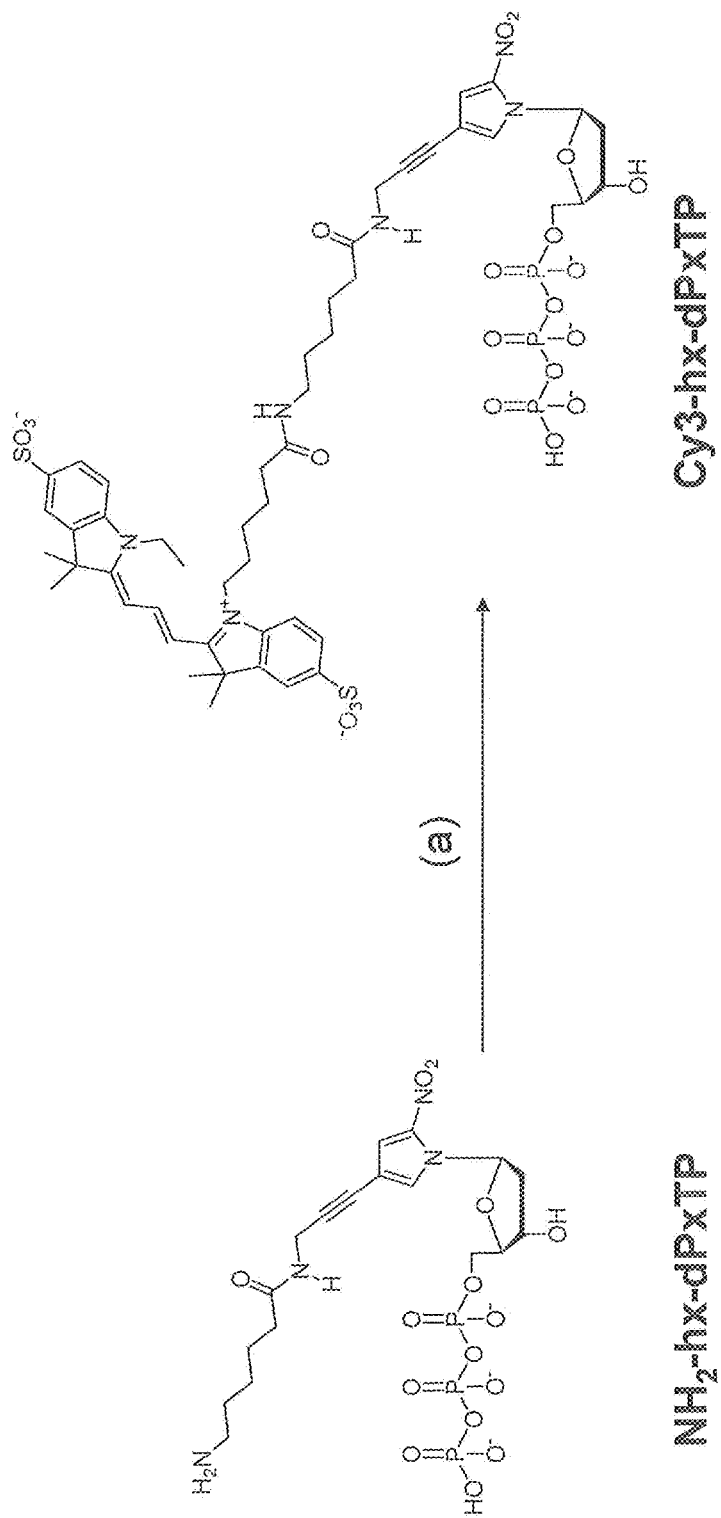
FIG. 5 shows synthesis of Cy3-hx-dPxTP from $NH_2$-hx-dPxTP. The reaction conditions are: $NH_2$-hx-dPxTP (8.4 mmol) in 100 mM $NaHCO_3$, $Na_2CO_3$ buffer (pH 8.5) (500 μL), Cy3 (7.63 μmol) N-hydroxysuccinimidyl ester in DMF (300 μL), at room temperature for 12 hours.

Chemical Synthesis of Cy3-Hx-dPxTP (FIG. 5)

1) Reagent, Solvent, and Other Components

Reagents and solvents were purchased from typical suppliers and were used without further purification. $^1$H-NMR (300 MHz) and $^{31}$P-NMR (121 MHz) spectra were recorded on a BRUKER AV300 nuclear magnetic resonance spectrometer. Synthesized nucleoside 5'-triphosphate was subjected final purification with a Gilson HPLC system. Electrospray-ionization mass spectra (ESI-MS) were recorded on a Waters ZMD 4000 mass system equipped with a Waters 2690 LC system.

2) Synthesis of 1-(2-deoxy-β-D-ribofuranosyl-4-[3-(Cy3-carboxamide hexanamide)-1-propynyl]-2-nitropyrrole 5'-triphosphate (Cy3-hx-dPxTP)

A solution of Cy3 N-hydroxysuccinimidyl ester (Cy3-SE, 6.0 mg, 7.63 μmol) in DMF (300 μL) was added to a 100 mM NaHCO$_3$—Na$_2$CO$_3$ buffer solution (pH 8.6, 500 μL) containing 1-(2-deoxy-β-D-ribofuranosyl)-4-[3-(6-aminohexanamide)-1-propynyl]-2-nitropyrrole 5'-triphosphate (NH$_2$-hx-dPxTP) (8.4 μmol), and the mixture was left to stand at room temperature for 12 hours. A 50 mM TEAA (3.0 mL) solution was added to the reaction solution, and Cy3-hx-dPxTP (2.7 μmol, 35%) was yielded through purification by DEAE Sephadex A-25 and HPLC.

3) Physical Properties of Cy3-Hx-dPxTP $^1$H NMR (300 MHz, D$_2$O) δ 8.55 (t, 1H, J=13.6 Hz), 7.90 (t, 2H, J=1.7 Hz), 7.85 (dd, 2H, J=1.2, 8.4 Hz), 7.78 (d, 1H, J=2.1 Hz), 7.39 (dd, 2H, J=1.9, 8.5 Hz), 7.19 (d, 1H, J=2.1 Hz), 6.64 (t, 1H, J=5.9 Hz), 6.39 (dd, 2H, J=2.8, 13.5 Hz), 4.59 (m, 1H), 4.22-4.08 (m, 9H), 3.20 (q, 32H, J=7.3 Hz), 3.07 (t, 2H, J=6.5 Hz), 2.59 (dt, 1H, J=6.1, 13.3 Hz), 2.38 (dt, 1H, J=6.2, 13.8 Hz), 2.27-2.17 (m, 2H), 1.86 (m, 2H), 1.77 (s, 12H), 1.67-1.54 (m, 4H), 1.42-1.25 (m, 56H).

$^{31}$P NMR (121 MHz, D$_2$O) δ −8.65 (bs, 1P), −10.72 (d, 1P, J=19.7 Hz), −22.32 (t, 1P, J=20.4 Hz).

MS (ESI) for C$_{49}$H$_{65}$N$_6$O$_{22}$P$_3$S$_2$, calculated value: 1247.28 (M+H)$^+$, observed value: 1247.43 (M+H)$^+$, calculated value: 1245.28 (M−H)$^-$, observed value: 1244.91 (M−H)$^-$.

Example 2

Figure 7:
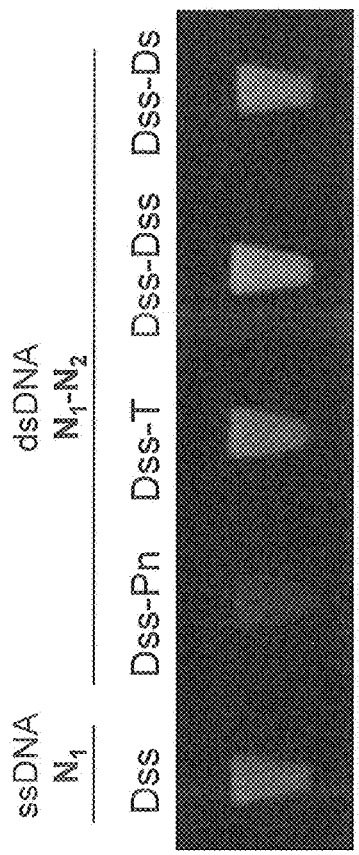
FIG. 7 shows quenching of an artificial fluorescent base Dss by an artificial base Pn in a complementary strand, which was photographed by irradiating each DNA (5 μM) in a solution of 10 mM sodium phosphate (pH 7.0), 100 mM NaCl, and 0.1 mM EDAT with light of 365 nm. The fluorescence of an artificial fluorescent base (Dss) is quenched by an artificial quenching base (Pn) by formation of a double strand of a single-stranded oligonucleotide (12-mer) comprising Dss and a complementary oligonucleotide (12-mer) comprising Pn (the second from the left in FIG. 7). The fluorescence of Dss is not quenched even if Dss forms a base pair with a natural base (such as T) or an artificial base (Dss or Ds) (the third to fifth from the left in FIG. 7).

Quenching of Artificial Fluorescent Base Dss by Artificial Base Pn in Complementary Strand (FIG. 7)

In order to investigate a change in fluorescence in a single-stranded DNA fragment including an artificial fluorescent base Dss (12-mer, 5'-GGTAACN$_1$ATGCG-3', N$_1$=Dss) (SEQ ID NO: 1) or in a double-stranded DNA formed with a complementary DNA fragment (12-mer, 5'-CGCATN$_2$GTTACC-3', N$_2$=Pn, Dss, Ds, or T) (SEQ ID NO: 2), a solution containing 5 μM of a single-stranded DNA (ssDNA) or a double-stranded DNA (dsDNA), 10 mM sodium phosphate (pH 7.0), 100 mM NaCl, and 0.1 mM EDTA was prepared. After annealing, the fluorescence was photographed by irradiation with light of 365 nm using an UV transilluminator. The results are shown in FIG. 7.

Example 3

Figure 8:
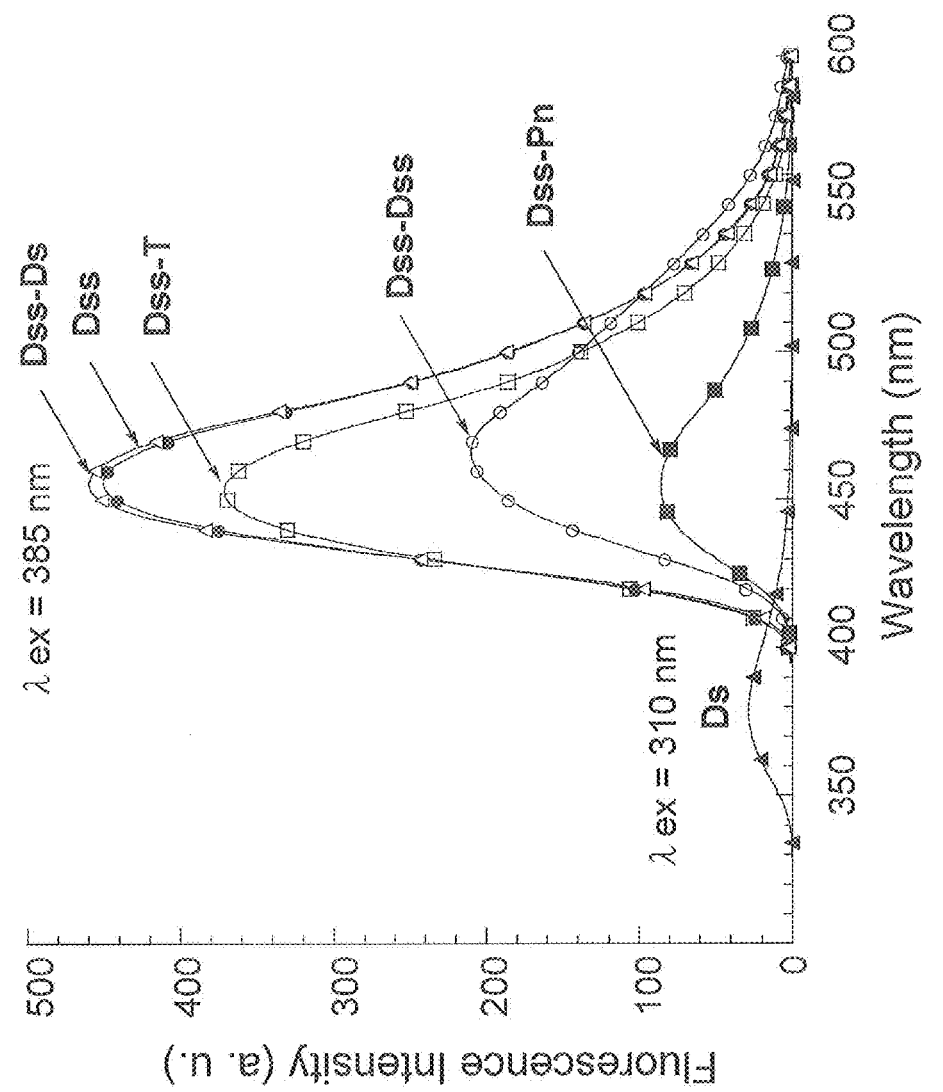
FIG. 8 shows the fluorescence spectrum of each DNA fragment of the examples shown in FIG. 7, i.e., the fluorescence spectra (excitation wavelength: 385 nm, 25° C.) of DNA solutions of 5 μM single-stranded DNA comprising Dss (5'-GGTAACDssATGCG-3') or double-stranded DNA comprising a Dss-Pn, Dss-Dss, Dss-Ds, or Dss-T base pair (5'-GGTAACNATGCG-3' (N=Dss) and 5'-CGCATN'GTTACC-3' (N'=Dss, Ds, Pn or T)).

Fluorescence Spectrum of Each DNA Fragment (FIG. 8)

FIG. 8 shows fluorescence spectra of DNA fragments measured with a JASCO FP-6500 spectrometer equipped with an ETC-273T temperature controller. A solution containing 5 μM of a single-stranded DNA fragment including Dss (12-mer, 5'-GGTAACN$_1$ATGCG-3', N$_1$=Dss) (SEQ ID NO: 1) or its double-stranded DNA with a complementary strand (12-mer, 5'-CGCATN$_2$GTTACC-3', N$_2$=Pn, Dss, Ds, or T) (SEQ ID NO: 2) in a 10 mM sodium phosphate buffer (pH 7.0), 100 mM NaCl, and 0.1 mM EDTA was prepared. After annealing, a fluorescence spectrum caused by excitation with light of 385 nm was measured at 25° C.

For comparison, the fluorescence spectrum of a single-stranded DNA fragment including Ds (12-mer, 5'-GGTAACN$_1$ATGCG-3', N$_1$=Ds, 5 μM) (SEQ ID NO: 3) excited with light of 310 nm at 25° C. was measured.

Example 4

Figure 9:
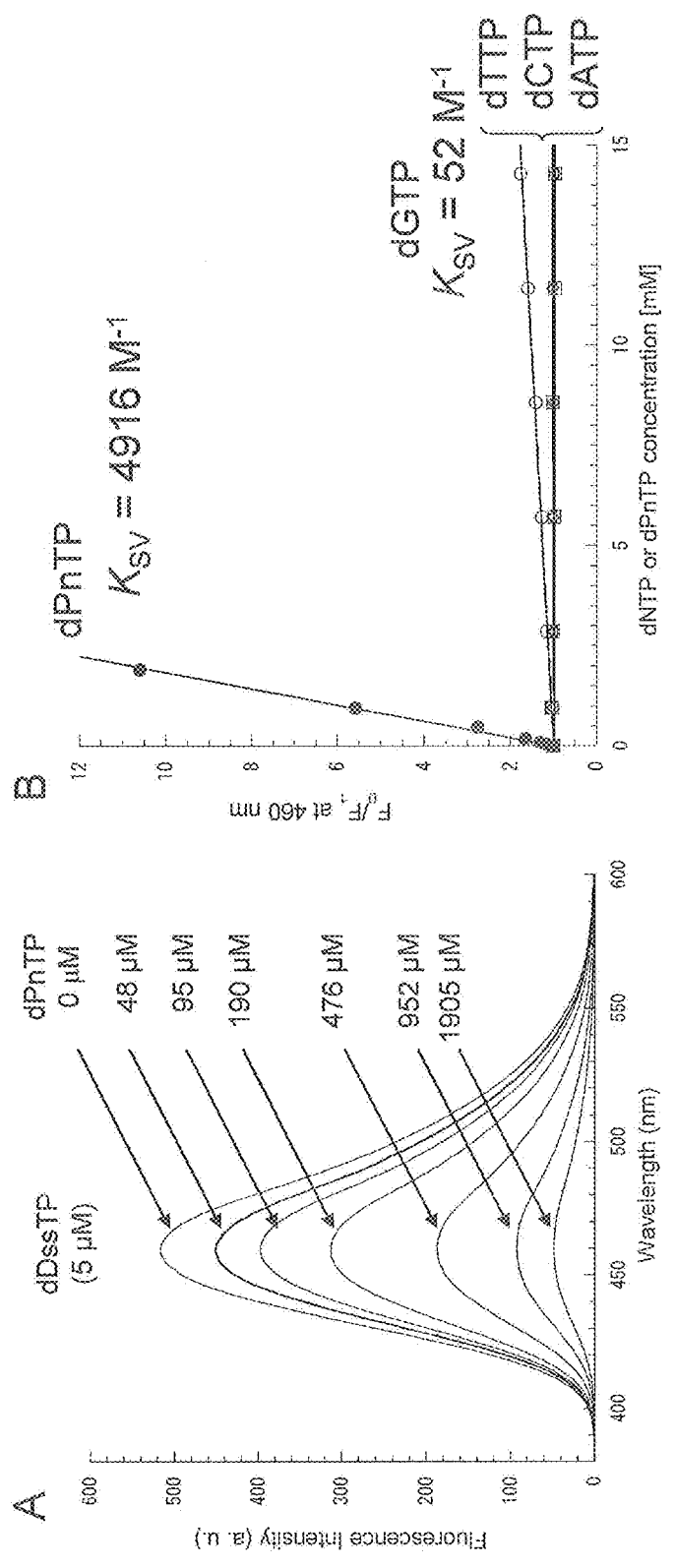
FIG. 9 shows the results of study for quenching effect of Pn. Specifically, quenching of an artificial fluorescent base Dss was investigated for dPnTP concentration dependency in an aqueous solution of a 2'-deoxyribonucleoside 5'-triphosphate derivative (dDssTP).

Quenching Effect of Pn (FIG. 9)

A. Change in Fluorescence Intensity of Deoxyribonucleoside Triphosphate of an Artificial Fluorescent Base Dss (dDssTP, 5 μM) Dependent on the Concentration of Deoxyribonucleoside Triphosphate of Pn (dPnTP)

Solutions were prepared by adding 5 μL of deoxyribonucleoside triphosphate (dDssTP, 105 μM) to solutions (100 μL) of 10 mM sodium phosphate (pH 7.0), 100 mM NaCl, and 0.1 mM EDTA containing 2, 1, 0.5, 0.2, 0.1, or 0.05 mM deoxyribonucleoside triphosphate (dPnTP). The emission spectrum of dDssTP by excitation with light of 370 nm was measured with a JASCO FP-6500 spectrometer equipped with an ETC-273T temperature controller at 20° C.

Similarly, in order to investigate the fluorescence-quenching effect of dDssTP in the presence of deoxyribonucleoside triphosphate of a natural base, solutions were prepared by adding 5 μL of deoxyribonucleoside triphosphate (dDssTP, 105 μM) to solutions (100 μL) of 10 mM sodium phosphate (pH 7.0), 100 mM NaCl, and 0.1 mM EDTA containing 15, 12, 9, 6, 3, or 1 mM deoxyriboadenosine triphosphate (dATP), deoxyriboguanosine triphosphate (dGTP), deoxyribothymidine triphosphate (dTTP), or deoxyribocytidine triphosphate (dCTP). The emission spectrum of dDssTP by excitation with light of 370 nm was measured at 20° C.

B. Comparison of Quenching Activity of dPnTP and Triphosphate of a Natural Base Against Dss Quenching of nucleoside triphosphate of an artificial fluorescent base dDssTP (5 μM) by deoxyribonucleoside triphosphate of Pn and deoxyribonucleoside triphosphate of a natural base was analyzed by steady-state Stern-Volmer plot. Specifically, emission spectra (370 nm excitation) were measured in a 10 mM sodium phosphate buffer (pH 7.0) solution containing 100 mM NaCl and 0.1 mM EDTA at 20° C. The decrease in fluorescence intensity with the concentration of a quencher (dPnTP, dATP, dGTP, dCTP, or dTTP) present in the system was substituted for the following Stern-Volmer expression to calculate the Stern-Volmer constant ($K_{SV}$):

$$F_0/F_1 = 1 + K_{SV}[Q].$$ Stern-Volmer expression:

Here, $F_0$ represents the fluorescence intensity when no quencher is present; $F_1$ represents the fluorescence intensity when a quencher is present; and [Q] represents the concentration of the quencher. Specifically, the $K_{SV}$ was determined from the straight line obtained by a least-squares method from plots of the $F_0/F_1$ values on the vertical axis for the quencher concentrations [Q] on the horizontal axis. A larger $K_{SV}$ value indicates a higher quenching activity of a quencher. It was revealed that the quenching activity of Pn is higher than that of a guanine base, which is known to have a quenching activity.

Example 5

Quenching of the Fluorescence of dDss by dPn and Derivatives Thereof (FIG. 10)

FIG. 10 shows the results of fluorescence measurement of dDss in the final concentration of 5 μM in the presence of 2.5 mM or 5 mM dPn or each derivative thereof at an excitation wavelength of 385 nm and a measurement temperature of 25° C. Specifically, nucleoside solutions (20 μM dDss and 20 mM dPn or each derivative thereof) were prepared by the following procedure.

About 5 mg of dDss, dPn, or a derivative of dPn was dried at 55 to 60° C. for 6 hours and was then weighed. An aqueous 20% acetonitrile solution was added to dDss, dPn, or a derivative of dPn such that the concentration of dDss was 2 mM and the concentration of dPn or a derivative thereof was 20 mM. The dDss solution was further diluted to 20 μM. In order to prepare samples for measuring fluorescence spectra, for a final concentration of dPn or its derivative of 2.5 mM (FIG. 10A), 50 μL of a 20 μM dDss solution, 25 μL of a solution of 20 mM dPn or its derivative, 25 μL of a 20% acetonitrile solution, and 100 μL of ethanol were mixed into a total volume of 200 μL. For a final concentration of dPn or its derivative of 5 mM (FIG. 10B), 50 μL of a 20 μM dDss solution, 50 μL of a solution of 20 mM dPn or its derivative, and 100 μL of ethanol were mixed into a total volume of 200 μL.

Example 6

Experiment of Single-Base Incorporation into DNA of a Dss-Pn Base Pair Using a Klenow Fragment (Table 1)

An experiment of single-base incorporation by a Klenow fragment was performed with reference to documents (Kimoto, M., Yokoyama, S., Hirao, I., Biotechnol. Lett., 2004, 26, 999-1005; Petruska, J., Goodman, M. F., Boosalis, M. S., Sowers, L. C., Cheong, C., Tinoco, I., Proc. Natl. Acad. Sci. USA, 1988, 85, 6252-6256; Goodman, M. F., Creighton, S., Bloom, L. B., Petruska, J., Crit. Rev. Biochem. Mol. Biol., 1993, 28, 83-126; Morales, J. C., Kool, E. T., Nat. Struct. Biol., 1998, 5, 950-954).

Specifically, a primer (20-mer, 5'-ACTCACTATAGG-GAGGAAGA-3' (SEQ ID NO: 4) or 5'-ACTCACTATAGG-GAGCTTCT-3' (SEQ ID NO: 5)) labeled with 6-carboxyfluorescein at the 5' end and a template DNA (35-mer, 5'-AGCTCTDssTCTTCCTCCCTATAGT- GAGTCGTATTAT-3' (SEQ ID NO: 6) or 5'-TCGAGANA-GAAGCTCCCTATAGTGAGTCGTATTAT-3' (N=Pn, A, G, C, or T) (SEQ ID NO: 7)) were heated in a 100 mM Tris-HCl buffer (pH 7.5) containing 20 mM $MgCl_2$, 2 mM DTT, and 100 μg/mL bovine serum albumin (BSA) at 95° C. and were then gradually cooled to 4° C. for annealing to form a double strand of the template and the primer.

An enzyme solution (2 μL) of a Klenow fragment not having exonuclease activity (KF exo–, Amersham USB) was added to 5 μL of each primer-template double-stranded DNA solution (10 μM). The mixture was incubated at 37° C. for 2 minutes to form a DNA/enzyme complex. To this solution, 3 μL of each substrate solution, i.e., nucleoside triphosphate solution (Dss, Pn, or one of A, G, C, and T, 1 μM to 5 mM) was added, followed by an enzyme reaction at 37° C. (for 1 to 35 minutes). The reaction was terminated by adding 10 μL of a 20 mM EDTA solution in 95% formamide (stop solution) to the reaction solution and heating the solution at 75° C. for 3 minutes.

The reaction conditions are summarized as follows. For each solution (10 μL), 5 μM primer-template double strand, 5 to 50 nM enzyme, and 0.3 to 1500 μM substrate are used. The solution (10 μL) contains 50 mM Tris-HCl (pH 7.5), 10 mM $MgCl_2$, 1 mM DTT, and 0.05 mg/mL BSA. The reaction is performed at 37° C. for 1 to 35 minutes.

A part of the reaction solution was diluted with the stop solution, and 0.5 μL of the diluted reaction solution was mixed with 3 μL of a loading solution (deionized formamide: 50 mg/mL blue dextran solution containing 25 mM EDTA=5: 1). The solution mixture was heated at 90° C. for 2 minutes and then was rapidly cooled on ice. About 0.5 μL of the solution was loaded on every other lane of a sequencing gel for electrophoresis. The sequencing gel (36 cm WTR) was composed of 6 M urea, 10% polyacrylamide (acrylamide: bisacrylamide=19:1), and 0.5×TBE. The buffer used for the electrophoresis was 0.5×TBE. The Run Module was GS Run 36C-2400. The time for electrophoresis was about 1 hour, and the peak patterns of the reaction products were analyzed and quantitatively measured by an automated ABI377 DNA sequencer equipped with GeneScan software (version 3.0).

The proportion of the primer extended by one nucleotide was determined from the peak area of the unreacted primer fragment and the peak area of the DNA fragment extended by single-base incorporation, and enzymatic parameters $V_{max}$ and $K_M$ were calculated by Hanes-Woolf plot (Goodman, M. F., Creighton, S., Bloom, L. B., Petruska, J., Crit. Rev. Biochem. Mol. Biol., 1993, 28, 83-126). The $V_{max}$ value was standardized to 20 nM enzyme concentration and 5 μM double strand concentration for various enzyme and double-strand concentrations used.

Table 1 shows the results.

TABLE 1

Experiment of single-base incorporation into DNA of Dss-Pn base pair using Klenow fragment Primer 5'-ACTCACTATAGGGAGCTTCT
temp35N-1 3'-TATTATGCTGAGTGATATCCCTCGAAGA<u>N</u>AGAGCT

| Entry | Template (N) | Nucleoside triphosphate | $K_M$ (μM) | $V_{max}$ (% $min^{-1}$) | Efficiency $(V_{max}/K_M)^d$ |
|---|---|---|---|---|---|
| 1 | Pn | dDssTP | 0.77 (0.2)[b] | 8.9 (3.0) | 1.2 × 10^7 |
| 2 | A | dDssTP | 5.0 (2.4) | 0.73 (0.1) | 1.5 × 10^5 |
| 3 | G | dDssTP | 3.6 (0.2) | 0.93 (0.03) | 2.6 × 10^5 |
| 4 | C | dDssTP | 7.5 (1.8) | 1.0 (0.2) | 1.3 × 10^5 |
| 5 | T | dDssTP | 6.2 (0.1) | 2.2 (0.2) | 3.5 × 10^5 |
| 6 | T | dATP | 0.81 (0.44) | 3.3 (1.8) | 4.0 × 10^6 |

Primer 5'-ACTCACTATAGGGAGGAAGA
temp35N-1 3'-TATTATGCTGAGTGATATCCCTCCTTCT<u>N</u>TCTCGA

| Entry | Template (N) | Nucleoside triphosphate | $K_M$ (μM) | $V_{max}$ (% $min^{-1}$) | Efficiency $(V_{max}/K_M)^d$ |
|---|---|---|---|---|---|
| 1 | Dss | dPnTP | 100 (20)[b] | 11 (3) | 1.1 × 10^5 |
| 2 | Dss | dATP | n.d.[c] | n.d.[c] | |
| 3 | Dss | dGTP | n.d. | n.d. | |
| 4 | Dss | dCTP | n.d. | n.d. | |
| 5 | Dss | dTTP | n.d. | n.d. | |
| 6 | A | dTTP | 0.7 (0.4) | 2.8 (1.5) | 4.0 × 10^6 | a: Assays were carried out at 37° C. for 1 to 35 mM using 5 μM template-primer duplex, 5 to 50 nM enzyme, and 0.3 to 1500 μM nucleoside triphosphate in a solution (10 μL) containing 50 mM Tris-HCl (pH 7.5), 10 mM $MgCl_2$, 1 mM DTT, and 0.05 mg/mL bovine serum albumin. Each parameter was an averaged value of three to eight data sets.
[b]Standard deviations are given in parentheses.
[c]Not determined. Minimal inserted products (<2%) were detected after an incubation for 20 mM with 1500 μM nucleoside triphosphate and 50 nM enzyme.
[d]The units of this term are % $min^{-1}$ $M^{-1}$.

Example 7

Primer Extension Reaction by Template DNA Containing Pn and dDssTP Using a Klenow Fragment of DNA Polymerase I Derived from *Escherichia coli* (FIG. 11)

A primer (23-mer) (SEQ ID NO: 8) labeled with $^{32}$P at the 5' end and a template DNA containing Pn or Pa (35-mer) (SEQ ID NO: 9) were heated at 95° C. in a 20 mM Tris-HCl (pH 7.5) buffer containing 14 mM MgCl$_2$ and 0.2 mM DTT and were then gradually cooled to 4° C. for annealing to form a double strand of the template and the primer. A substrate solution (2.5 μL), i.e., a nucleoside triphosphate solution (40 μM dCTP, 40 μM dTTP, and 0 to 40 μM dDssTP) was added to 5 μL of each primer-template double-stranded DNA solution (400 nM) on ice. To the solution added was an enzyme solution (2.5 μL, one unit) of a Klenow fragment having exonuclease activity (KF exo+, TaKaRa) diluted with sterilized water for starting a reaction. After incubation at 37° C. for 3 minutes, the reaction was terminated by adding 10 μL of 1×TBE solution (stop solution) containing 10 M urea and heating at 75° C. for 3 minutes. The reaction products were electrophoresed on a 15% polyacrylamide/7 M urea gel, and the band pattern was analyzed by autoradiography with a bioimaging analyzer (FLA7000, Fujifilm).

Example 8

PCR Amplification of DNA Including Ds Using a Dss-Px Base Pair (FIG. 12)

PCR was performed using a template DNA including Ds (S2, 55-mer) or a DNA composed of only natural bases (control, 55-mer) in the presence of predetermined concentrations of artificial base substrates, NH$_2$-hx-dPxTP and dDssTP. The products were analyzed by electrophoresis. The results are shown in FIG. 12.

The sequences of the template DNAs and primers used are as follows.

```
DNA S2 (55-mer, annealing sites of the primer is underlined):
                                                    (SEQ ID NO: 10)
5'-TTTCACACAGGAAACAGCTATGACGGCCCDsTTGCCCTATAGTGAGTCGTATTATC-3'

DNA control (55-mer, annealing sites of the primer is underlined):
                                                    (SEQ ID NO: 11)
5'-TTTCACACAGGAAACAGCTATGACGGATCCATTCCCTATAGTGAGTCGTATTATC-3'

5' primer:
                                                    (SEQ ID NO: 12)
5'-CGTTGTAAAACGACGGCCAGGATAATACGACTCACTATAG-3'

3' primer:
                                                    (SEQ ID NO: 13)
5'-TTTCACACAGGAAACAGCTATGAC-3'
```

PCR (reaction scale: 40 μL) was performed with a DNA fragment at a final concentration of 0.4 nM as a template by 20 cycles of 94° C. for 30 sec, 45° C. for 30 sec, and 65° C. for 4 min. The final reaction solution was composed of 20 mM Tris-HCl (pH 8.8), 10 mM KCl, 10 mM (NH$_4$)$_2$SO$_4$, 2 mM MgSO$_4$, 0.1% Triton X-100, DeepVent DNA polymerase (0.02 units/μL, NEB), 1 μM of the 5' primer, 1 μM of the 3' primer, 0.3 mM each natural base substrate dNTP, 10 to 25 μM dDssTP, and 25 μM NH$_2$-hx-dPxTP. The PCR products after 20 cycles were electrophoresed on a 15% polyacrylamide/7 M urea gel.

The gel was stained with SYBR Green II (Lonza), and the band of amplified DNA was detected with a bioimager LAS4000 (Fujifilm) at the SYBR mode.

Example 9

Sequencing of DNA after PCR Amplification Using Dss-Px Base Pair (FIG. 13)

PCR was performed using a template DNA including Ds (S2, 55-mer) in the presence of predetermined concentrations of artificial base substrates, NH$_2$-hx-dPxTP and dDssTP. Whether the artificial base Dss was maintained in the products was analyzed by DNA sequencing using an artificial base substrate dPa'TP or ddPa'TP. The results are shown in FIG. 13.

The sequences of the template DNAs and primers used are as follows.

```
DNA S2 (55-mer, annealing sites of the primer is underlined):
                                                    (SEQ ID NO: 10)
5'-TTTCACACAGGAAACAGCTATGACGGCCCDsTTGCCCTATAGTGAGTCGTATTATC-3'
```

-continued

PCR primer
5' primer:
(SEQ ID NO: 12)
5'-CGTTGTAAAACGACGGCCAGGATAATACGACTCACTATAG-3'

3' primer:
(SEQ ID NO: 13)
5'-TTTCACACAGGAAACAGCTATGAC-3'

Sequencing primer:
(SEQ ID NO: 14)
5'-CGTTGTAAAACGACGGCCAG-3'

PCR (reaction scale: 25 µL) was performed with a DNA fragment at a final concentration of 0.6 nM as a template by 15 cycles of 94° C. for 30 sec, 45° C. for 30 sec, and 65° C. for 4 min. The final reaction solution was composed of 20 mM Tris-HCl (pH 8.8), 10 mM KCl, 10 mM (NH$_4$)$_2$SO$_4$, 2 mM MgSO$_4$, 0.1% Triton X-100, DeepVent DNA polymerase (0.02 units/µL, NEB), 1 µM of the 5' primer, 1 µM of the 3' primer, 0.3 mM each natural base substrate dNTP, 2 to 10 µM dDssTP, and 2 to 50 µM NH$_2$-hx-dPxTP. The full-length PCR product after 15 cycles was purified with a denatured gel, and the purified product was subjected to sequence analysis as a template for DNA sequencing.

The sequencing reaction of DNA was performed using a mixture (total volume of 20 µL) of 8 µL of Cycle Sequencing Mix of a commercially available BigDye Terminator v1.1 Cycle Sequencing Kit (Applied BioSystems), a primer (4 pmol), and the PCR-amplified DNA fragment (about 0.3 pmol) by 25 cycles of PCR (96° C. for 10 sec, 50° C. for 5 sec, and 60° C. for 4 min) in the presence of 40 pmol of dPa'TP or 1 nmol of ddPa'TP. The unreacted dye terminator was removed from the reaction solution with a Centri-Sep spin column (Applied BioSystems). The resulting solution was dried by suction under reduced pressure. The residue was suspended in 4 µL of a blue Dextran solution in formamide, and a part of the suspension was analyzed with an ABI377 DNA sequencer. The gel used for the analysis was composed of 7% polyacrylamide/6 M urea gel, and the sequence peak pattern was analyzed with Applied BioSystems PRISM sequencing analysis v3.2 software.

Example 10

Real-Time PCR Using Dss-Px Base Pair (FIG. 15)

FIG. 14 shows the principle of a real-time PCR using a primer including an artificial base Dss in the presence of a substrate dPxTP.

Incorporation of Px into a complementary strand of Dss allows the Px to function as a quencher of the Dss. Accordingly, double-stranded DNA amplified by PCR can be detected from a decrease in fluorescence intensity of Dss. FIG. 15 shows the results of real-time PCR when the following DNA fragments were actually used. The results show quantitative amplification plots that indicate only three copies of DNA in the reaction solution (25 µL) can be detected.

Sequences used in the experiment (primer annealing sites are underlined)

5'-Primer sequence:
(SEQ ID NO: 15)
5'-<u>CATGTAGATGCCATCAAAGAAGCTC</u>-3'

3'-Primer sequence:
(SEQ ID NO: 16)
5'-AATAATGCDss<u>TCCTCAAAGGTGGTGACTTC</u>-3'

Double-stranded template DNA (98 bp; only one strand is shown):
(SEQ ID NO: 17)
5'-<u>CATGTAGATGCCATCAAAGAAGCTC</u>TGAGCCTCCTAAATGACATGCGTGCTCTGG
AGAACGAAAAGAACGAAGACGTA<u>GAAGTCACCACCTTTGAGGA</u>-3'

Specifically, PCR was performed with a real-time PCR machine (Stratagene Mx3005P) in the presence of 1 µM of each primer, 0.2 mM of each natural base substrate dNTP, and 2 µM of an artificial base substrate dPxTP at 94° C. for 2 min and then through 55 cycles each of consisting of two steps of 94° C. for 5 sec and 68° C. for 40 sec. The reaction scale of the PCR was 25 µL, and the reaction solution was composed of 40 mM Tricine-KOH (pH 8.0), 16 mM KCl, 3.5 mM MgSO$_4$, 3.75 µg/mL BSA, and 1× Titanium Taq DNA polymerase. The DNA fragment used as the template was diluted such that the reaction solution contained 0, 3, 15, 30, 150, 300, 1500, 3000, 15000, or 30000 copies, and PCR was performed at each concentration.

The filter set used for the detection was for an excitation wavelength of 350 nm and a fluorescence wavelength of 440 nm (for ALEXA). Data was analyzed with Plexor (registered trademark) AnalySiS Software (v1.5.4.18, Promega & Eragen BioSciences). The results are shown in FIG. 15.

Example 11

Fluorescent Characteristics DNA Hairpin Including Dss-Pn Base Pair (FIG. 16)

A 1×Ex Taq buffer (TaKaRa, containing 2 mM MgCl$_2$) containing 1 µM DNA including Dss, i.e., hairpin ssDNA (34-mer) (SEQ ID NO: 18) or ssDNA (12-mer) (SEQ ID NO: 19) was prepared. Changes in fluorescence intensity due to variable temperature were detected in the presence of a reference dye ROX (Invitrogen) (final concentration: 1000 fold dilution) with Mx3005P at the dissociation mode. FIG. 16 is a graph showing fluorescence intensities after correction with a signal intensity of ROX and normalization with the value at 35° C.

The profile of ssDNA (12-mer) in a linear strand without a hairpin structure shows gradually decreasing fluorescence as in the case of single use of the buffer (background) not containing DNA. In contrast, the profile of hairpin ssDNA (34-mer) forming a hairpin structure containing a Dss-Pn base pair shows an increase in fluorescence with temperature. This suggests that Pn having a quenching activity forms a base pair with Dss in the hairpin structure at low temperature to quench the fluorescence of Dss to reduce the fluorescence intensity and that the hairpin structure is broken at elevated temperature to lose the quenching activity to allow the detection of the fluorescence of Dss.

Example 12

Visualization of Molecular Beacon Using Dss-Pn Base Pair (FIG. 17)

A solution of 2 μM of a DNA fragment molecular beacon (MB-C, 26-mer) (SEQ ID NO: 20) and a solution of 2 μM of a DNA fragment target DNA (71G, 71-mer) (SEQ ID NO: 21) were prepared and mixed in equal volumes (each 50 μL). As a negative control, a solution not containing the target DNA was mixed with the MB-C solution. The final solution was composed of 1 μM each DNA, 10 mM sodium phosphate buffer (pH 7.0), 100 mM NaCl, and 0.1 mM EDTA. This solution was heated at 90° C. for 10 seconds with a PCR machine and was then slowly cooled to 25° C. The solution was photographed with a digital camera under irradiation with a UV-LED lamp at an excitation wavelength of 375 nm or natural light. The photographs are shown on the right in FIG. 17.

In the absence of the target DNA, the molecular beacon forms a loop-stem structure to quench the fluorescence of Dss by formation of the Dss-Pn base pair. In contrast, in the presence of the target DNA, the loop region of the molecular beacon forms a double strand with the target DNA by hybridization to break the stem structure to lose the Dss-Pn base pair. As a result, the fluorescence of Dss was detected by visual observation.

Example 13

Detection of Single-Nucleotide Mutation with a Molecular Beacon Using a Dss-Pn Base Pair (FIG. 18)

A molecular beacon (26-mer, MB-C (SEQ ID NO: 20) or MB-T (SEQ ID NO: 23)) solution (50 μL) diluted to 500 nM was mixed with a target DNA fragment (71-mer, 71G (SEQ ID NO: 21) or 71A (SEQ ID NO: 22), 12.5 μL) in a concentration of five times the final solution to prepare a sample. The sample was warmed at 45° C. for 5 minutes or more in an incubator to obtain an equilibrium state. Fluorescence was measured with a JASCO FP-6500 spectrometer. The solution was transferred to a cell and was left in the apparatus (at 45° C.) for 2 minutes, and fluorescence spectrum of 430 to 470 nm was measured by exciting with light of 390 nm by automated shutter control. The final solution was composed of 400 nM molecular beacon, 0 to 3200 nM target DNA, 10 mM sodium phosphate buffer (pH 7.0), 100 mM NaCl, and 0.1 mM EDTA.

FIG. 18 is a graph plotting the fluorescence intensity at 454 nm normalized by the fluorescence intensity in the absence of the target DNA fragment. The results show that single-nucleotide mutation can be detected with a molecular beacon using a Dss-Pn base pair on the basis of that single-base mismatch significantly decreases fluorescence intensity compared with that in a completely complementary strand.

Example 14

Visualization of PCR Using Cy3-Px/Dss Base Pair (FIG. 20)

FIG. 19 shows the principle of real-time PCR using a primer including an artificial base Dss in the presence of a substrate Cy3-hx-dPxTP. Cy3-hx-dPx is incorporated into a complementary strand of Dss to cause FRET between Dss and Cy3 by irradiation with light of approximately 350 nm, resulting in specific emission of double-stranded DNA amplified by PCR. The fluorescence by the FRET was visually detected (FIG. 20).

The sequences of strands used in this experiment are the same as those shown in FIG. 15.

Sequences used in the experiment (primer annealing sites are underlined)

```
5'-Primer sequence:
                                              (SEQ ID NO: 15)
5'-CATGTAGATGCCATCAAAGAAGCTC-3'

3'-Primer sequence:
                                              (SEQ ID NO: 16)
5'-AATAATGCDssTCCTCAAAGGTGGTGACTTC-3'

Double-stranded template DNA (98 bp; only one strand is shown):
                                              (SEQ ID NO: 17)
5'-CATGTAGATGCCATCAAAGAAGCTCTGAGCCTCCTAAATGACATGCGTGCTCTGG

AGAACGAAAAGAACGAAGACGTAGAAGTCACCACCTTTGAGGA-3'
```

Specifically, PCR was performed with a real-time PCR machine (Stratagene Mx3005P) in the presence of 1 μM of each primer, 0.2 mM of each natural base substrate dNTP, and 2 μM of an artificial base substrate Cy3-hx-dPxTP at 94° C. for 2 mM and then through 55 cycles each consisting of two steps of 94° C. for 5 sec and 68° C. for 40 sec. The reaction scale of the PCR was 25 μL, and the reaction solution was composed of 40 mM Tricine-KOH (pH 8.0), 16 mM KCl, 3.5 mM MgSO$_4$, 3.75 μg/mL BSA, and 1× Titanium Taq DNA polymerase. The DNA fragment used as the template was diluted such that the reaction solution contained 0, 3, 30, 300, 3000, 30000, 300000, or 3000000 copies, and PCR was performed at each concentration. The reaction tube was directly irradiated with UV light of 365 nm, and fluorescence was visually detected through an orange filter.

Example 15

Real-Time PCR by Fluorescent Molecule Cy3-Linked Px Base with Quenching Activity (FIG. 22)

FIG. 21 shows the principle of real-time PCR using a primer including an artificial base Ds in the presence of a substrate dPxTP derivative including fluorescent molecule (e.g., Cy3). Linking of a fluorescent molecule to a Px base having a quenching activity quenches the fluorescence intensity of the fluorescent molecule by about 30%. When a substrate (Cy3-hx-dPxTP) is used in PCR using a primer including a Ds base, Cy3-hx-dPx is incorporated in a DNA to increase the fluorescence intensity of the Cy3. FIG. 22 shows the results of real-time PCR when the following DNA fragments were actually used. The results show quantitative amplification plots that indicate only three copies of DNA in the reaction solution (25 μL) can be detected.

Sequences used in the experiment (primer annealing sites are underlined):

```
5'-Primer sequence:
                                              (SEQ ID NO: 15)
5'-CATGTAGATGCCATCAAAGAAGCTC-3'

3'-Primer sequence:
                                              (SEQ ID NO: 24)
5'-AATAATGCDsTCCTCAAAGGTGGTGACTTC-3'

Double-stranded template DNA (98 bp; only one strand is shown):
                                              (SEQ ID NO: 17)
5'-CATGTAGATGCCATCAAAGAAGCTCTGAGCCTCCTAAATGACATGCGTGCTCTGG

AGAACGAAAAGAACGAAGACGTAGAAGTCACCACCTTTGAGGA-3'
```

Specifically, PCR was performed with a real-time PCR machine (Stratagene Mx3005P) in the presence of 1 μM of each primer, 0.2 mM of each natural base substrate dNTP, and 2 μM of an artificial base substrate Cy3-hx-dPxTP at 94° C. for 2 min and then through 55 cycles each consisting of two steps of 94° C. for 5 sec and 68° C. for 40 sec. The reaction scale of the PCR was 25 μL, and the reaction solution was composed of 40 mM Tricine-KOH (pH 8.0), 16 mM KCl, 3.5 mM MgSO₄, 3.75 mg/mL BSA, and 1× Titanium Taq DNA polymerase. The DNA fragment used as the template was diluted such that the reaction solution contained 0, 3, 30, 300, 3000, 30000, 300000, or 3000000 copies, and PCR was performed at each concentration. The filter set used for the detection was for an excitation wavelength of 545 nm and a fluorescence wavelength of 568 nm (for Cy3). Data was analyzed with the attached analysis software MxPro version 4.10.

Example 16

Detection of Real-Time PCR Products by Fluorescent Molecule Cy3-Linked Px with Quenching Activity on Electrophoretic Gel (FIG. 23)

Since Cy3 is incorporated in the PCR product shown in FIG. 22, the PCR product can be detected by agarose gel electrophoresis with the fluorescence of Cy3 on the gel without conventional DNA staining with, for example, EtBr or SYBR Green. FIG. 23 shows the results of detecting band patterns in 4% agarose gel electrophoresis of 12 μL of the PCR product shown in FIG. 22 with a bioimaging analyzer, FLA7000 (Fujifilm) at a Cy3 detection mode (excitation laser: 532 nm, detection filter: 0580).

Example 17

Fluorescent Characteristics of DNA Including Fluorescent Molecule Cy3 and Artificial Fluorescent Base s (FIG. 24)

The concentrations of DNA fragments chemically synthesized and purified by HPLC were each adjusted to a final concentration of 5 μM with a 10 mM sodium phosphate buffer (pH 7) containing 100 mM NaCl and 0.1 mM EDTA. FIG. 24 shows the results of investigation on fluorescent characteristics of these solutions by visual observation and fluorescence spectra.

UV irradiation was performed from below with an UV transilluminator. The DNA fragment containing one artificial fluorescent base s emitted light by irradiation with light of 254 nm, 302 nm, and 365 nm (photograph of Lane 2), and the fluorescence was quenched by introducing two adjacent "s"'s to the DNA (photograph of Lane 3). The DNA containing Cy3 slightly emitted fluorescent light by irradiation with light of 254 nm and 302 nm, but hardly emitted fluorescent light by irradiation with light of 365 nm (photograph of Lane 4). The fluorescence of Cy3 was observed by introducing one or two "s"'s near Cy3 in the DNA to confirm the occurrence of FRET (photographs of Lanes 5 to 7). The graph shows the fluorescence spectra when the solutions were excited with light of 365 nm

Example 18

Visualization of PCR by a Combination of Fluorescent Molecule Cy3-Linked Px Base with Quenching Activity and Artificial Fluorescent Base s (FIGS. 26 to 28)

FIG. 25 shows the principle of real-time PCR using a primer including an artificial base Ds and two adjacent artificial fluorescent bases "s"'s in the presence of a substrate Cy3-hx-dPxTP. The fluorescence of "s"'s is completely quenched by introducing them so as to be adjacent to each other; however, combination of arrangement of Ds near the "s"'s and specific incorporation of Cy3-hx into the double-stranded DNA by complementation to the Ds causes FRET between the s's and the Cy3 by irradiation with light of approximately 365 nm, which allows only the double-stranded DNA amplified by PCR to specifically emit light.

FIG. 26 shows the results of visual observation of the product by 25 cycles of PCR actually using the following DNA fragments. In the system using ss-Cy3 shown in FIG.

26, PCR was performed with a PCR machine (MJ Research, PTC-100) in the presence of 1 μM of each primer, 0.2 mM of each natural base substrate dNTP, and 2 μM of an artificial base substrate Cy3-hx-dPxTP at 94° C. for 2 min and then through 25 cycles each consisting of two steps of 94° C. for 5 sec and 68° C. for 40 sec. The reaction scale of the PCR was 25 μL, and the reaction solution was composed of 40 mM Tricine-KOH (pH 8.0), 16 mM KCl, 3.5 mM MgSO$_4$, 3.75 μg/mL BSA, and 1× Titanium Taq DNA polymerase. The concentration of the DNA fragment used as the template was 0.5 nM. In the conventional PCR performed in the presence of SYBR Green I, SYBR Green I (final concentration: 1/30000), instead of the 2 μM artificial base substrate Cy3-hx-dPxTP, and ROX (final concentration: 1/500), as a reference dye, were used.

Real-time PCR detection in the presence of SYBR Green I is one of the methods that have been most widely employed, but, as shown in the photographs on the two lanes on the right side in FIG. 26, the change in fluorescence between the presence and the absence of DNA is not noticeable and therefore cannot be visually detected. In contrast, in the method of the present invention, PCR can be visually detected, as shown in the two lanes on the left side in FIG. 26.

In the real-time PCR shown in FIG. 27a, PCR was performed with a real-time PCR machine (Stratagene Mx3005P) in the presence of 1 μM of each primer, 0.2 mM of each natural base substrate dNTP, and 2 μM of an artificial base substrate Cy3-hx-dPxTP at 94° C. for 2 min and then through 55 cycles each consisting of two steps of 94° C. for 5 sec and 68° C. for 40 sec. The reaction scale of the PCR was 25 μL, and the reaction solution was composed of 40 mM Tricine-KOH (pH 8.0), 16 mM KCl, 3.5 mM MgSO$_4$, 3.75 μg/mL BSA, and 1× Titanium Taq DNA polymerase. The DNA fragment used as the template was diluted such that the reaction solution contained 0, 3, 30, 300, 3000, 30000, 300000, or 3000000 copies, and PCR was performed at each concentration.

Furthermore, as shown in FIG. 27a, it was revealed that PCR products from only three copies of DNA in a reaction solution (25 μL) can be visually detected by irradiation with light of 365 nm Furthermore, FIG. 28 shows the results of agarose gel electrophoresis of visualized PCR products shown in FIG. 27a. The results show that a product can be detected through FRET from s to Cy3 caused by irradiation with light of 312 nm and that a product can be detected through fluorescence of Cy3 directly incorporated into DNA by irradiation with light of 532 nm Sequences used in the experiment (primer annealing sites are underlined)

FIG. 28 shows the electrophoretic results of 12 μL of the PCR product shown in FIG. 27a on a 4% agarose gel when the product was detected through FRET between s and Cy3 with a bioimaging analyzer, LAS4000 (Fujifilm), at an EtBr detection mode (excitation: 312 nm, transparent UV detection filter: 605DF40) and when the product was directly detected by fluorescence of Cy3 with FLA7000 (Fujifilm) at a Cy3 detection mode (excitation laser: 532 nm, detection filter: O580).

Example 19

Visualization of PCR Using a Combination of Fluorescent Molecule Cy3-Linked Px Base with Quenching Activity: Quantitative Determination of Fluorescence Intensity at Respective PCR Cycles (FIGS. 27b to 27d)

This Example is a supplementary experiment of the experiment shown in FIG. 27a.

PCR using a primer including an artificial base Ds and two adjacent artificial fluorescent bases "s"'s in the presence of a Cy3-hx-dPxTP substrate can be utilized in real-time PCR (FIG. 27b) by measuring an increase in fluorescence intensity of Cy3 in the amplified DNA. In addition, a difference in initial concentrations of DNA can be visually detected by PCR amplification of the DNA (FIG. 27c). Furthermore, amplification of DNA can be quantified by processing photographed images of tubes in the amplification process of respective PCR cycles (FIG. 27d).

Sequences used in the experiment (primer annealing sites are underlined):

```
5'-Primer sequence:
                                                (SEQ ID NO: 15)
5'-CATGTAGATGCCATCAAAGAAGCTC-3'

3'-Primer sequence:
                                                (SEQ ID NO: 25)
5'-AATAASSGCDsTCCTCAAAGGTGGTGACTTC-3'

Double-stranded template DNA (98 bp; only one strand is shown):
                                                (SEQ ID NO: 17)
5'-CATGTAGATGCCATCAAAGAAGCTCTGAGCCTCCTAAATGACATGCGTGCTCTGG

AGAACGAAAAGAACGAAGACGTAGAAGTCACCACCTTTGAGGA-3'
```

```
5'-Primer sequence:
                                                           (SEQ ID NO: 15)
5'-CATGTAGATGCCATCAAAGAAGCTC-3'

3'-Primer sequence:
                                                           (SEQ ID NO: 26)
5'-AATAAssGCDsTCCTCAAAGGTGGTGACTTC-3'

Double-stranded template DNA (98 bp; only one strand is shown):
                                                           (SEQ ID NO: 17)
5'-CATGTAGATGCCATCAAAGAAGCTCTGAGCCTCCTAAATGACATGCGTGCTCTGG

AGAACGAAAAGAACGAAGACGTAGAAGTCACCACCTTTGAGGA-3'
```

PCR was performed with a real-time PCR machine (Stratagene Mx3005P) in the presence of 1 µM of each primer, 0.2 mM of each natural base substrate dNTP, and 2 µM of an artificial base substrate Cy3-hx-dPxTP at 94° C. for 2 min and then through 30, 35, 40, 45, or 55 cycles each consisting of two steps of 94° C. for 5 sec and 68° C. for 40 sec.

The reaction scale of the PCR was 25 µL, and the reaction solution was composed of 40 mM Tricine-KOH (pH 8.0), 16 mM KCl, 3.5 mM MgSO₄, 3.75 lag/mL BSA, and 1× Titanium Taq DNA polymerase. The DNA fragment used as the template was diluted such that the reaction solution contained 0, 3, 30, 300, 3000, 30000, 300000, or 3000000 copies, and PCR was performed at each concentration.

For quantitative analysis, images of a tube after completion of the reaction was processed by the following procedure: The tube was photographed with a digital camera through an UV cut filter and an orange filter under irradiation with UV of 365 nm from below with a UV transilluminator, and the resulting file (JPEG format) was converted to a TIFF format file with Adobe Photoshop ver. 6.0 so that the image mode is a gray scale and the resolution is 72 pixel/inch. This file was read with Science Lab 2005 Multi Gauge software for quantitative analysis. Specifically, the background value (average of seven points in the area between tubes) was subtracted from the quantum level (QL value) at portion [1015(pixel)²] of the reaction solution of the tube, and the resulting value per unit area was plotted for the PCR cycles or the number of copies used as the template to show the results as a graph.

FIGS. 27b to 27d show the results.

FIG. 29a shows the principle of real-time PCR using a primer including two adjacent modified bases (s-hx-dU)s, each being a natural base U to which an artificial fluorescent base is linked via a linker, in the presence of a substrate Cy3-hx-dPxTP. The fluorescence of s is quenched when two (s-hx-dU)s are adjacent to each other; however, combination of arrangement of Ds near the (s-hx-dU)s and specific incorporation of Cy3-hv-dPx into the double-stranded DNA by the complementation to the Ds causes FRET between the s of the s-hx-dU and the Cy3 by irradiation with light of approximately 365 nm, which allows only the double-stranded DNA amplified by PCR to specifically emit light, as in the case of two adjacent "s"'s (FIG. 25). In the case shown in FIG. 25, since the primer includes two s bases, the synthesis of a complementary strand by PCR may stop at this site. In this method, however, since s is linked to a natural base via a linker, the synthesis of a complementary strand by PCR proceeds. Accordingly, a portion containing an artificial dye for color development can be introduced to any site of a primer, and the method can be used in PCR such as LAMP or SMAP. In addition, the method can be applied to a strand other than primer regions, such as padlock PCR.

FIG. 29b shows the DNA sequences used and conditions for PCR. FIG. 29c shows the results of real-time PCR by 55 cycles, and FIG. 29d shows the results of visual observation of amplified products after PCR by 55 cycles. The PCR amplification was performed using the DNA as a target (target DNA) in an amount ranging from 0 to 3000000 copies to confirm that DNA was visually observed from three or more copies of DNA.

Sequences used in the experiment (primer annealing sites are underlined; Us=s-hx-dU):

```
5'-Primer sequence:
                                                           (SEQ ID NO: 15)
5'-CATGTAGATGCCATCAAAGAAGCTC-3'

3'-Primer sequence:
                                                           (SEQ ID NO: 27)
5'-AATAAUsUsGCDsTCCTCAAAGGTGGTGACTTC-3'

Double-stranded template DNA (98 bp; only one strand is shown):
                                                           (SEQ ID NO: 17)
5'-CATGTAGATGCCATCAAAGAAGCTCTGAGCCTCCTAAATGACATGCGTGCTCTGG

AGAACGAAAAGAACGAAGACGTAGAAGTCACCACCTTTGAGGA-3'
```

Example 20

Detection of PCR Product Using Nucleoside Derivative (s-hx-DU), a Natural Base to which a Fluorescent Molecule (s Base) is Linked Via a Linker, and Ds-Px Base Pair (FIGS. 29b to 29d)

This Example is supplementary experiment of the experiment shown in FIG. 29a.

Specifically, PCR was performed with a real-time PCR machine (Stratagene Mx3005P) in the presence of 1 µM of each primer, 0.2 mM of each natural base substrate dNTP, and 2 µM of an artificial base substrate Cy3-hx-dPxTP at 94° C. for 2 min and then through 55 cycles each consisting of two steps of 94° C. for 5 sec and 68° C. for 40 sec. The reaction scale of the PCR was 25 µL, and the reaction solution was composed of 40 mM Tricine-KOH (pH 8.0), 16 mM KCl, 3.5 mM MgSO₄, 3.75 µg/mL BSA, and 1× Titanium Taq DNA polymerase. The DNA fragment used as the template was diluted such that the reaction solution contained 0, 3, 30, 300, 3000, 30000, 300000, or 3000000 copies, and PCR was performed at each concentration. The reaction tube was directly irradiated with UV light of 365 nm, and fluorescence was visually detected through an orange filter.

Example 21

Chemical Synthesis of s-Hx-dU Amidite Reagent (Compound Shown in FIG. 6) (FIG. 30)

Synthesis of 8-bromo-1-octyne (step (a) in FIG. 30)

Dehydrated dichloromethane (20 mL) and triphenylphosphine (5.91 g, 22.5 mmol) were added to 8-hydroxy-1-octyne (1.95 g, 15 mmol). The mixture was cooled to 0° C. and was then dropwise added to dehydrated dichloromethane (10 mL) containing carbon tetrabromide (7.46 g, 22.5 mmol), followed by stirring at room temperature for 2 hours. After separation between dichloromethane (100 mL) and 5% sodium bicarbonate (150 mL), the organic layer was washed with saturated brine (150 mL). The organic layer was dried over sodium sulfate and then concentrated. The concentrated product was purified by silica gel column chromatography (dichloromethane:methanol=from 100:0 to 99:1) to yield 8-bromo-1-octyne (crude).

Physical properties of 8-bromo-1-octyne $^1$H NMR (300 MHz, DMSO-d6) δ 3.51 (t, 2H, J=6.7 Hz), 2.71 (t, 1H, J=2.7 Hz), 2.12-2.17 (m, 2H), 1.75-1.84 (m, 2H), 1.24-1.54 (m, 6H).

2) Synthesis of 6-(thien-2-yl)-9-(7-octynyl)-2-amino purine (step (b) in FIG. 30)

8-Bromo-1-octyne (2.0 g, 10.6 mmol) prepared in step 1) was added to a dehydrated dimethylformamide (25 mL) solution containing 6-(thien-2-yl)-2-amino purine (1.2 g, 5.5 mmol) and potassium carbonate (2.3 g, 16.5 mmol), followed by stirring at room temperature for 15 hours. The reaction solution was concentrated and was separated between ethyl acetate and water. The organic layer was washed with saturated brine, was dried over anhydrous sodium sulfate, and was purified by medium-pressure preparative column chromatography to yield 6-(thien-2-yl)-9-(7-octynyl)-2-amino purine (1.6 g, 4.9 mmol, 87%).

Physical properties of 6-(thien-2-yl)-9-(7-octynyl)-2-amino purine $^1$H NMR (300 MHz, DMSO-d6) δ 8.53 (dd, 1H, J=1.2, 3.7 Hz), 8.14 (s, 1H), 7.79 (dd, 1H, J=1.2, 5.0 Hz), 7.26 (dd, 1H, J=3.7, 5.0 Hz), 6.48 (brs, 2H), 4.05 (t, 2H, J=7.2 Hz), 2.72 (t, 1H, J=2.6 Hz), 2.12 (m, 2H), 1.78 (m, 2H), 1.23-1.46 (m, 6H).

3) Synthesis of 6-(thien-2-yl)-9-(7-octynyl)-2-phenoxyacetamide purine (step (c) in FIG. 30)

1-Hydroxybenzotriazole (1.19 g, 8.84 mmol) was azeotropically dried with dehydrated pyridine three times. Dehydrated pyridine (2.5 mL), dehydrated acetonitrile (2.5 mL), and phenoxyacetyl chloride (1.08 mL, 7.85 mmol) were added to the 1-hydroxybenzotriazole. The mixture was stirred at room temperature for 5 minutes, then cooled to 0° C., and dissolved in dehydrated pyridine (25 mL). 6-(Thien-2-yl)-9-(7-octynyl)-2-amino purine (1.60 g, 4.91 mmol) prepared in step 2) was added thereto. The mixture was stirred at room temperature overnight and was separated between ethyl acetate (150 mL) and saturated brine (150 mL) twice. The organic layer was dried over sodium sulfate and then concentrated. The concentrated product was purified by silica gel column chromatography (dichloromethane:methanol=from 100:0 to 99:1) to yield 6-(thien-2-yl)-9-(7-octynyl)-2-phenoxyacetamide purine (1.44 g, 3.13 mmol, 64%).

Physical properties of 6-(thien-2-yl)-9-(7-octynyl)-2-phenoxyacetamide purine $^1$H NMR (300 MHz, DMSO-d6) δ 10.71 (s, 1H), 8.62 (d, 1H, J=2.6 Hz), 8.54 (s, 1H), 7.92 (dd, 1H, J=1.1, 5.0 Hz), 7.31 (m, 3H), 6.92-6.93 (m, 3H), 5.15 (brs, 2H), 4.20 (t, 2H, J=7.1 Hz), 2.71 (t, 1H, J=2.6 Hz), 2.09-2.13 (m, 2H), 1.82-1.92 (m, 2H), 1.27-1.41 (m, 6H).

4) Synthesis of 5-[6-(thien-2-yl)-9-(7-octynyl)-2-phenoxyacetamide purine]-5'-O-(4,4'-dimethoxytrityl)-2'-deoxyuridine (step (d) in FIG. 30)

5'-O-(4,4'-Dimethoxytrityl)-5-iodo-2'-deoxyuridine (1.64 g, 2.5 mmol), tetrakis(triphenylphosphine)palladium(0) (145 mg, 0.125 mmol), copper iodide (76 mg, 0.4 mmol), and dehydrated dimethylformamide (7.5 mL) were added to a microwave machine. After the system was purged with argon gas, dehydrated triethylamine (523 μL, 3.75 mmol) was added, and then dehydrated dimethylformamide (5 mL) and dehydrated pyridine (10 mL) containing 6-(thien-2-yl)-9-(7-octynyl)-2-phenoxyacetamide purine (1.38 g, 3.00 mmol) prepared in step 3) were added thereto. The mixture was stirred at 60° C. for 3 hours with the microwave machine (standard mode) and was separated between ethyl acetate (100 mL) and water (100 mL). The organic layer was washed with saturated brine (100 mL), was dried over sodium sulfate, and then was concentrated. The concentrated product was purified by silica gel column chromatography (dichloromethane:methanol=from 100:0 to 97:3) to yield 5-[6-(thien-2-yl)-9-(7-octynyl)-2-phenoxyacetamide purine]-5'-O-(4,4'-dimethoxytrityl)-2'-deoxyuridine (931 mg, 0.94 mmol, 38%).

Physical properties of 5-[6-(thien-2-yl)-9-(7-octynyl)-2-phenoxyacetamide purine]-5'-O-(4,4'-dimethoxytrityl)-2'-deoxyuridine $^1$H NMR (300 MHz, DMSO-d6) δ 11.59 (brs, 1H), 10.70 (brs, 1H), 8.61 (dd, 1H, J=0.9, 3.8 Hz), 8.51 (s, 1H), 7.92 (dd, 1H, J=0.9, 5.0 Hz), 7.87 (s, 1H), 7.17-7.37 (m, 12H), 6.82-6.96 (m, 7H), 6.11 (t, 1H, J=6.6 Hz), 5.31 (d, 1H, J=4.4 Hz), 5.14 (brs, 2H), 4.02-4.28 (m, 3H), 3.70-3.91 (m, 1H), 3.12-3.16 (m, 2H), 2.04-2.24 (m, 4H), 1.76-1.99 (m, 2H), 1.15-1.20 (m, 6H).

5) Synthesis of 5-[6-(thien-2-yl)-9-(7-octynyl)-2-phenoxyacetamide purine]-5'-O-(4,4'-dimethoxytrityl)-2'-deoxyuridine-3'-O-(2-cyanoethyl-N,N-diisopropyl)phosphoramidite (step (e) in FIG. 30)

5-[6-(Thien-2-yl)-9-(7-octynyl)-2-phenoxyacetamide purine]-5'-O-(4,4'-dimethoxytrityl)-2'-deoxyuridine (890 mg, 0.9 mmol) prepared in step 4) was azeotropically dried with dehydrated pyridine three times and with dehydrated tetrahydrofuran three times. Subsequently, dehydrated tetrahydrofuran (4.5 mL), dehydrated diisopropylethylamine (235 μL, 1.35 mmol), and 2-cyanoethyl-N,N'-diisopropylchlorophosphoramidite (241 μL, 1.08 mmol) were added thereto, followed by stirring at room temperature for 1 hour. Dehydrated methanol (50 μL) was added to the mixture, and the resulting mixture was separated between ethyl acetate:triethylamine (20:1, 50 mL) and 5% sodium bicarbonate (50 mL). The organic layer was washed with saturated brine (100 mL), was dried over sodium sulfate, and was concentrated. The concentrated product was purified by silica gel column chromatography (hexane:ethyl acetate:triethylamine=from 98:0:2 to 78:20:2) to yield 5-[6-(thien-2-yl)-9-(7-octynyl)-2-phenoxyacetamide purine]-5'-O-(4,4'-dimethoxytrityl)-2'-deoxyuridine-3'-O-(2-cyanoethyl-N,N-diisopropyl)phosphoramidite (867 mg, 0.73 mmol, 81%).

Physical properties of 5-[6-(thien-2-yl)-9-(7-octynyl)-2-phenoxyacetamide purine]-5'-O-(4,4'-dimethoxytrityl)-2'-deoxyuridine-3'-O-(2-cyanoethyl-N,N-diisopropyl)phosphoramidite $^1$H NMR (300 MHz, DMSO-d6) δ 11.57 (brs, 1H), 10.70 (brs, 1H), 8.60 (dd, 1H, J=1.1, 3.7 Hz), 8.50 (s, 1H), 7.89-7.92 (m, 2H), 7.14-7.36 (m, 12H), 6.79-6.95 (m, 7H), 6.10 (dt, 1H, J=6.2, 6.3 Hz), 5.13 (brs, 2H), 4.50-4.60 (m, 1H), 4.16 (t, 2H, J=6.7 Hz), 3.99-4.06 (m, 1H), 3.17-3.71 (m, 12H), 2.26-2.76 (m, 4H), 2.05-2.10 (m, 2H), 1.74-1.77 (m, 2H), 0.82-1.39 (m, 18H).
$^{31}$P NMR (121 MHz, DMSO-d6) δ 148.67, 148.32.

Example 22

Chemical Synthesis of Dss-hx-dU Amidite Reagent (Compound Shown in FIG. 6) (FIG. 33)

1) Synthesis of 7-(2,2'-bithien-5-yl)-3-(7-octynyl)-imidazo[4,5-b]pyridine (step (a) in FIG. 33)

A DMF solution (15 mL) containing 7-(2,2'-bithien-5-yl) imidazo[4,5-b]pyridine (850 mg, 3.0 mmol) and potassium carbonate (1.3 g, 9.0 mmol) was stirred at 60° C. for 1 hour. Subsequently, 8-bromo-1-octyne (850 mg, 4.5 mmol) was added to the DMF solution, followed by stirring at 60° C. for 6 hours. The reaction solution was separated between ethyl acetate and water. The organic layer was washed with saturated brine, was dried over anhydrous sodium sulfate, and was purified by medium-pressure preparative column chromatography to yield 7-(2,2'-bithien-5-yl)-3-(7-octynyl)-imidazo[4,5-b]pyridine (520 mg, 1.3 mmol, 44%).

Physical properties of 7-(2,2'-bithien-5-yl)-3-(7-octynyl)-imidazo[4,5-b]pyridine $^1$H NMR (300 MHz, DMSO-d6) δ 8.56 (s, 1H), 8.34 (d, 1H, J=5.2 Hz), 8.21 (d, 1H, J=3.9 Hz), 7.63 (d, 1H, J=5.2 Hz), 7.58 (dd, 1H, J=1.1, 5.1 Hz), 7.46 (dd, 1H, J=1.1, 3.6 Hz), 7.44 (d, 1H, J=4.0 Hz), 7.14 (dd, 1H, J=3.6, 5.1 Hz), 4.29 (t, 2H, J=7.4 Hz), 2.72 (t, 1H, J=2.7 Hz), 2.12 (m, 2H), 1.87 (m, 2H), 1.43-1.31 (m, 6H).

2) Synthesis of 5-[7-(2,2'-bithien-5-yl)-3-(7-octynyl)-imidazo[4,5-b]pyridine]-2'-deoxyuridine (step (b) in FIG. 33)

A DMF (4.2 mL) solution containing 5-iodo-2'-deoxyuridine (294 mg, 0.83 mmol), 7-(2,2'-bithienyl)-3-(7-octynyl)-imidazo[4,5-b]pyridine (270 mg, 0.69 mmol), CuI (25 mg), tetrakistriphenylphosphine (48 mg), and triethylamine (173 μL) was stirred at room temperature for 17 hours. The reaction solution was separated between ethyl acetate and water. The organic layer was washed with saturated brine, was dried over anhydrous sodium sulfate, and was purified by column chromatography (eluted with a 3% methanol solution in methylene chloride) to yield 5-[7-(2,2'-bithien-5-yl)-3-(7-octynyl)-imidazo[4,5-b]pyridine]-2'-deoxyuridine (155 mg, 0.25 mmol, 36%).

Physical properties of 5-[7-(2,2'-bithien-5-yl)-3-(7-octynyl)-imidazo[4,5-b]pyridine]-2'-deoxyuridine $^1$H NMR (300 MHz, DMSO-d6) δ 11.54 (s, 1H), 8.56 (s, 1H), 8.34 (d, 1H, J=5.2 Hz), 8.21 (d, 1H, J=3.9 Hz), 8.09 (s, 1H), 7.63 (d, 1H, J=5.2 Hz), 7.58 (dd, 1H, J=1.1, 5.1 Hz), 7.46 (dd, 1H, J=1.1, 3.6 Hz), 7.44 (d, 1H, J=4.1 Hz), 7.14 (dd, 1H, J=3.6, 5.1 Hz), 6.10 (t, 1H, J=6.9 Hz), 5.21 (d, 1H, J=4.3 Hz), 5.06 (t, 1H, J=5.0 Hz), 4.30 (t, 2H, J=7.2 Hz), 4.21 (m, 1H), 3.77 (m, 1H), 3.56 (m, 2H), 2.33 (m, 2H), 2.09 (m, 2H), 1.88 (m, 2H), 1.45 (m, 4H), 1.29 (m, 2H).

3) Synthesis of 5-[7-(2,2'-bithien-5-yl)-3-(7-octynyl)-imidazo[4,5-b]pyridine]-5'-O-(4,4-dimethoxytrityl)-2'-deoxyuridine (step (c) in FIG. 33)

A pyridine (2.4 mL) solution containing 5-[7-(2,2'-bithien-5-yl)-3-(7-octynyl)-imidazo[4,5-b]pyridine]-2'-deoxyuridine (150 mg, 0.24 mmol) and 4,4'-dimethoxytrityl chloride (91 mg, 0.27 mmol) was stirred at room temperature for 1 hour. The reaction solution was separated between ethyl acetate and an aqueous 5% sodium bicarbonate solution. The organic layer was washed with saturated brine, was dried over anhydrous sodium sulfate, and was purified by column chromatography (eluted with a 2% methanol solution in methylene chloride) to yield 5-[7-(2,2'-bithienyl)-3-(7-octynyl)-imidazo[4,5-b]pyridine]-5'-O-(4,4-dimethoxytrityl)-2'-deoxyuridine (183 mg, 0.2 mmol, 82%).

Physical properties of 5-[7-(2,2'-bithien-5-yl)-3-(7-octynyl)-imidazo[4,5-b]pyridine]-5'-O-(4,4-dimethoxytrityl)-2'-deoxyuridine $^1$H NMR (300 MHz, DMSO-d6) δ 11.58 (s, 1H), 8.53 (s, 1H), 8.32 (d, 1H, J=5.2 Hz), 8.20 (d, 1H, J=3.9 Hz), 7.87 (s, 1H), 7.60-7.57 (m, 2H), 7.46-7.43 (m, 2H), 7.35-7.32 (m, 2H), 7.26-7.13 (m, 8H), 6.81 (d, 4H, J=9.0 Hz), 6.10 (t, 1H, J=7.0 Hz), 5.30 (d, 1H, J=4.4 Hz), 4.26 (m, 3H), 3.89 (m, 1H), 3.69 (s, 6H), 3.15 (m, 2H), 2.18 (m, 2H), 2.05 (m, 2H), 1.78 (m, 2H), 1.22-1.13 (m, 6H).

4) Synthesis of 5-[7-(2,2'-bithien-5-yl)-3-(7-octynyl)-imidazo[4,5-b]pyridine]-5'-O-(4,4'-dimethoxytrityl)-2'-deoxyuridine-3'-O-(2-cyanoethyl-N,N-diisopropyl)phosphoramidite (step (d) in FIG. 33)

5-[7-(2,2'-Bithien-5-yl)-3-(7-octynyl)-imidazo[4,5-b]pyridine]-5'-O-(4,4-dimethoxytrityl)-2'-deoxyuridine (180 mg, 0.2 mmol) was azeotropically dried with pyridine three times and with THF three times. Subsequently, THF (1.0 mL) and diisopropylethylamine (52 μL) were added thereto, and the mixture was stirred. 2-Cyanoethyl-N,N-diisopropylchlorophosphoramidite (54 μL, 0.24 mmol) was added to this solution, followed by stirring at room temperature for 1 hour. Dehydrated methanol (50 μL) was added to the reaction solution, and the resulting mixture was separated between a mixture of ethyl acetate:triethylamine (20:1, v/v) and an aqueous 5% sodium bicarbonate solution. The organic layer was washed with saturated brine, was dried over anhydrous sodium sulfate, and was concentrated. The residue was purified by silica gel column chromatography (eluted with ethyl acetate:methylene chloride:triethylamine=45:45:10, v/v/v) to yield 5-[7-(2,2'-bithien-5-yl)-3-(7-octynyl)-imidazo[4,5-b]pyridine]-5'-O-(4,4'-dimethoxytrityl)-2'-deoxyuridine-3'-O-(2-cyanoethyl-N,N-diisopropyl)phosphoramidite (220 mg, 99%).

Physical properties of 5-[7-(2,2'-bithien-5-yl)-3-(7-octynyl)-imidazo[4,5-b]pyridine]-5'-O-(4,4'-dimethoxytrityl)-2'-deoxyuridine-3'-O-(2-cyanoethyl-N,N-diisopropyl)phosphoramidite $^1$H NMR (300 MHz, DMSO-d6) δ 11.59 (s, 1H), 8.53 (s, s, 1H, 1H), 8.32 (d, 1H, J=5.2 Hz), 8.20 (d, 1H, J=3.9 Hz), 7.89 (d, 1H, J=2.1 Hz), 7.60-7.57 (m, 2H), 7.46-7.43 (m, 2H), 7.34 (m, 2H), 7.26-7.13 (m, 8H), 6.81 (m, 4H), 6.98 (dt, 1H, J=6.3, 6.5 Hz), 4.47 (m, 1H), 4.25 (t, 2H, J=6.9 Hz), 4.05-3.98 (m, 1H), 3.71 (m, 1H), 3.69 (s, 6H), 3.60-3.42 (m, 2H), 3.20 (m, 2H), 2.73 (t, 1H, J=5.9 Hz), 2.61 (t, 1H, J=5.9 Hz), 2.44-2.25 (m, 2H), 2.07 (m, 2H), 1.77 (m, 2H), 1.09 (m, 18H).
$^{31}$P NMR (121 MHz, DMSO-d6) δ 148.68, 148.32.

Example 23

Figure 3:
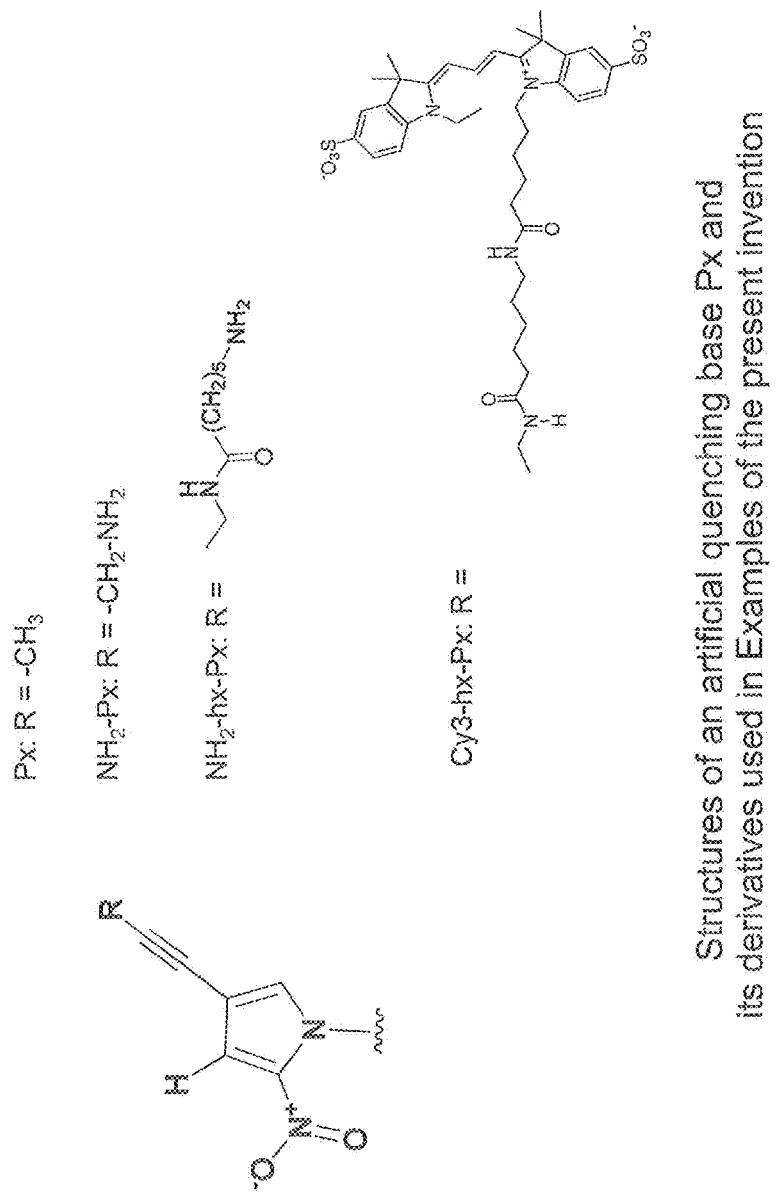
FIG. 3 shows structures of an artificial quenching base Px and its derivatives used in Examples of the present invention.
Figure 4:
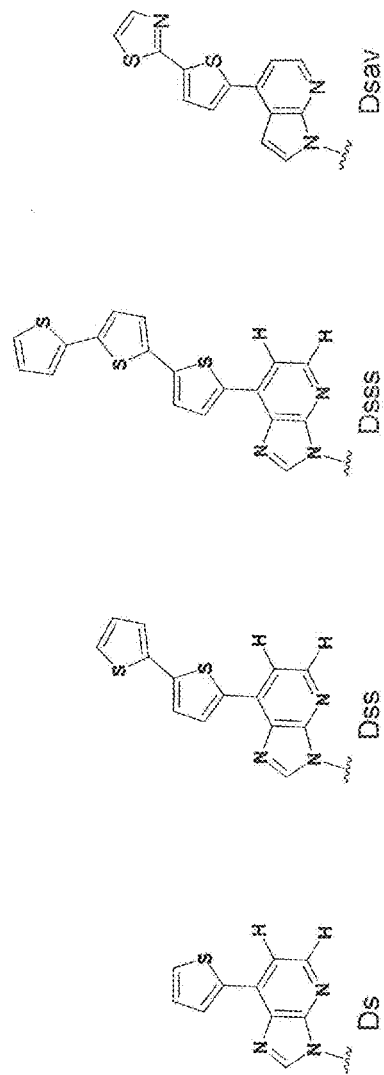
FIG. 4 shows structures of Ds and artificial fluorescent bases Dss, Dsss, and Dsav as examples of the artificial base complementary to Pn or Px used in the method of the present invention.

Synthesis of Compounds Shown in FIGS. 2 and 3

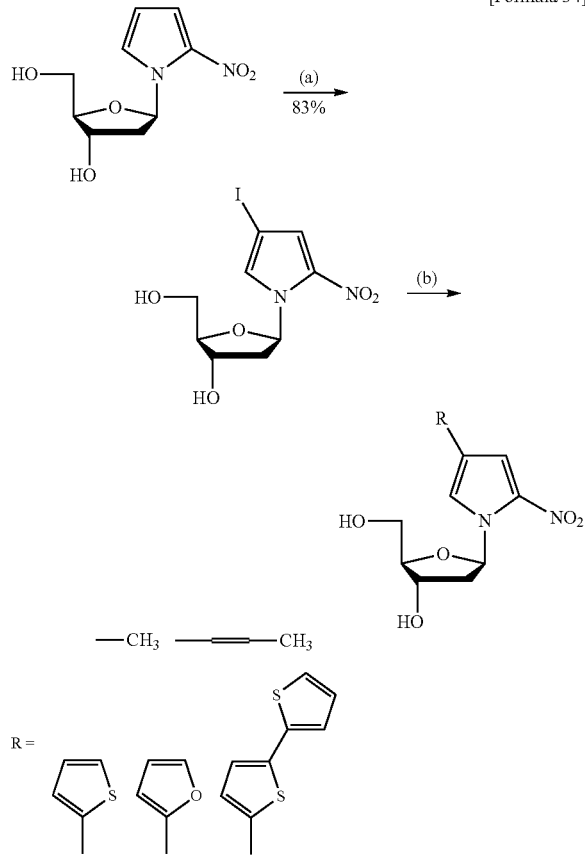

Conditions: (a) NIS, CH$_3$CN (b) Pd(PPh$_3$)$_2$Cl$_2$, DMF

1) Synthesis of 1-(2-deoxy-β-D-ribofuranosyl)-4-iodo-2-nitropyrrole

N-Iodosuccinimide (900 mg, 4 mmol) was added to a 1-(2-deoxy-(3-D-ribofuranosyl)-2-nitropyrrole (456 mg, 2 mmol) solution in acetonitrile (8 mL). The mixture was stirred at room temperature overnight and then separated between ethyl acetate (200 mL) and water (200 mL). The organic layer was concentrated and purified by silica gel column chromatography and HPLC to yield 1-(2-deoxy-β-D-ribofuranosyl)-4-iodo-2-nitropyrrole (587 mg, 1.66 mmol, 83%).

Physical properties of 1-(2-deoxy-β-D-ribofuranosyl)-4-iodo-2-nitropyrrole $^1$H NMR (270 MHz, DMSO-d6) δ 7.90 (d, 1H, J=2.0 Hz), 7.40 (d, 1H, J=2.0 Hz), 6.54 (t, 1H, J=5.6 Hz), 5.27 (d, 1H, J=4.3 Hz), 5.10 (t, 1H, J=4.9 Hz), 4.23 (m, 1H), 3.83 (m, 1H), 3.53-3.85 (m, 2H), 2.18-2.45 (m, 2H).

2) Synthesis of 1-(2-deoxy-β-D-ribofuranosyl)-4-(thien-2-yl)-2-nitropyrrole 2-(Tributylstannyl)thiophene (476 μL, 1.5 mmol) was added to a DMF (2.5 mL) solution containing 1-(2-deoxy-β-D-ribofuranosyl)-4-iodo-2-nitropyrrole (177 mg, 0.5 mmol) and bis(triphenylphosphine)palladium(II) dichloride (18 mg, 0.025 mmol). The mixture was reacted at 100° C. for 30 minutes in a microwave machine (standard mode). The reaction solution was separated between ethyl acetate (50 mL) and water (50 mL). The organic layer was concentrated and purified by HPLC to yield 1-(2-deoxy-β-D-ribofuranosyl)-4-(thien-2-yl)-2-nitropyrrole (97 mg, 0.32 mmol, 63%).

Physical properties of 1-(2-deoxy-β-D-ribofuranosyl)-4-(thien-2-yl)-2-nitropyrrole $^1$H NMR (300 MHz, DMSO-d6) δ 8.13 (d, 1H, J=2.3 Hz), 7.52 (d, 1H, J=2.3 Hz), 7.42 (dd, 1H, J=1.1, 5.1 Hz), 7.33 (dd, 1H, J=1.1, 3.5 Hz), 7.06 (dd, 1H, J=3.6, 5.1 Hz), 6.59 (t, 1H, J=5.7 Hz), 5.30 (d, 1H, J=4.6 Hz), 5.17 (t, 1H, J=5.1 Hz), 4.28 (m, H), 3.86 (m, 1H), 3.70-3.74 (m, 1H), 3.58-3.69 (m, 1H), 2.41-2.45 (m, 1H), 2.25-2.33 (m, 1H).

3) Synthesis of 1-(2-deoxy-β-D-ribofuranosyl)-4-(furan-2-yl)-2-nitropyrrole 2-(Tributylstannyl)furan (472 μL, 1.5 mmol) was added to a DMF (2.5 mL) solution containing 1-(2-deoxy-β-D-ribofuranosyl)-4-iodo-2-nitropyrrole (177 mg, 0.5 mmol) and bis(triphenylphosphine)palladium(II) dichloride (18 mg, 0.025 mmol). The mixture was reacted at 100° C. for 30 minutes in a microwave machine (standard mode). The reaction solution was separated between ethyl acetate (50 mL) and water (50 mL). The organic layer was concentrated and purified by HPLC to yield 1-(2-deoxy-β-D-ribofuranosyl)-4-(furan-2-yl)-2-nitropyrrole (111 mg, 0.38 mmol, 76%).

Physical properties of 1-(2-deoxy-β-D-ribofuranosyl)-4-(furan-2-yl)-2-nitropyrrole $^1$H NMR (300 MHz, DMSO-d6) δ 8.08 (d, 1H, J=2.3 Hz), 7.63 (dd, 1H, J=0.7, 1.8 Hz), 7.50 (d, 1H, J=2.3 Hz), 6.69 (dd, 1H, J=0.7, 3.3 Hz), 6.61 (t, 1H, J=5.7 Hz), 6.53 (dd, 1H, J=1.8, 3.3 Hz), 5.29 (d, 1H, J=4.4 Hz), 5.12 (t, 1H, J=5.1 Hz), 4.27 (m, 1H), 3.87 (m, 1H), 3.65-3.72 (m, 1H), 3.56-3.63 (m, 1H), 2.41-2.46 (m, 1H), 2.23-2.31 (m, 1H).

4) Synthesis of 1-(2-deoxy-β-D-ribofuranosyl)-4-(2, 2'-bithien-5-yl)-2-nitropyrrole 2-(Tributylstannyl)dithiophene (341 mg, 0.75 mmol) was added to a DMF (2.5 mL) solution containing 1-(2-deoxy-β-D-ribofuranosyl)-4-iodo-2-nitropyrrole (177 mg, 0.5 mmol) and bis(triphenylphosphine)palladium(II) dichloride (18 mg, 0.025 mmol). The mixture was reacted at 100° C. for 30 minutes in a microwave machine (standard mode). The reaction solution was separated between ethyl acetate (50 mL) and water (50 mL). The organic layer was concentrated and purified by HPLC to yield 1-(2-deoxy-β-D-ribofuranosyl)-4-(2,2'-bithien-5-yl)-2-nitropyrrole (90 mg, 0.23 mmol, 46%).

Physical properties of 1-(2-deoxy-β-D-ribofuranosyl)-4-(2,2'-bithien-5-yl)-2-nitropyrrole $^1$H NMR (300 MHz, DMSO-d6) δ 8.15 (d, 1H, J=2.3 Hz), 7.57 (d, 1H, J=2.3 Hz), 7.50 (dd, 1H, J=1.1, 5.1 Hz), 7.24-7.31 (m, 3H), 7.08 (dd, 1H, J=3.6, 5.1 Hz), 6.60 (t, 1H, J=5.7 Hz), 5.28 (d, 1H, J=3.6 Hz), 5.17 (t, 1H, J=5.2 Hz), 4.29 (m, 1H), 3.87 (m, 1H), 3.68-3.75 (m, 1H), 3.57-3.65 (m, 1H), 2.41-2.46 (m, 1H), 2.26-2.34 (m, 1H).

5) Synthesis of 1-(2-deoxy-β-D-ribofuranosyl)-4-methyl-2-nitropyrrole

Tetramethyltin (287 μL, 2 mmol) was added to a DMF (2 mL) solution containing 1-(2-deoxy-β-D-ribofuranosyl)-4-iodo-2-nitropyrrole (142 mg, 0.4 mmol), bis(triphenylphosphine)palladium(II) dichloride (14 mg, 0.02 mmol), and triphenylarsine (12 mg, 0.04 mmol), followed by reaction at 60° C. for 2 days. The reaction solution was separated between ethyl acetate (50 mL) and water (50 mL). The organic layer was concentrated and purified by HPLC to yield 1-(2-deoxy-β-D-ribofuranosyl)-4-methyl-2-nitropyrrole (15 mg, 0.06 mmol, 15%).

Physical properties of 1-(2-deoxy-β-D-ribofuranosyl)-4-methyl-2-nitropyrrole $^1$H NMR (300 MHz, DMSO-d6) δ 7.55 (d, 1H, J=2.8 Hz), 7.09 (d, 1H, J=2.2 Hz), 6.55 (t, 1H, J=5.9 Hz), 5.27 (d, 1H, J=4.3 Hz), 5.00 (t, 1H, J=5.3 Hz), 4.22 (m, 1H), 3.82 (m, 1H), 3.52-3.64 (m, 2H), 2.34-2.42 (m, 1H), 2.11-2.19 (m, 1H), 2.02 (s, 3H).

6) Synthesis of 1-(2-deoxy-β-D-ribofuranosyl)-4-propynyl-2-nitropyrrole (FIG. 3, R=—CH$_3$)

Tributyl(1-propynyl)tin (327 μL, 1 mmol) was added to a DMF (5 mL) solution containing 1-(2-deoxy-β-D-ribofuranosyl)-4-iodo-2-nitropyrrole (180 mg, 0.5 mmol) and bis(triphenylphosphine)palladium(II) dichloride (38 mg, 0.05 mmol), followed by reaction at 100° C. for 90 minutes. The reaction solution was concentrated and purified by silica gel column chromatography and HPLC to yield 1-(2-deoxy-β-D-ribofuranosyl)-4-propynyl-2-nitropyrrole (76 mg, 0.28 mmol, 57%).

Physical properties of 1-(2-deoxy-β-D-ribofuranosyl)-4-propynyl-2-nitropyrrole $^1$H NMR (300 MHz, DMSO-d6) δ 7.92 (d, 1H, J=2.2 Hz), 7.27 (d, 1H, J=2.2 Hz), 6.55 (t, 1H, J=5.7 Hz), 5.28 (d, 1H, J=4.5 Hz), 5.11 (t, 1H, J=5.2 Hz), 4.24 (m, 1H), 3.85 (m, 1H), 3.53-3.70 (m, 2H), 2.45 (m, 1H), 2.22 (m, 1H), 1.99 (s, 3H).

The invention claimed is:

1. A method of detecting formation of a base pair of artificial bases, the method comprising:
observing a decrease in fluorescence of an artificial fluorescent base, wherein
the decrease in fluorescence of an artificial fluorescent base is caused by formation of a base pair of an artificial fluorescent base and a quenching base, wherein
the artificial fluorescent base is selected from the group consisting of:

(i) a 7-(2,2'-bithien-5-yl)imidazo[4,5-b]pyridin-3-yl group (Dss);

(ii) a 7-(2,2',5',2''-terthien-5-yl)imidazo[4,5-b]pyridin-3-yl group (Dsss);

(iii) a 2-amino-6-(2,2'-bithien-5-yl)purin-9-yl group (ss);

(iv) a 2-amino-6-(2',5',2''-terthien-5-yl)purin-9-yl group (sss);
(v) a 4-(2,2'-bithien-5-yl)-pyrrolo[2,3-b]pyridin-1-yl group (Dsas);
(vi) a 4-[2-(2-thiazolyl)thien-5-yl]pyrrolo[2,3-b]pyridin-1-yl group (Dsav); and
(vii) a 4-[5-(2-thienyl)thiazol-2-yl]pyrrolo[2,3-b]pyridin-1-yl group (Dvas); and
the quenching base having a 2-nitropyrrole structure is represented by Formula III or IV:

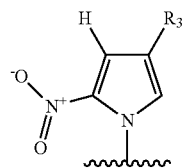

Formula III wherein $R_3$ is selected from —H, iodine, —CH$_3$, and:

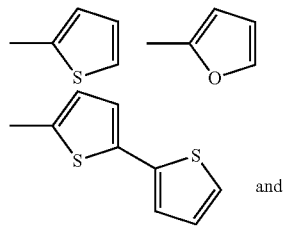

and

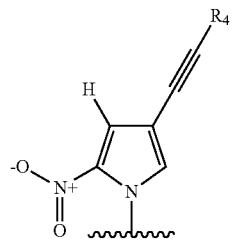

Formula IV wherein $R_4$ is selected from —CH$_3$, —CH$_2$—NH$_2$, and:

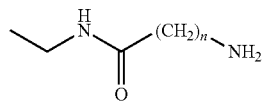

wherein n is an integer of 0 to 12, and
wherein the nitrogen atom at the 2-position of the 2-nitropyrrole structure is attached to a ribose or deoxyribose to form a nucleoside or nucleotide.

2. A kit used in a method of detecting formation of a base pair of artificial bases by observing a decrease in fluorescence of an artificial fluorescent base, the kit comprising:
a nucleic acid primer comprising a polynucleotide having a 7-(2,2'-bithien-5-yl)imidazo[4,5-b]pyridin-3-yl group (Dss) as a base; and
a polynucleotide having a quenching base having a 2-nitropyrrole structure represented by Formula III or IV

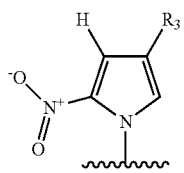

Formula III wherein $R_3$ is selected from —H, iodine, —CH$_3$, and:

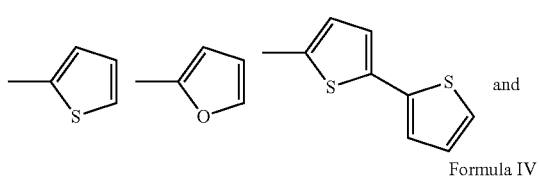

and

Formula IV

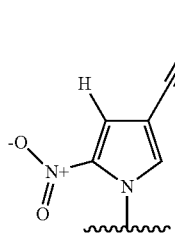

wherein $R_4$ is selected from —CH$_3$, —CH$_2$—NH$_2$, and:

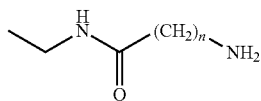

wherein n is an integer of 0 to 12, and
wherein the nitrogen atom at the 2-position of the 2-nitropyrrole structure is attached to a ribose or deoxyribose to form a nucleoside or nucleotide.

* * * * *